(12) United States Patent
Lavi et al.

(10) Patent No.: US 6,689,108 B2
(45) Date of Patent: Feb. 10, 2004

(54) DEVICE FOR MEASURING A VOLUME OF DRUG

(75) Inventors: Gilad Lavi, Rishon Letzion (IL); Gil Yigal, Gan Yavne (IL); Izrail Tsals, Sudbury, MA (US)

(73) Assignee: Elan Pharma International Limited, Shannon (IE)

( * ) Notice: Subject to any disclaimer, the term of this patent is extended or adjusted under 35 U.S.C. 154(b) by 0 days.

(21) Appl. No.: 09/812,990

(22) Filed: Mar. 20, 2001

(65) Prior Publication Data

US 2002/0007671 A1 Jan. 24, 2002

Related U.S. Application Data

(63) Continuation-in-part of application No. 09/439,879, filed on Nov. 12, 1999.
(60) Provisional application No. 60/108,382, filed on Nov. 13, 1998, provisional application No. 60/131,644, filed on Apr. 29, 1999, and provisional application No. 60/192,743, filed on Mar. 28, 2000.

(51) Int. Cl.[7] ........................ A61M 5/00; A61M 37/00; A61M 5/20; A61M 5/24

(52) U.S. Cl. ........................ 604/211; 604/131; 604/138; 604/205; 604/232; 604/246

(58) Field of Search ................................ 604/110, 131, 604/138, 139, 156, 181, 183, 186, 187, 191, 192, 194, 195, 196, 197, 199, 200, 205, 207, 211, 224, 232, 246, 264, 272, 518

(56) References Cited

U.S. PATENT DOCUMENTS

| | | | | | |
|---|---|---|---|---|---|
| 4,810,249 A | * | 3/1989 | Haber et al. | ................. | 222/390 |
| 4,973,318 A | * | 11/1990 | Holm et al. | ................. | 604/208 |
| 5,226,896 A | * | 7/1993 | Harris | ......................... | 604/208 |
| 5,308,341 A | * | 5/1994 | Chanoch | ..................... | 604/207 |
| 5,334,162 A | * | 8/1994 | Harris | ......................... | 604/232 |
| 5,843,042 A | * | 12/1998 | Ren | ............................. | 604/207 |

* cited by examiner

*Primary Examiner*—Manuel Mendez
*Assistant Examiner*—Mark K. Han
(74) *Attorney, Agent, or Firm*—Caesar, Rivise, Bernstein, Cohen & Pokotilow, Ltd.

(57) ABSTRACT

A device for measuring a volume of liquid drug. The device includes a first chamber containing liquid drug, a measurement chamber in liquid communication with the first chamber, and a measurement assembly.

17 Claims, 84 Drawing Sheets

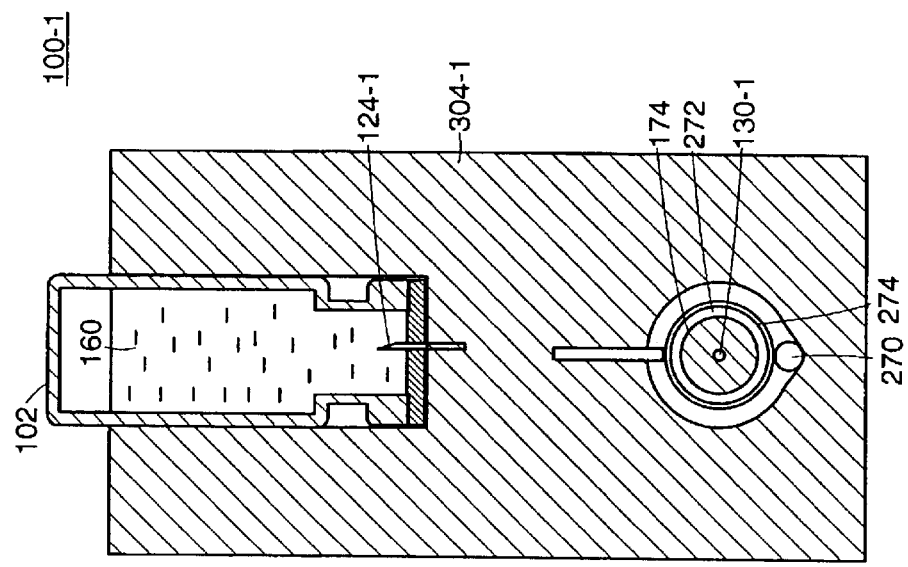
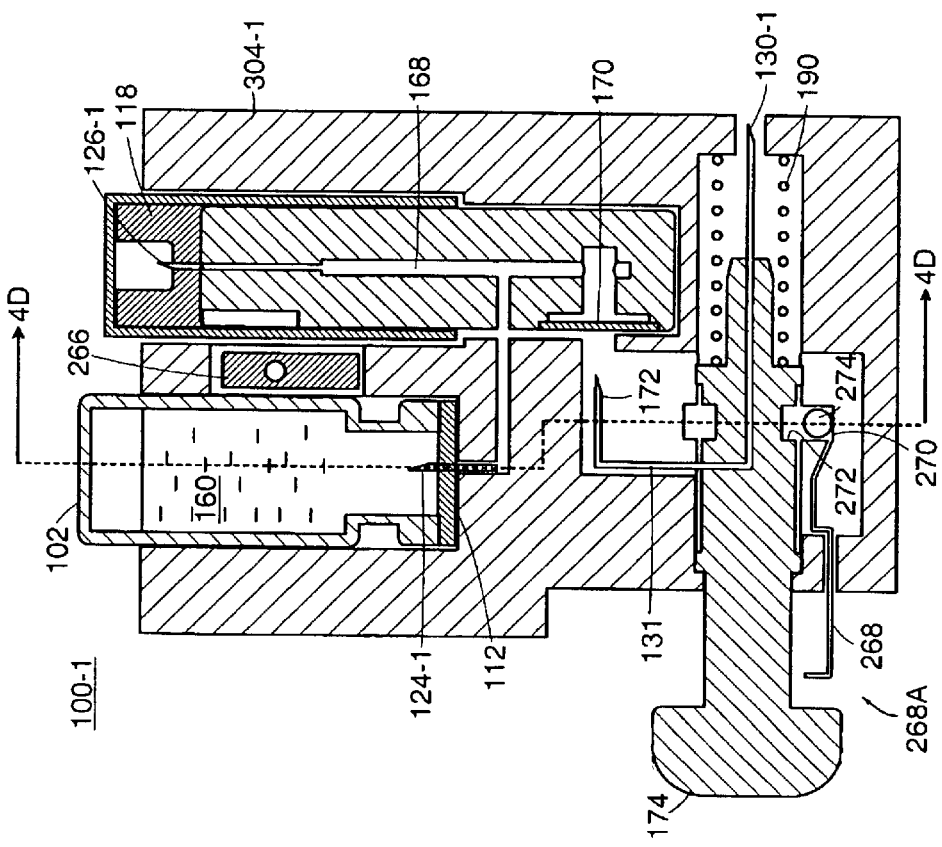

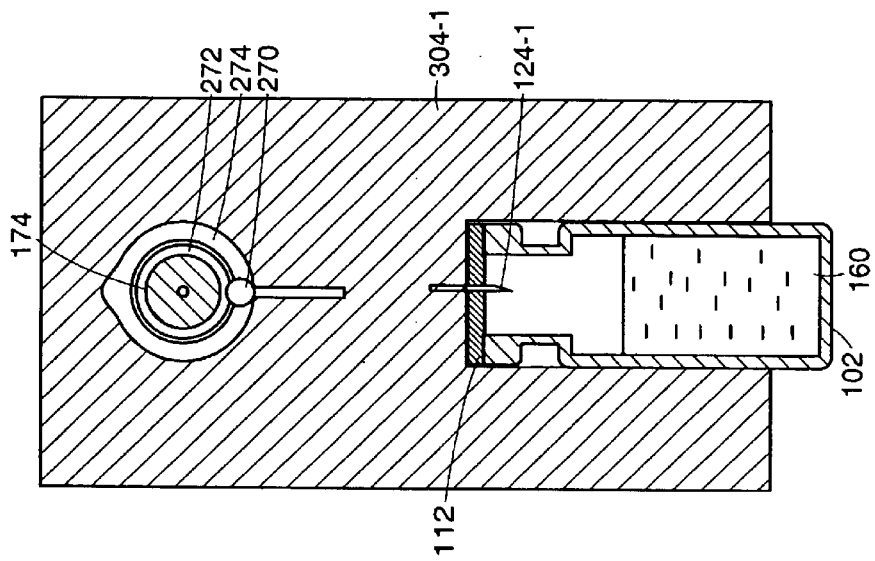
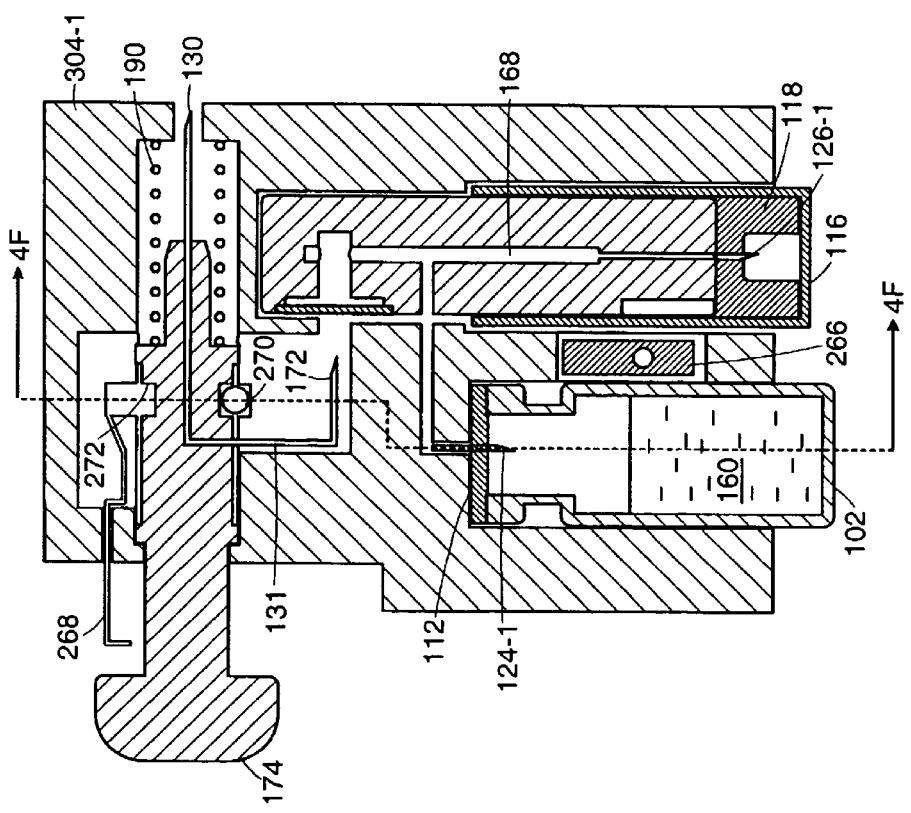

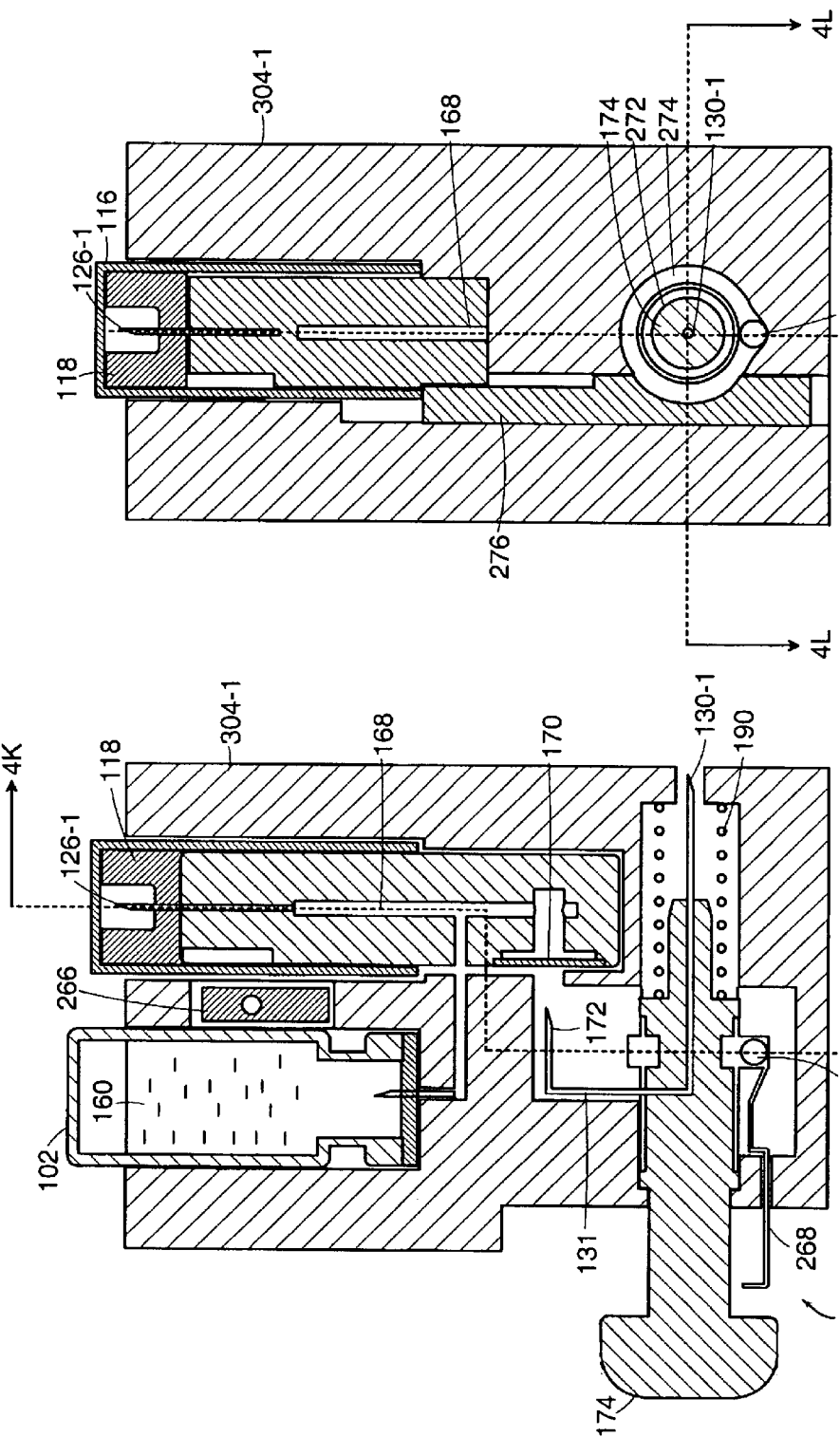

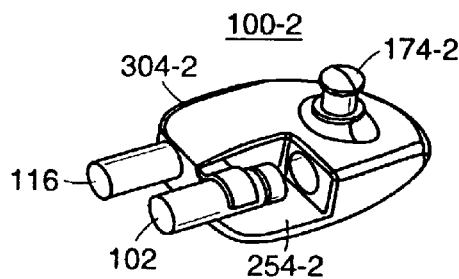 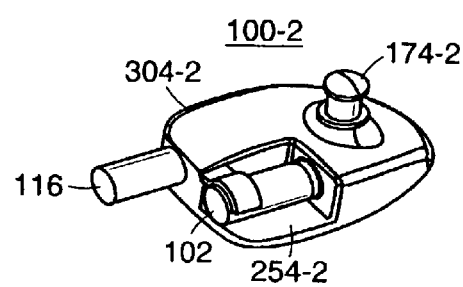
Figure 5A  Figure 5B
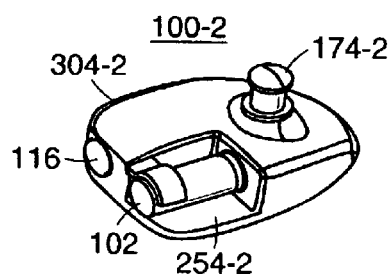
Figure 5C

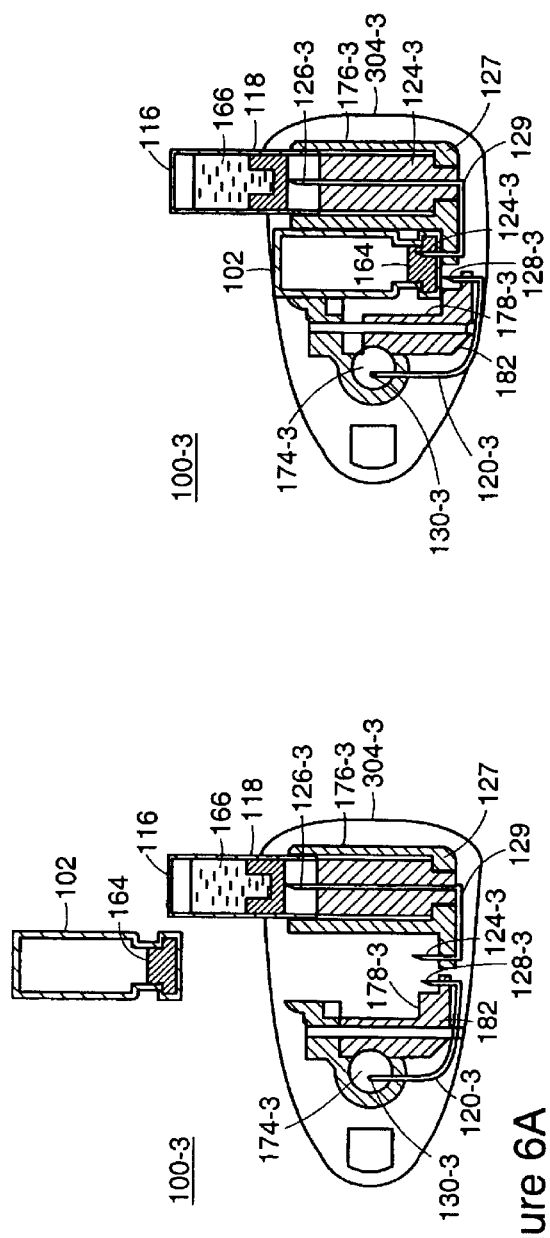
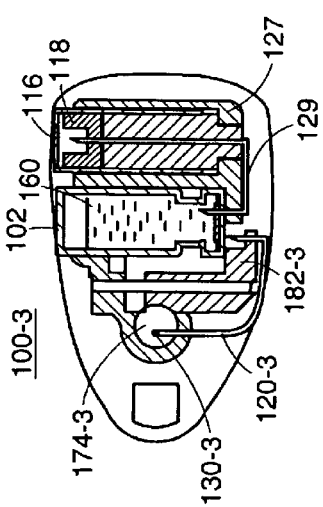

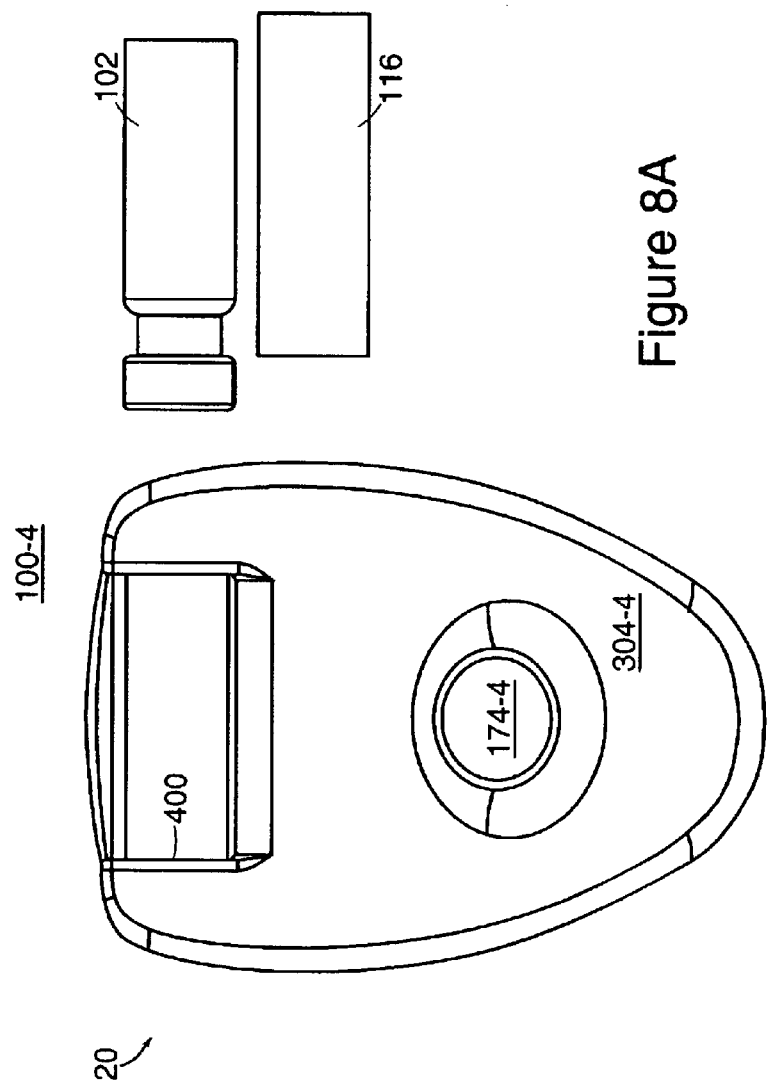

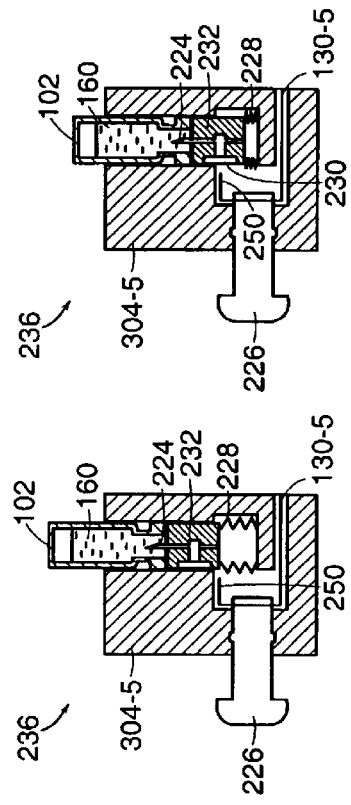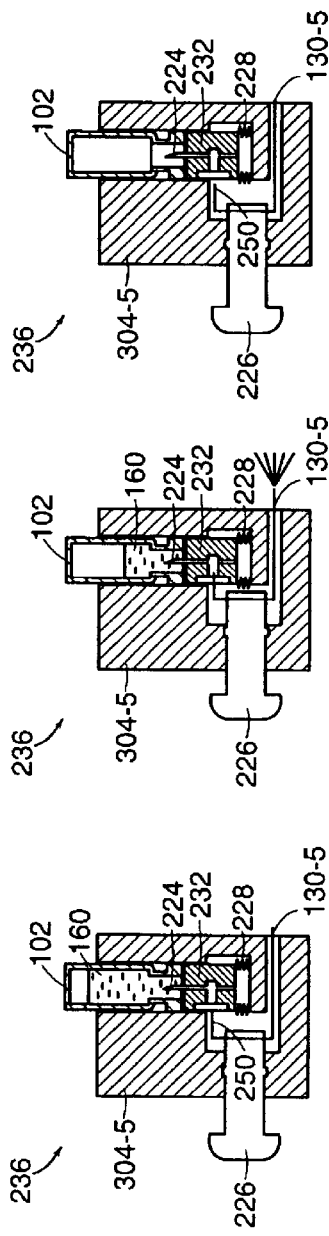

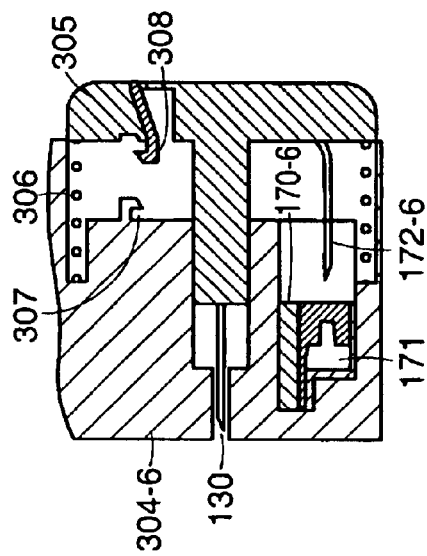
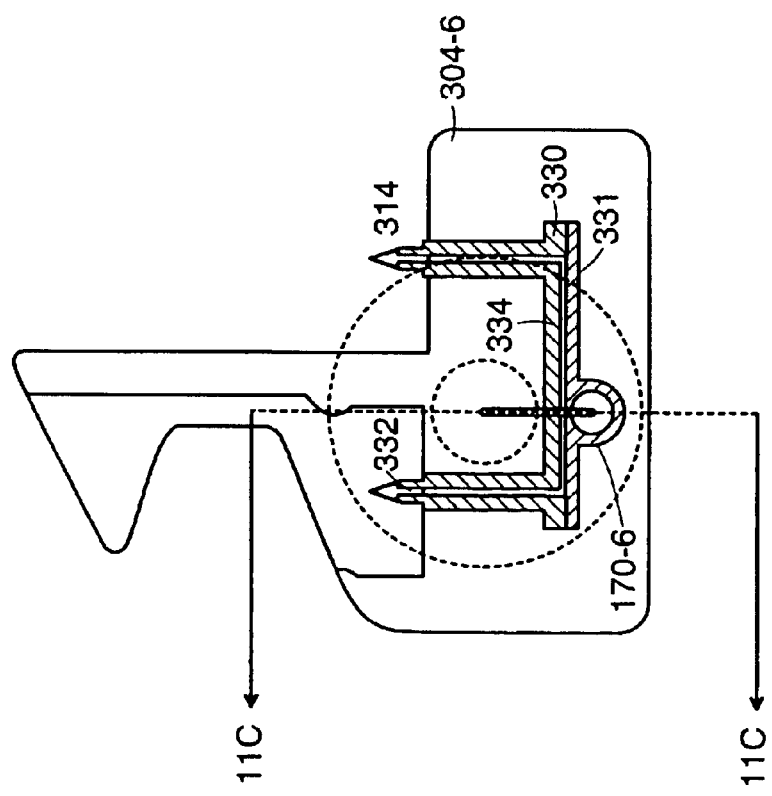
Figure 11C
Figure 11B

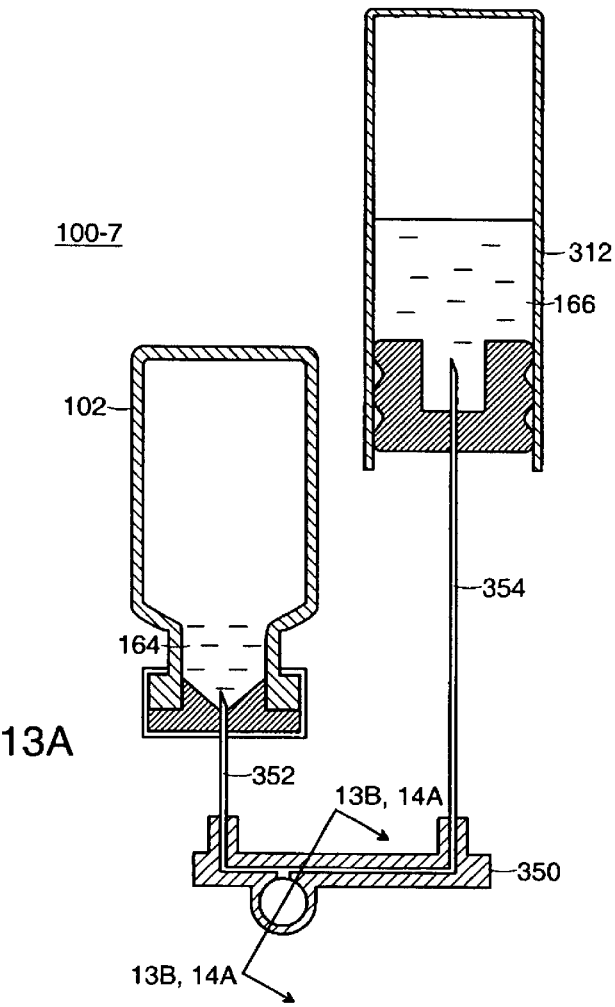
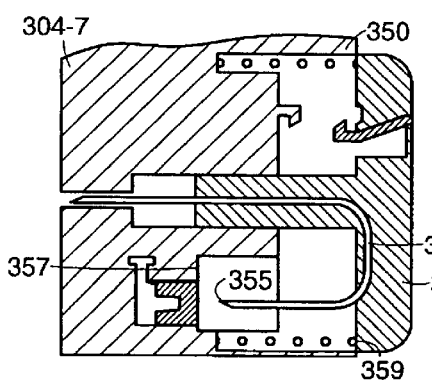
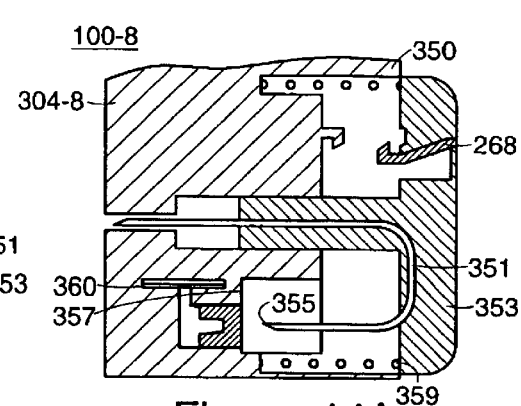
Figure 13A
Figure 13B
Figure 14A

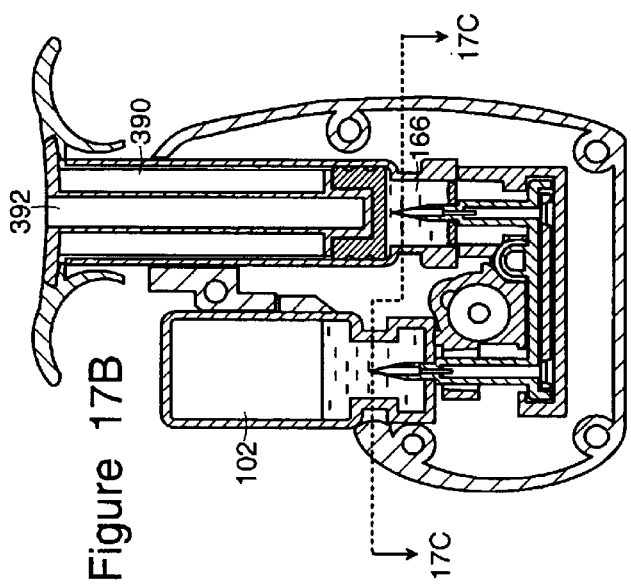
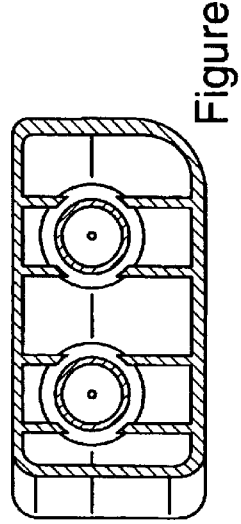
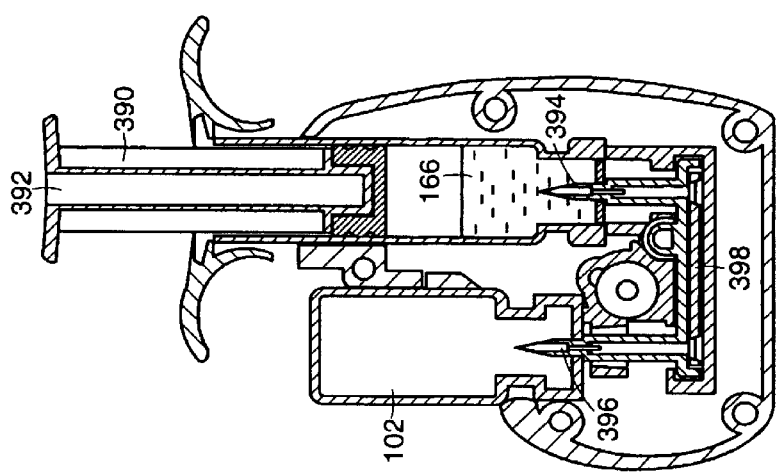

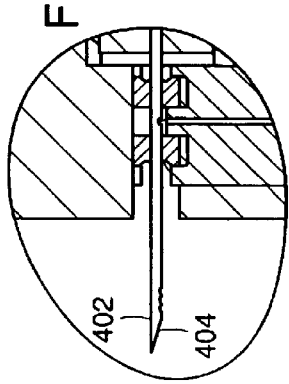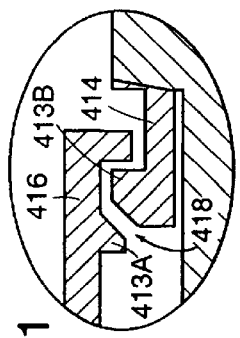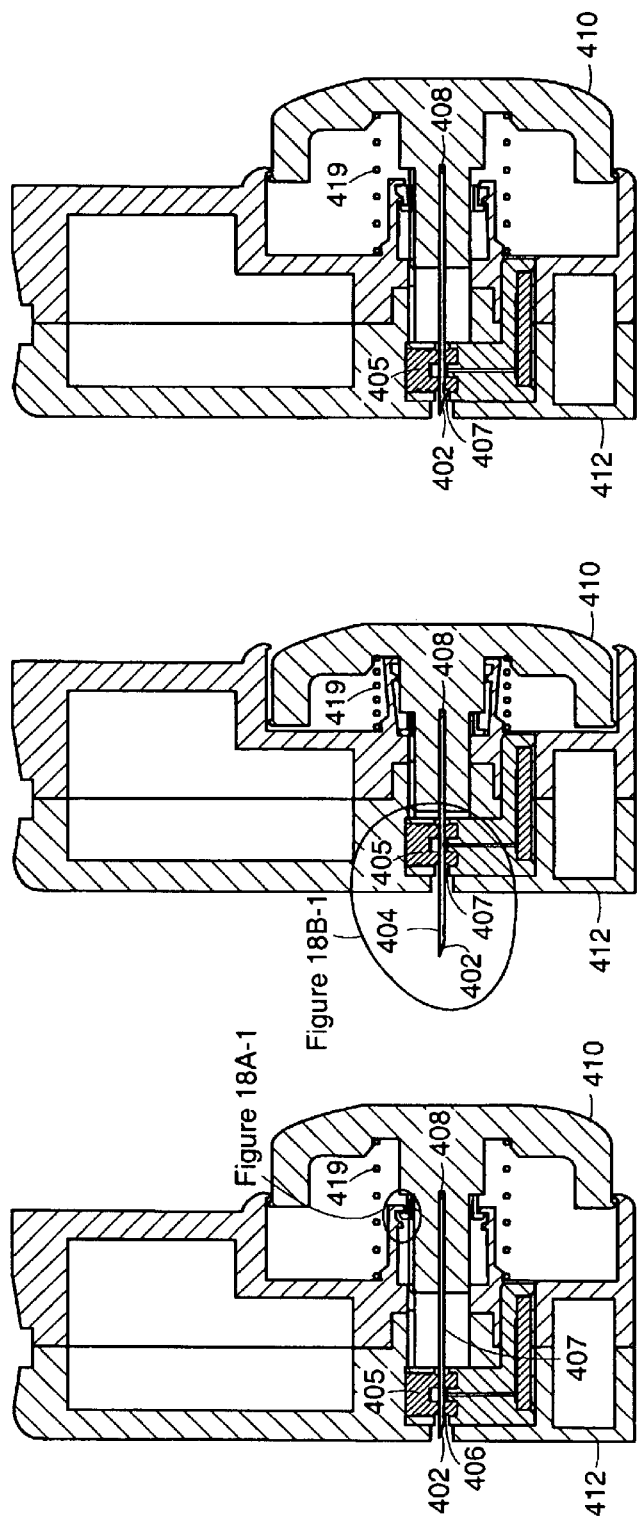

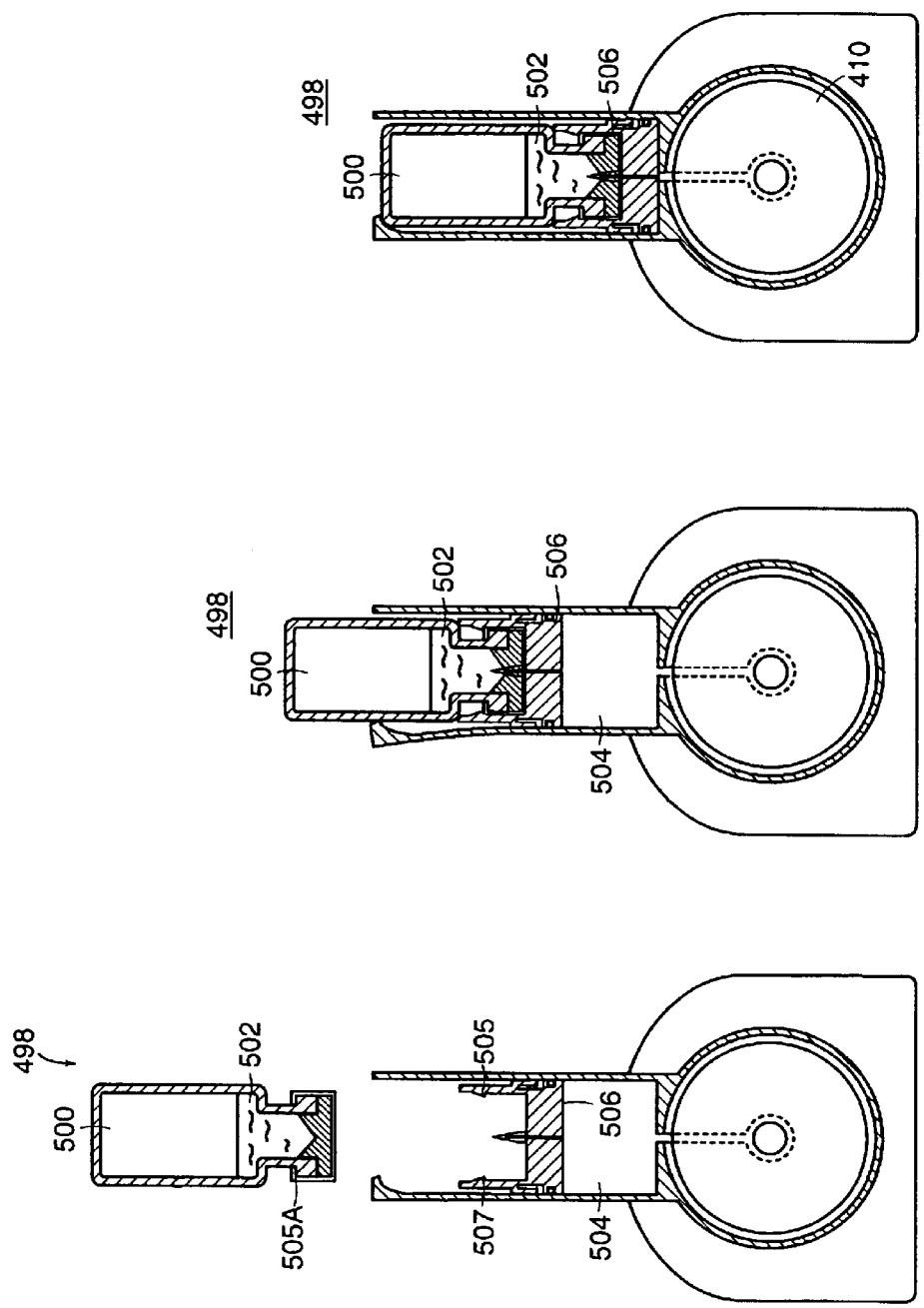

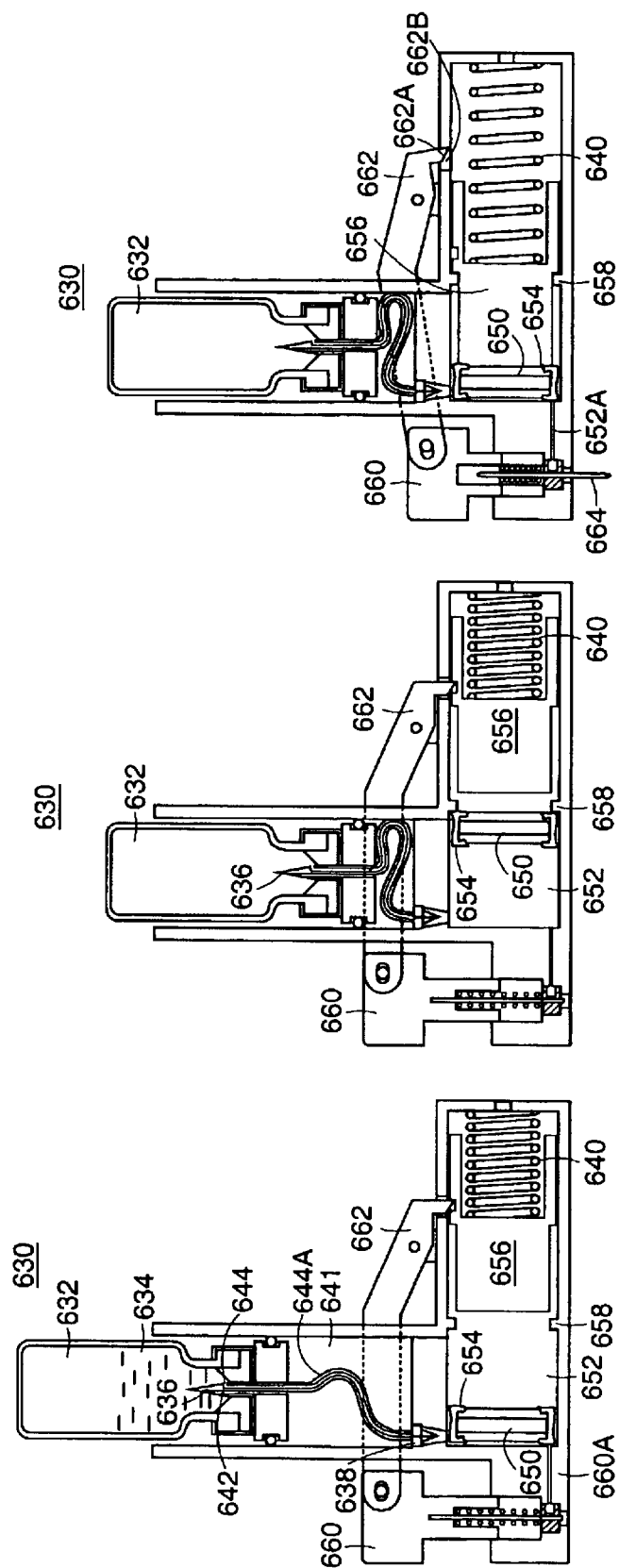

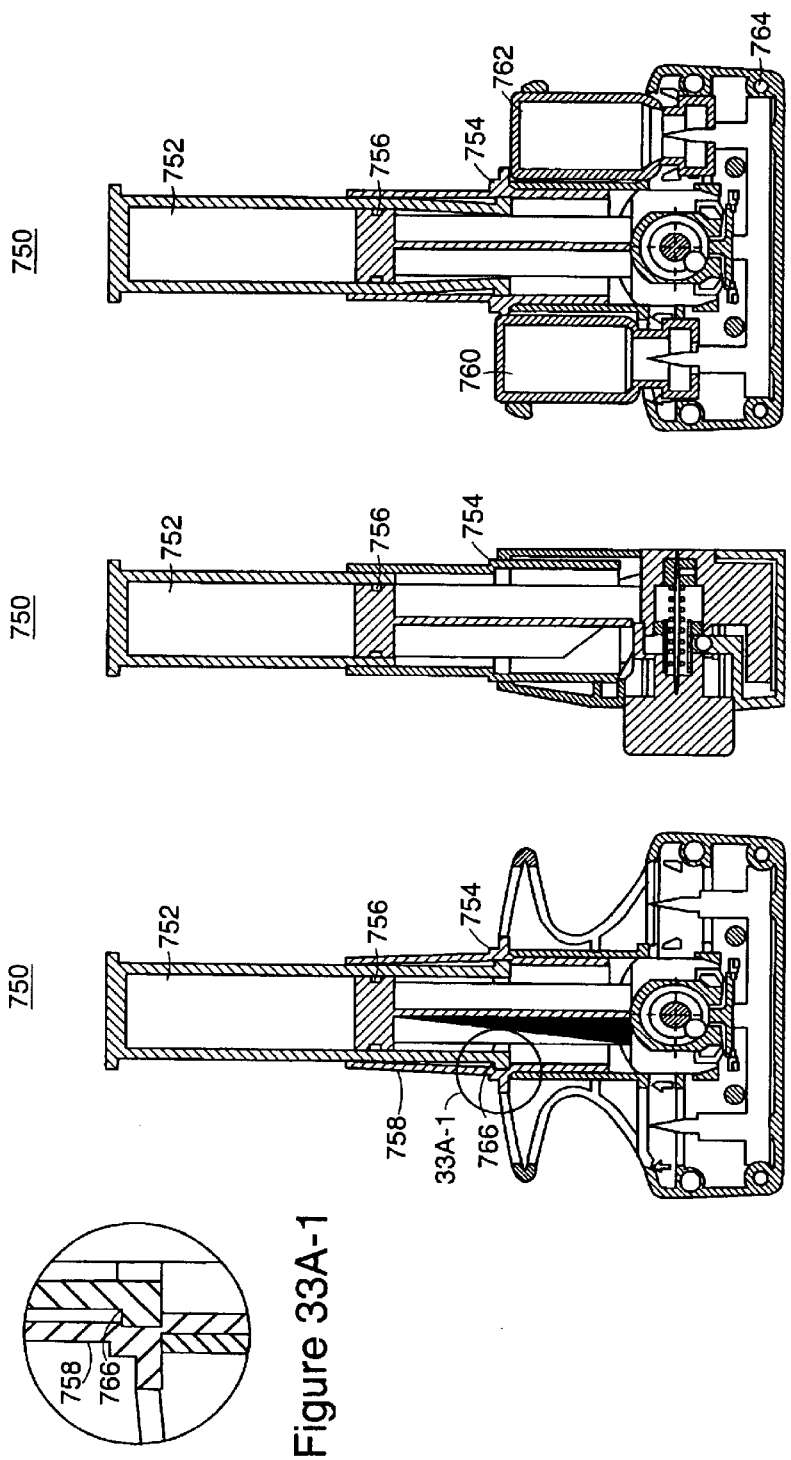

DEVICE FOR MEASURING A VOLUME OF DRUG

RELATED APPLICATIONS

This application is a Continuation-in-Part of, and claims priority under 35 U.S.C. §120 to, U.S. patent application Ser. No. 09/439,879, entitled DRUG DELIVERY SYSTEMS AND METHODS, filed on Nov. 12, 1999, which in turn claims priority under 35 U.S.C. §119(e) to U.S. Provisional A. S. No. 60/108,382, filed on Nov. 13, 1998 and to U.S. Provisional A. S. No. 60/131,644, filed on Apr. 29, 1999, and all of whose entire disclosures are incorporated by reference herein.

This also claims the benefit of prov. application No. 60/192,743 filed on Mar. 28, 2000.

BACKGROUND OF THE INVENTION

The present invention relates to the preparation and administration of a product and, more particularly, to the injection of the same into a living organism, for example, a human body. Previously, various devices have been developed for the percutaneous delivery of medications into living organisms including syringes in which a liquid is delivered from a chamber using pressure asserted by a manual plunger through a needle inserted under the skin.

Additionally, it is well known in the art that the storage life of certain injectable substances such as glucagon, used to dissolve blood clots, is increased when the substance is stored in a powdered or lyophilized state, for example. These lyophilized substances (i.e., drugs or compounds) are presently used for injection of materials that would otherwise be unstable. Lyophilization, for example, is the rapid freezing of a material at a very low temperature followed by rapid dehydration by sublimation in a high vacuum. The resulting lyophilized compound is typically stored in a glass vial or cartridge which is closed by a cap, such as a rubber stopper or septum.

It is necessary to reconstitute the powdered or solid material, such as a lyophilized compound, prior to administration. This is accomplished by mixing the solid compound with a suitable diluent or liquid. Reconstitution typically involves the use of a syringe with a needle to withdraw the diluent from a separate vial and inject it into the vial containing the compound. The compound is then thoroughly mixed, typically by shaking the vial by hand, and a separate syringe with a needle withdraws the desired amount to be injected into the patient. Because two separate containers are used, the person reconstituting the compound must be certain to mix the correct amounts such that a proper concentration of the mixture results. When a syringe is used to mix the diluent and drug, the exact volume of diluent to drug ratio is difficult to obtain. Thus, precise concentration levels of administered drug may be compromised.

Moreover, because the diluent and compound are in separate, sterilized containers, the manual withdrawal of diluent via a syringe and reinjection of the same into the container containing the solid material such as a powdered or lyophilized drug may compromise sterility, and safety due to the use of a syringe.

Because of increased use of powdered compounds or lyophilized drugs, for example, it is desirable to provide both professional and non-professional personnel with a reconstituted drug delivery system. It is desirable to have a simple, reliable system that facilitates preparation and safe delivery of an accurate dosage of a reconstituted compound.

In addition, it is desirable to provide a system that reconstitutes a lyophilized drug while maintaining sterility throughout the process. Also, it is desirable to provide improvements in the percutaneous delivery of medication generally, which provide for safe, effective administration by the user.

SUMMARY OF THE INVENTION

The present invention relates to systems and methods for delivering liquid drugs to a user. The drug delivery system can include delivery of reconstituted powdered drugs such as, for example, lyophilized drugs, or more generally for the transfer and delivery of liquid drugs. Powdered or lyophilized drug delivery further includes a system to reconstitute the powdered drug.

The drug delivery systems may further include a pressurization system which pressurizes the drug for transfer to a delivery system or for direct subcutaneous delivery.

Further, the drug delivery system in accordance with the present invention includes an injector system which contacts the tissue and delivers the drug to the patient or user. In the alternative, the drug delivery system in accordance with the present invention includes filling of detachable delivery devices, for example, a standard syringe, a needleless injector, an infusion device or different types of pumps. Another example uses a pen injector which aspirates the liquid drug from the system and in turn delivers the drug subcutaneously.

The methods for delivering a powdered drug such as a lyophilized drug include the steps of pressurizing a diluent solution in a diluent vial. The pressurizing systems may include, but are not limited to, a compressed air supply, a chemical gas generator, a collapsible volume supply, a bellow canister, a standard syringe or a cylinder, for example. The methods further include the step of delivering the pressurized diluent solution to the powdered drug vial. The next step in the method includes the reconstitution of the drug to form a liquid drug by mixing the powdered drug with the diluent solution. The methods further include the steps of providing the liquid drug to an injector system or transferring the liquid drug to detachable delivery devices. The following step includes the injection of the liquid drug into the tissue of the patient or user. The methods further include the steps of moving the injection needle from a delivery or injection position to a retracted or storage position once delivery is complete. It should be noted that, depending on the application or delivery of different medicaments, the features of the drug delivery systems may vary. For example, the pressurization level can vary depending upon the viscosity level of the medicament, and the needle type or length can vary depending upon subcutaneous injection or intermuscular injection. For example, for subcutaneous injections, the needle length ranges from 5 to 12 mm while the needle length may vary up to about 3 cm for intermuscular injections.

The methods for delivering a liquid medicament to a patient include the steps of pressurizing the liquid drug solution in the vial with a pressurizing system. The subsequent steps are similar to the steps described with respect to the methods for delivering a powdered medicament.

A preferred embodiment of the present invention features an injector system having an angled or unshaped needle.

Another preferred embodiment of the present invention features an injector system having a straight needle.

Yet another preferred embodiment of the present invention employs a transfer system for transferring the drug to delivery devices such as, for example, a standard syringe with a needle or a needleless pen injector. The devices receive the liquid drug from a container, such as a vial containing the liquid drug. The delivery devices subsequently deliver the medication to the user's tissue as described herein.

Another preferred embodiment of the present invention features a combination system having the ability to reconstitute drug into solution and subsequently inject it into a user. In accordance with this embodiment the reconstituted drug delivery system has a housing having a first opening or port that receives a first container that contains a solid substance, such as a powdered lyophilized drug, for injection. It should be noted that the container is a rigid container, such as, for example, a vial or a cartridge containing the powdered drug. The housing can also include a second opening or port that receives a second container that contains a fluid to be mixed with material in the first container, to form an injectable fluid. The drug delivery system may include a manifold having a first channel that provides fluid communication between the first and second containers. The manifold further includes a second channel between the first container and a delivery or transfer device. The manifold can also include a communication channel to a pressurization system which provides the driving pressure to deliver the liquid drug. In a preferred embodiment, the penetrating member is a needle, in fluid communication with the first container after the needle moves between a storage position in the housing to an injection position extending outside the housing and into the user.

A preferred embodiment of the invention provides for concealment of the injection needle within the main housing of the drug delivery device except during the injection of the drug to the user. This embodiment can include a needle retraction device for withdrawing the needle into the housing after injection to minimize the risk of exposure to a contaminated needle.

In accordance with other aspects of the present invention, the length of the delivery path from the container with the injectable fluid to the injection needle is reduced to minimize loss of residual amount of liquid drug.

According to another aspect of the invention, the injection needle first pierces the skin of the person being injected and is concurrently placed in fluid communication with the first container that contains the injectable fluid.

According to yet another aspect of the invention, the container that contains the injectable fluid is substantially visible during reconstitution and injection such that the user can visually observe the process. A compressed fluid, such as a gas in the container with the injectable fluid, is used to force the injectable liquid through the injection needle and into the tissue being injected. In an alternative embodiment, the device has a single port with a compression element such that a container with a liquid medication, such as a previously reconstituted material, can be inserted into the housing and simultaneously pressurized to the needed pressure to deliver the correct dose over a predetermined time period.

In a preferred embodiment of the system, the device is used with the injectable fluid container being vertically oriented during injection. To reduce the risk of injecting any gas into the injection site, a gas impermeable membrane such as a hydrophilic membrane is disposed in the fluid path, which in a wetted state minimizes or preferably prevents gas flow while allowing liquid to flow through the membrane. The rigid containers need to be in a vertical orientation during reconstitution for appropriate pressurization. In an embodiment including a cartridge having diluent and air, a vertical orientation is not required for reconstitution.

According to a further aspect of the present invention, the axis of the injection needle is perpendicular to the longitudinal axis of the container with the injectable fluid. In a preferred embodiment, the containers containing a powdered or lyophilized drug and diluent are inserted in the housing in the same direction along parallel axes. In another embodiment, the containers are inserted along a common axis or parallel axes in the opposite direction. The system can have housing apertures, ports, or openings that have a size compatible with standard vial and cartridge sizes such that existing vials and/or cartridges can be used. The container contents do not have to be mixed until immediately prior to injection. Because the contents of the containers are only in contact with other sterile parts, sterility prior to and during the reconstitution process is maintained.

According to another aspect of the present invention a further improvement to reduce and preferably prevent the risk of injecting gas into the injection site, includes the use of a drug which is gas impermeable once wetted. Further, since the gas impermeable membrane can sustain pressure, the delivery time for the liquid drugs is shortened as a higher driving force is generated using pressurization systems. By disposing such a membrane such as a hydrophilic membrane in the drug delivery path that is gas impermeable in a wetted state, gas needed to control injection pressure and duration can be added in the system as the membrane checks the delivery of gas to the user. The container containing the fluid can be a changeable volume container which contains a controllable volume of a gas, for example, air. This controllable volume of air and/or fluid are forced into the drug container, resulting in a drug under pressure to deliver the correct dose over a selected time period. According to a further aspect of the invention, the device includes a manifold system to minimize the drug delivery path and simplify assembly costs, and increase system reliability. The simplicity and flexibility of the manifold system facilitates the use of standard prefilled cartridges and syringes. In a preferred embodiment, the manifold is a two-piece polycarbonate molding in which the two molded elements are ultrasonically welded together. The gas impermeable membrane is attached or welded to one piece of the polycarbonate molding.

According to another aspect of the present invention, a further improvement to deliver an accurate predicted volume of a drug includes adjustable height penetrating members, such as, for example, outlet spikes. In the alternative, delivery of an accurate predicted volume, for example 50% or 80% etc., can be gauged from the residual drug volume or the use of detachable delivery devices, for example, a standard syringe or a pen-type pump injector.

According to another aspect of the present invention, a further improvement to the drug delivery systems includes interlocks and indicators which ensure the safe and accurate delivery of the drugs. The interlocks include, but are not limited to latches which provide for a desired sequence of operation such as pressurization of containers to follow the step of insertion of the containers, or prevention of displacement of the needle to an injection position after a first injection use. The indicators include a vertical orientation indicator and end of delivery indicators.

According to another aspect of the present invention, the housing of the drug delivery device is shaped and designed to function appropriately to enable single handed operation. For example, the bottom surface of the housing is flat in shape to allow table top placement to accommodate single handed operation by the user. Further, the device is sized to enable the insertion of vials and subsequent activation of the device using one hand.

In a preferred embodiment, the system housing is lightweight and compact, having a weight of less than 30 grams and a volume of less than 100 cm$^3$. This provides a portable disposable device that can be discarded or recycled after a single use and that is readily transported by the user. In addition, the present invention is self-contained and maintains sterility throughout the reconstitution and injection of a fluid such as a lyophilized drug. It should be noted, the weight and volume of the system housing can vary depending upon the different embodiments and the volume of drug being delivered to a user.

A further embodiment of the present invention includes a device for controlling a volume of liquid drug. The device includes a first chamber containing liquid drug, a pressure source, a liquid drug volume measurement chamber in liquid communication with the first chamber, and a liquid drug volume measurement assembly. The device may be used in connection with any number of other devices for dispensing or delivering liquid drug into a mammal, such as the lyophilized system, the injection system or the transfer system described above. The device is also contemplated to be used in connection with other devices and systems such as infusion pumps, or the like where finite measurement of the liquid drug volume is needed prior to the delivery of the drug. In addition—position independent within injecting period

BRIEF DESCRIPTION OF THE DRAWINGS

FIGS. 5A–5C are perspective views of a preferred embodiment of a drug delivery device in accordance with the present invention.

FIGS. 6A–6C illustrate the operation of a drug delivery device substantially similar to the device shown in FIGS. 5A–5C.

FIGS. 8A–8F illustrate the operation of a drug delivery device substantially similar to the device shown in FIGS. 5A–5C.

FIGS. 9A–9F illustrate the operation of a preferred embodiment of a drug delivery device in accordance with the present invention.

FIGS. 11A–11D illustrate cutaway views of an alternative embodiment including a drug container subassembly of the drug delivery device in accordance with the present invention.

FIGS. 13A and 13B illustrate cutaway views of an alternate embodiment of the drug delivery device in accordance with the present invention.

FIG. 14 illustrates a cutaway view of another preferred embodiment of the drug delivery device in accordance with the present invention.

FIGS. 17A–17C illustrate cutaway views of an alternate embodiment of the drug delivery device in accordance with the present invention.

FIGS. 18A–18C illustrate cutaway views of an alternate embodiment of the injector system of the drug delivery system in accordance with the present invention.

FIGS. 20A–20C illustrate views of an alternate embodiment of the drug delivery system in accordance with the present invention which uses standard vials containing a liquid medicament.

FIGS. 28A–28C illustrate cutaway views of the operation of a preferred embodiment of a drug delivery system in accordance with the present invention.

FIGS. 33A–33I are cutaway views illustrating the interlocks built into the drug delivery system in accordance with the present invention.

Figure 1A:
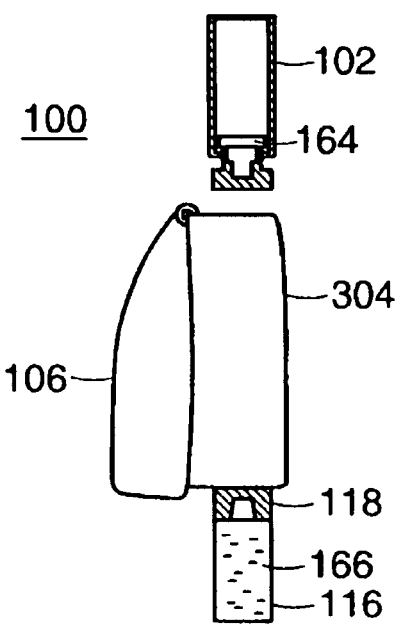
FIGS. 1A–1F illustrate the operation of a preferred embodiment of a drug delivery device in accordance with the present invention.
Figure 1B:
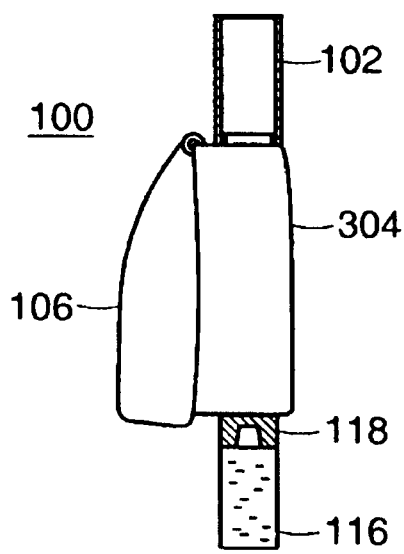
Figure 1C:
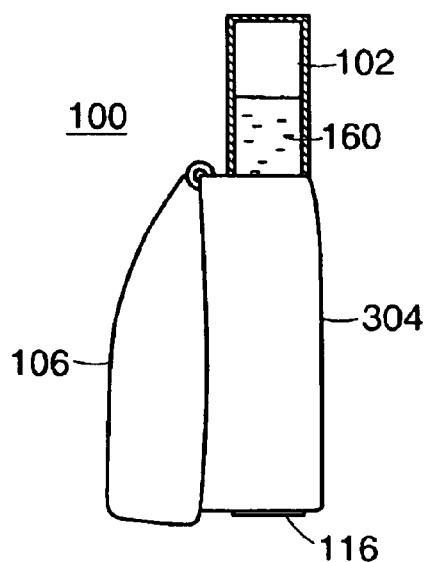

The foregoing and other objects, features, and advantages of the drug delivery systems and methods will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention is directed to drug delivery systems and methods. The drug delivery system provides generally for the delivery of a drug in solution under pressure, and more particularly to the injection of powdered or lyophilized drugs that require reconstitution. The drug delivery system includes a reconstitution system, a pressurization system to facilitate drug delivery, a transfer system and an injector system. Different embodiments of the present invention may use only one of the systems described and other embodiments can employ combination of these systems, depending on the requirements of different applications. For example, a preferred embodiment can deliver a liquid drug and not require reconstitution.

Therefore the drug delivery systems and methods are a combination of some or all of the systems or processes described below.

With reference to FIGS. 1A–1E, the general operation of a preferred embodiment of a drug delivery device 100 is illustrated. FIGS. 2A–2B, and 3A–3D provide sectional views of the same embodiment for clarity. As specifically illustrated in FIG. 1A, drug delivery device 100 comprises a first member or housing 304 and a pivotally connected second member or handle 106. The device 100 is used to mix, within a sterilized environment, a first liquid such as a diluent 166 (for example, a fluid such as sterilized water) with a second powdered drug such as a lyophilized drug or compound concentrate 164, e.g., interferon, and to inject the resulting reconstituted lyophilized drug into a living organism, which in the preferred embodiment is a human being. Advantageously, the device 100 utilizes a standard vial or first storage container 102, which contains the lyophilized drug or compound 164, and a standard cartridge or second storage container 116, which contains the diluent 166. The device 100 may be formed from inexpensive materials, such as plastic or the like, such that it is economically feasible to dispose of the device after a single injection.

In preparation for the administration of the drug, the user removes protective packaging which envelops the device 100. This packaging maintains sterility of the device 100 prior to use. In the preferred embodiment of the invention, cartridge 116 containing diluent 166 comes preassembled, being locked into the bottom of housing 304 by the arms 133 as shown in FIGS. 2A and 2B.

Figure 1D:
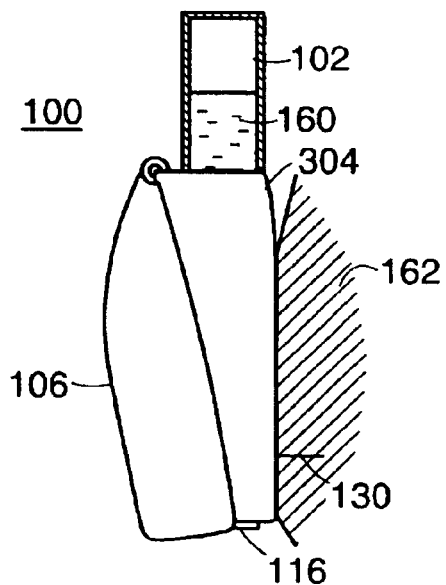
Figure 2A:
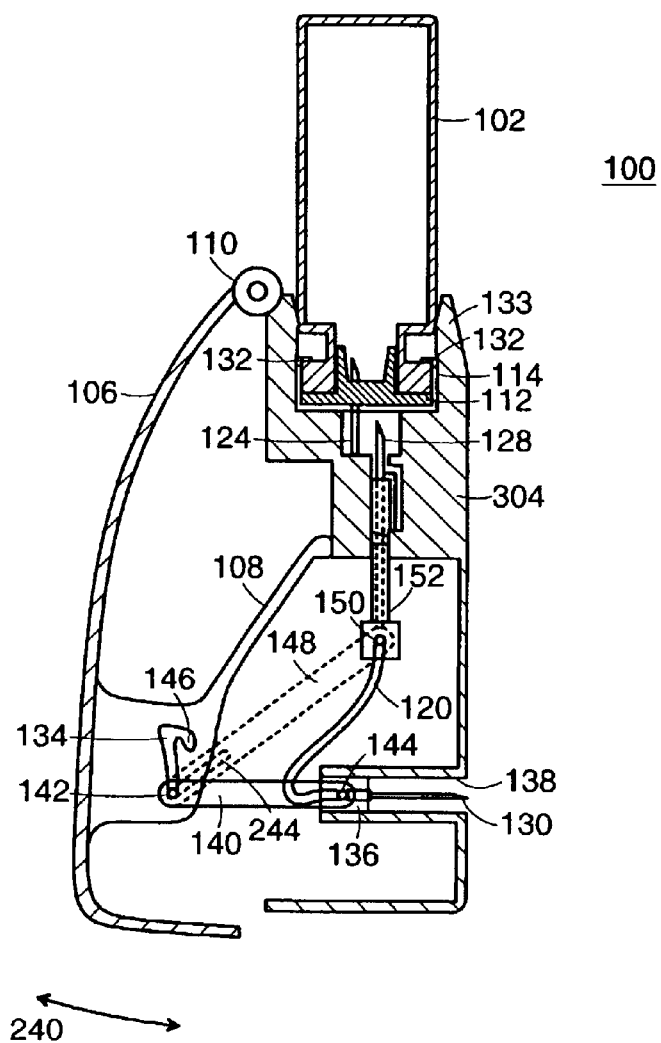
FIGS. 2A and 2B illustrate cutaway views of the drug delivery device shown in FIGS. 1A–1F, along line 2A, 2B-2A, 2B in FIG. 1F.
Figure 2B:
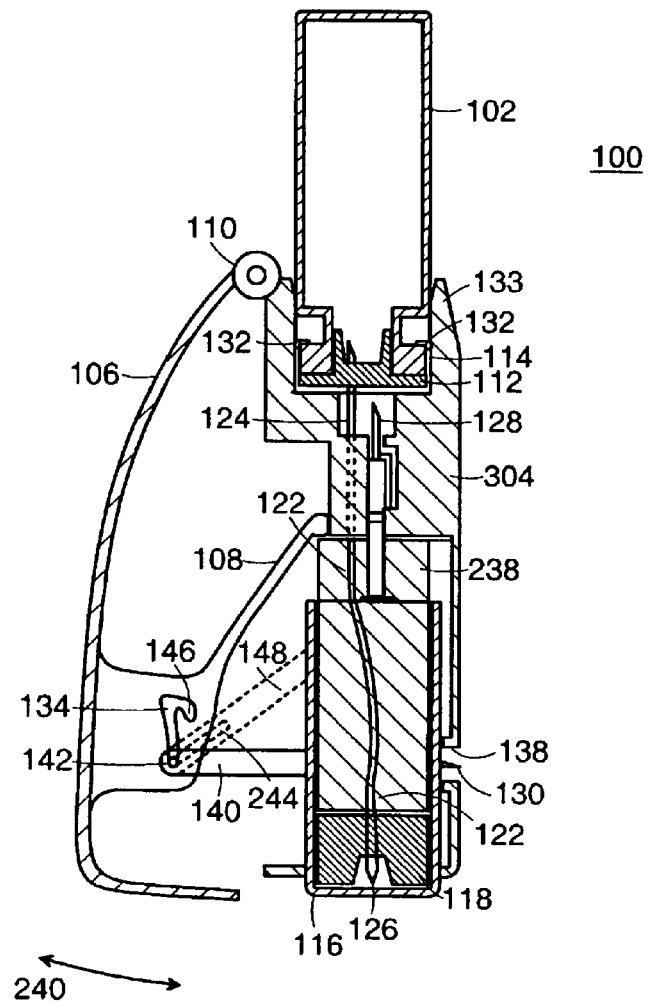
Figure 3A:
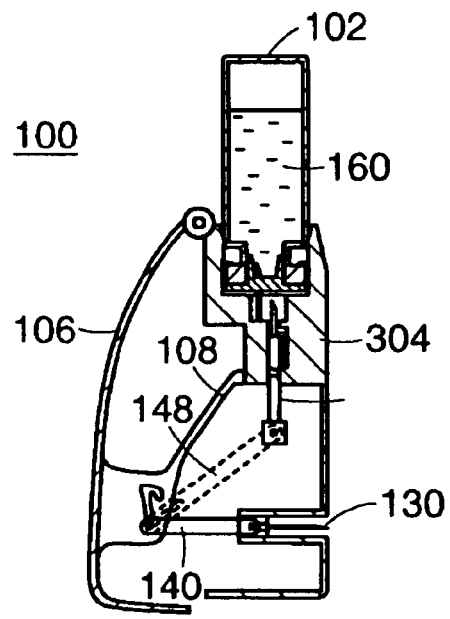
FIGS. 3A–3D illustrate the sectional views of the internal components of the drug delivery device of FIGS. 1A–1E and FIG. 2 during administration of the reconstituted drug.

The sterility protector of the vial 102 is removed and then locked into the top of housing 304 as shown in FIG. 2A with a needle 124 from the housing penetrating a stopper 112 of the vial. At this stage, vial 102 is filled with air at ambient pressure. The cartridge 116 is pushed upward, i.e., toward vial 102. The cartridge 116 is punctured and the diluent 166 is delivered to the vial 102 as shown in part in FIG. 1C. At this stage, as will be explained below, there is a fluid such as gas in vial 102 which is compressed by transfer of diluent 166 into vial 102. The user swills the device 100 to ensure the lyophilized drug is appropriately reconstituted. The reconstituted lyophilized drug, or injectable fluid, is identified as reference number 160. Now, drug in solution with the diluent is ready for injection. The device 100 is pressed against the skin of the person to be injected with the vial 102 in a vertical orientation to ensure that the compressed gas, for example, air is used to inject the reconstituted drug and that the gas or air is not injected into the injection site. The user presses the handle 106 which causes the injection needle 130 to move between a first position, or storage position, within the housing 304 as shown in FIG. 3A, and a second position, or injection position, outside the housing as shown in FIG. 3C. It is preferred that the needle extend out of the housing 304 in the range of 5 to 12 millimeters. The second extended position of the injection needle 130 is also illustrated in FIG. 1D. At this point, the injection needle 130 is fluidly connected to vial 102 such that the reconstituted lyophilized drug 160, under pressure from the compressed gas in vial 102, is delivered to the injection site. The delivery of the reconstituted lyophilized drug 160 can be completed in a time period in the range of 10–30 seconds.

Upon release of handle 106, a biasing mechanism 108 (to be detailed below) returns the handle to the original position. Simultaneously, a needle retraction mechanism (also to be described below) locks the injection needle 130 within the housing 304, thereby reducing and preferably preventing exposure of the contaminated needle. The final stage of operation is illustrated in FIG. 1E, wherein the device 100 may be safely discarded.

Figure 1E:
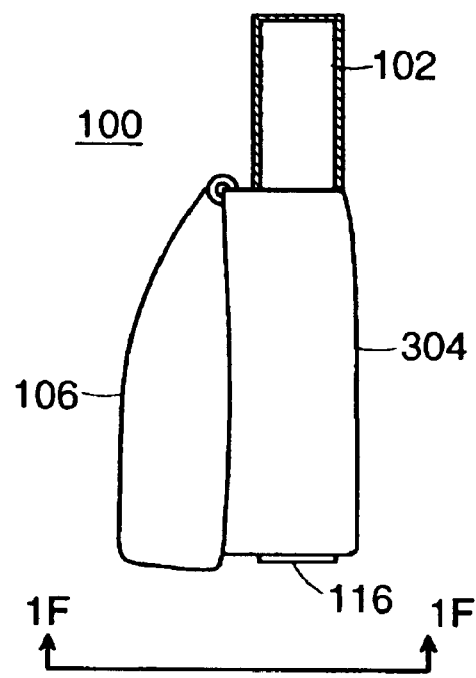
Figure 1F:
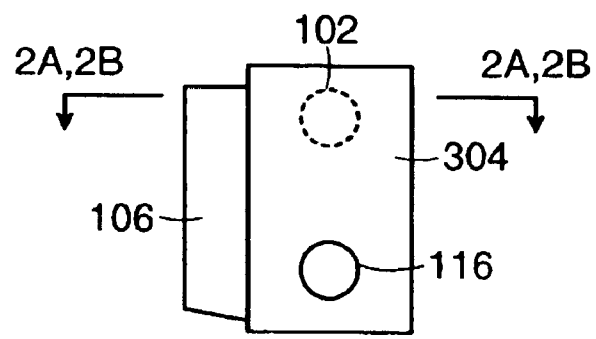

FIG. 1F is a view taken along line 1F—1F of FIG. 1E and illustrates the relative positions of vial 102 and cartridge 116 in housing 304. As shown, the longitudinal axes of vial 102 and cartridge 116 are parallel but offset relative to the positioning within the housing 304. This allows for both vial 102 and cartridge 116 to be inserted into the housing 304 without interfering with the internal components of the device 100, for example, the needle retraction mechanism described below.

FIGS. 2A and 2B illustrate cutaway views along lines 2A, 2B-2A, 2B of FIG. 1F of the device 100 including vial 102 and cartridge 116. More particularly, vial 102 is preferably a standard vial, for example, a 2 milliliter vial, which typically comprises glass and includes a puncturable rubber stopper 112 held in place by an aluminum band or other sealing mechanism 114. The upper end of housing 304 includes a grooved portion 132 which locks the vial 102 to the housing by passing the lip of the aluminum band 114 under a pair of spaced apart arms that hook up into the housing. A first needle 124, or other suitable means, is mounted to the housing 304 and is configured to pierce the rubber stopper 112 of vial 102 upon insertion of the vial into the locking position provided by arms 133. First needle 124 is fluidly connected to a first channel or tube 122 for receiving the diluent from cartridge 116 as illustrated in FIG. 2B.

Cartridge 116, similar to vial 102, preferably comprises a standard cartridge (for example, a 2 milliliter cartridge with about 1 milliliter diluent) and includes a rubber stopper 118 which is pierced by a second needle 126, or other suitable means. Second needle 126 is fixedly mounted on an extending member or compression element 238 of housing 304 such that the cartridge is pierced upon insertion of the cartridge. First tube 122 is fluidly connected to the second needle 126. Upon insertion of the cartridge 116, extending member 238 or compression element of housing 304 contacts and pushes rubber stopper 118 toward the bottom of cartridge 116. In this manner, the diluent 166 is forced up tube 122 into vial 102 to mix with the drug 164 contained therein. In the preferred embodiment of the present invention, cartridge 116 contains approximately 1 milliliter of diluent which is forced into vial 102, resulting in a pressure inside vial 102 of approximately 2.25 bars. This pressure can be adjusted, for example, by decreasing the amount of diluent or air in cartridge 116. A higher pressure inside vial 102 injects the reconstituted drug 160 more quickly.

Thus, a sterilized solution is provided wherein the diluent 166 is mixed with the lyophilized drug 164 with minimal exposure to outside contaminants. It is preferable that vial 102 containing the reconstituted lyophilized drug 160 be visible during reconstitution and injection such that the user can properly visually verify that the lyophilized drug 160 is thoroughly mixed with diluent 166 and that the vial 102 is vertical during injection to ensure the compressed gas is not being injected into the injection site.

Handle member 106 is pivotally connected to the housing 304 at a first end by a pivoting mechanism 110 which can include a rivet or other suitable means such that the handle member rotates in the direction of arrow 240. Handle member 106 includes biasing mechanism 108 which resiliently biases handle member such that the end opposite the pivotally connected end is forced away from housing 304. Biasing mechanism 108 includes an extending member from handle member 106 which contacts housing 304, thereby providing a resilient biasing force away from the housing when the handle member is forced toward the housing. Alternatively, or additionally the biasing mechanism 108 can comprise a conventional spring, or other suitable means, interposed between housing 304 and handle member 106 which provides the biasing force.

Also shown in FIG. 2A is a needle injection and retraction mechanism for injecting the reconstituted drug 160 into the person and retracting the injection needle 130 within the housing 304. The mechanism includes a first bar member 140, which is pivotally connected at a first end by member 136, and guidably mounted at a second end to the handle member 106 by a first coupling device 142, such as a pin, rivet, bolt, or other suitable means. Member 136 fixedly supports injection needle 130 and is guided by an opening 138, or needle aperture, in the housing 304. In the preferred embodiment of the invention, injection needle 130 is in the range of a 24–28 gauge needle. The movement of first coupling device 142 is controlled by a J-shaped slot 134 which can comprise a slot or groove in handle member 106. A second bar member 148 is pivotally connected at a first end to first coupling device 142 and pivotally connected at a second end to a third bar member 152 by a third coupling device 150. Third bar member 152 fixedly supports a third needle 128 and may be guided by internal bore in housing 304. A second channel or tube 120 fluidly connects the third needle 128 and injection needle 130. It is preferable to minimize the length of tube 120 such that the residual volume of drug remaining in the tube after injection is reduced to increase the accuracy of the dosage.

The operation of drug delivery device 100 shown in FIGS. 2A and 2B is illustrated in FIGS. 3A–3D. FIG. 3A illustrates the stage at which the cartridge 116 is inserted forcing diluent 166 up tube 122 into vial 102. It will be recalled that the rubber stopper of 118 of cartridge 116 is forced to the bottom of the cartridge by member 238 as shown in FIGS. 2A and 2B. This causes the diluent 166 to be forced up tube 122 which results in the reconstituted drug 160 being under pressure, which in the preferred embodiment is approximately 2.25 bars. The device 100 is preferably vigorously shaken to ensure the lyophilized drug is properly mixed with diluent 166.

Figure 3B:
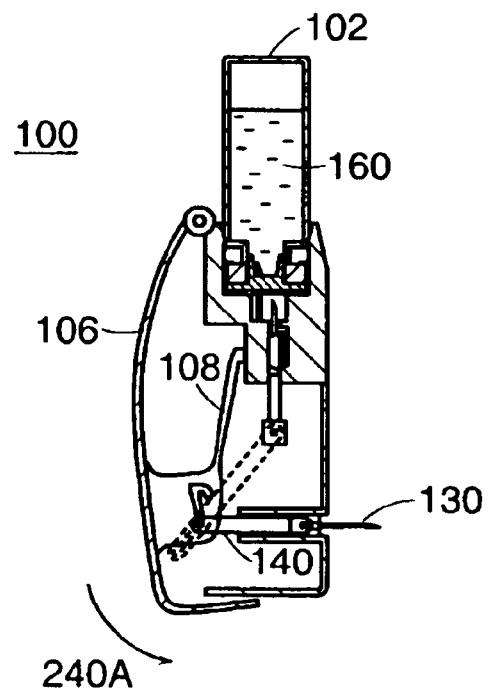
Figure 3C:
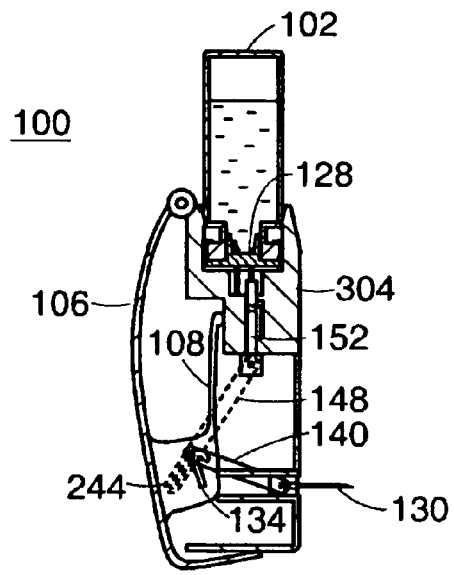

In FIG. 3B, the device 100 is placed against the skin of the person being injected. The user presses handle member 106 toward the housing 304 in a direction shown by arrow 240A, thereby displacing injection needle 130 from the first position within the housing to a second position outside the housing such that the needle penetrates the skin of the body being injected.

As shown in FIG. 3C, continued pressure of the handle 106 towards the housing 304 causes the first bar member 140 to ride up the J-shaped slot 134. Simultaneously, second bar member 148, which includes a linear slot 244, is rotated such that first coupling device 142 rides up to the top of slot 244.

Figure 3D:
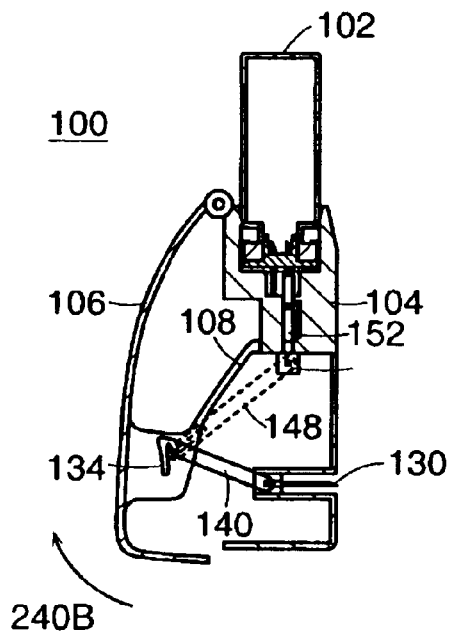

FIG. 3D illustrates the continued pressing motion of the handle member 106 toward the housing 304. As the handle member 106 continues to pivot, the second bar member 148 forces third bar member 152 and hence third needle 128 upward such that third needle penetrates the rubber stopper 112 of vial 102. Because the reconstituted lyophilized drug 160 is under pressure, it is forced through tube 120 and thus into the person being injected. At this point, biasing mechanism 108 is compressed. As the handle member 106 is released, biasing mechanism 108 forces the handle member away from the housing 304 as indicated by arrow 240B and thus withdraws injection needle within the housing. This is illustrated in FIG. 3D.

J-shaped slot 134 is beneficially provided with an end locking portion 146 which catches coupling device 142 such that the injection needle 130 is "locked" within the housing 304 after a single injection. Now, the device 100 can be safely discarded.

Figure 4A:
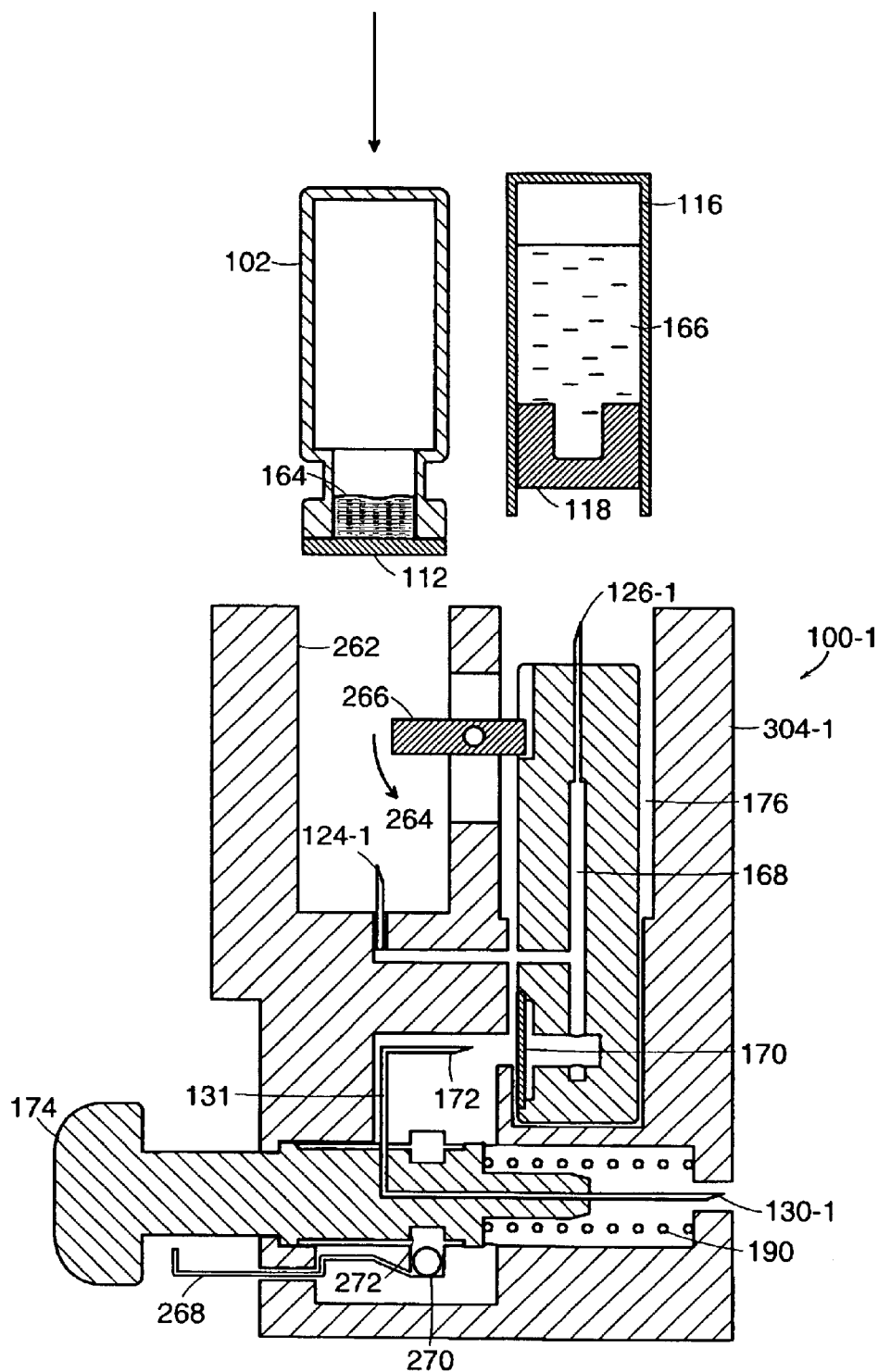
FIGS. 4A–4O illustrate the operation of a preferred embodiment of a drug delivery device in accordance with the present invention.
Figure 4B:
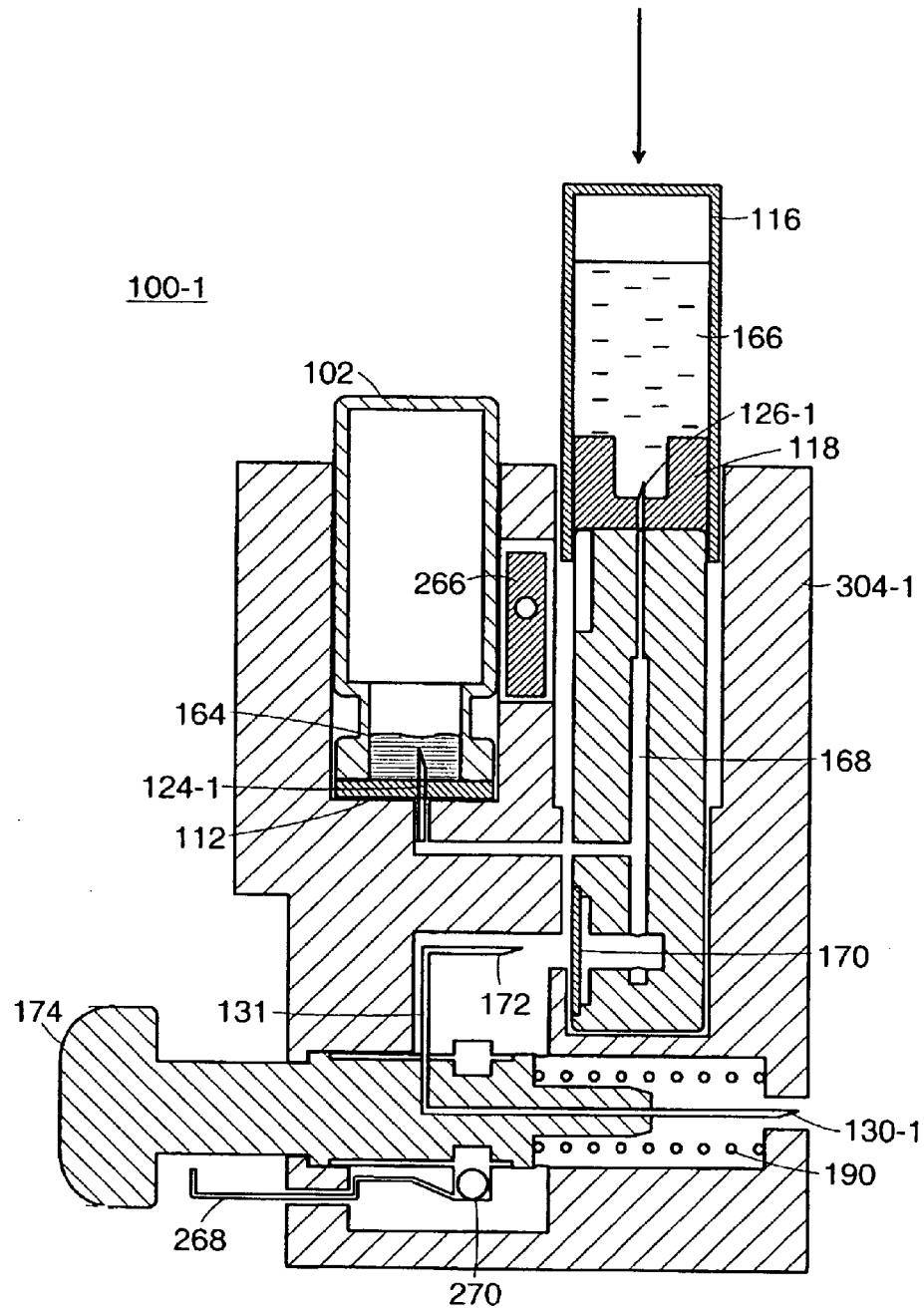

FIGS. 4A–4K illustrate a drug delivery device 100-1 in accordance with a preferred embodiment of the present invention wherein the same reference numbers refer to the same or similar elements. More particularly, FIG. 4A illustrates the device 100-1 which includes a housing 304-1 having a first port or opening 176 for receiving a diluent cartridge 116 and a second port or opening 262 for receiving vial 102. In this embodiment, it is preferred that cartridge 116 containing diluent 166 be preassembled such that the cartridge is partially penetrated by needle 126-1 and such that the device 100-1 (without vial 102) is wrapped by a packaging material to maintain sterility prior to use. Again, it is preferable to use a standard 2 milliliter vial and cartridge that contains 1 milliliter of diluent. Thus, the user unwraps the packaging material and places vial 102 containing the lyophilized drug 164 into the opening 262. Alternatively, vial 102 and cartridge 116 are packaged separately from the device 100-1 as shown in FIG. 4A. The user removes the sterility protector and presses the vial 102 firmly into the opening until needle 124-1 penetrates the rubber stopper 112. The user then forces cartridge 116 into the housing 304-1. As cartridge 116 is forced into the housing 304-1, the rubber stopper 118 is first penetrated by needle 126-1 such that the needle extends into the diluent 166. This stage is illustrated in FIG. 4B.

Continuing to insert the cartridge 116 into the housing 304-1 forces the rubber stopper 118 to the bottom of the cartridge, as shown in FIG. 4C. That is to say, the first opening 176 of housing 304-1 is preferably circular, thereby allowing the walls of cartridge 116 to enter the housing and not the rubber stopper 118. This forces the diluent 166 through needle 126-1 to a manifold or communication passageway 168 and into the vial 102. Again, the resulting reconstituted lyophilized drug 160 in vial 102 is preferably under pressure of about 2.25 bars. A greater or lower pressure may be necessary depending on the volume to be injected. The device 100-1 is preferably vigorously shaken to ensure the reconstituted lyophilized drug 160 is properly mixed in preparation for injection.

It is preferable to insert vial 102 containing the lyophilized drug 102 before insertion of cartridge 116 containing diluent 166 such that the diluent is not spilled into opening 262. In order to ensure the proper insertion sequence of vial 102 and cartridge 116, an interlocking mechanism is provided in accordance with another aspect of the present invention. Interlocking mechanism comprises a bar member 266 pivotally connected to the housing 304-1 between the openings 176 and 262. The bar member is configured to be moved in the direction of arrow 264 (FIG. 4A) upon insertion of vial 102. Thus, as shown in FIG. 4A, bar member 266 prevents cartridge 116 from being inserted. As vial 102 is inserted, it rotates bar member 266 in the direction of arrow 264 as shown in FIG. 4A such that cartridge 116 can subsequently be inserted.

As shown in FIG. 4B, the device 100-1 is further provided with an actuator or pushing member 174 for displacing the injection needle 130-1 between a first position within the housing 304-1 and a second position outside the housing. It is preferred that the injection needle 130-1 extend out of the housing 304-1 in the range of 5–12 millimeters. The injection needle 130-1 is in the range of a 24–28 gauge needle and is preferably a "U" type needle having a second end 172 configured to puncture sealing member 170. Sealing member 170, which can be any puncturable material such as butyl rubber, sealingly maintains the liquid in the upper part of housing 304-1 prior to use.

It is preferable to prevent displacement of the injection needle 130 when the device 100-1 is not properly oriented, for example, upside down, in order to prevent the compressed gas in vial 102 from being injected. Also, it is preferable to lock the injection needle 130-1 within the housing 304-1 after a single injection to reduce exposure to the contaminated needle. Additionally, it is preferable to only allow displacement of needle 130-1 after insertion of cartridge 116. Accordingly, a locking assembly 268A is provided to accomplish the foregoing.

Figure 4G:
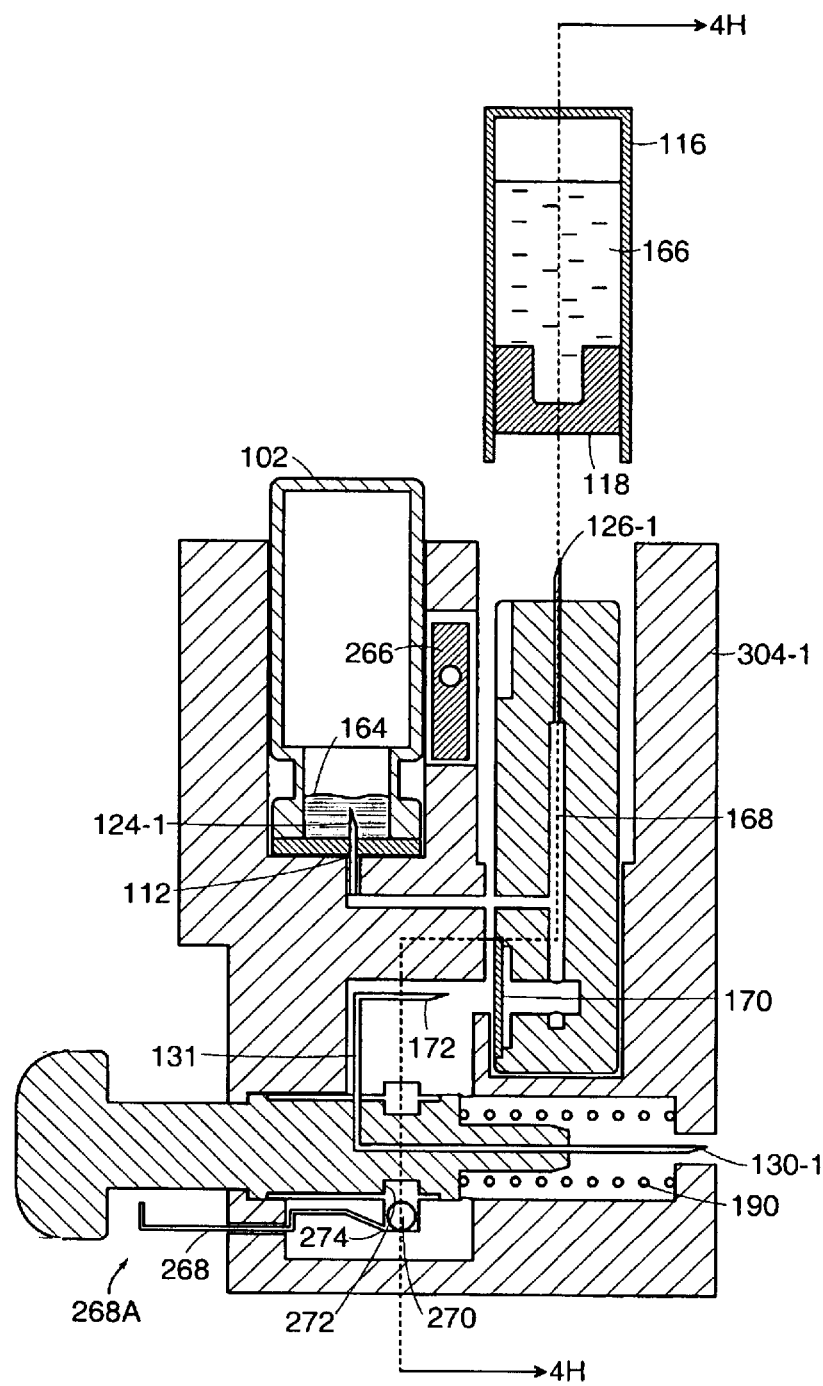
Figure 4H:
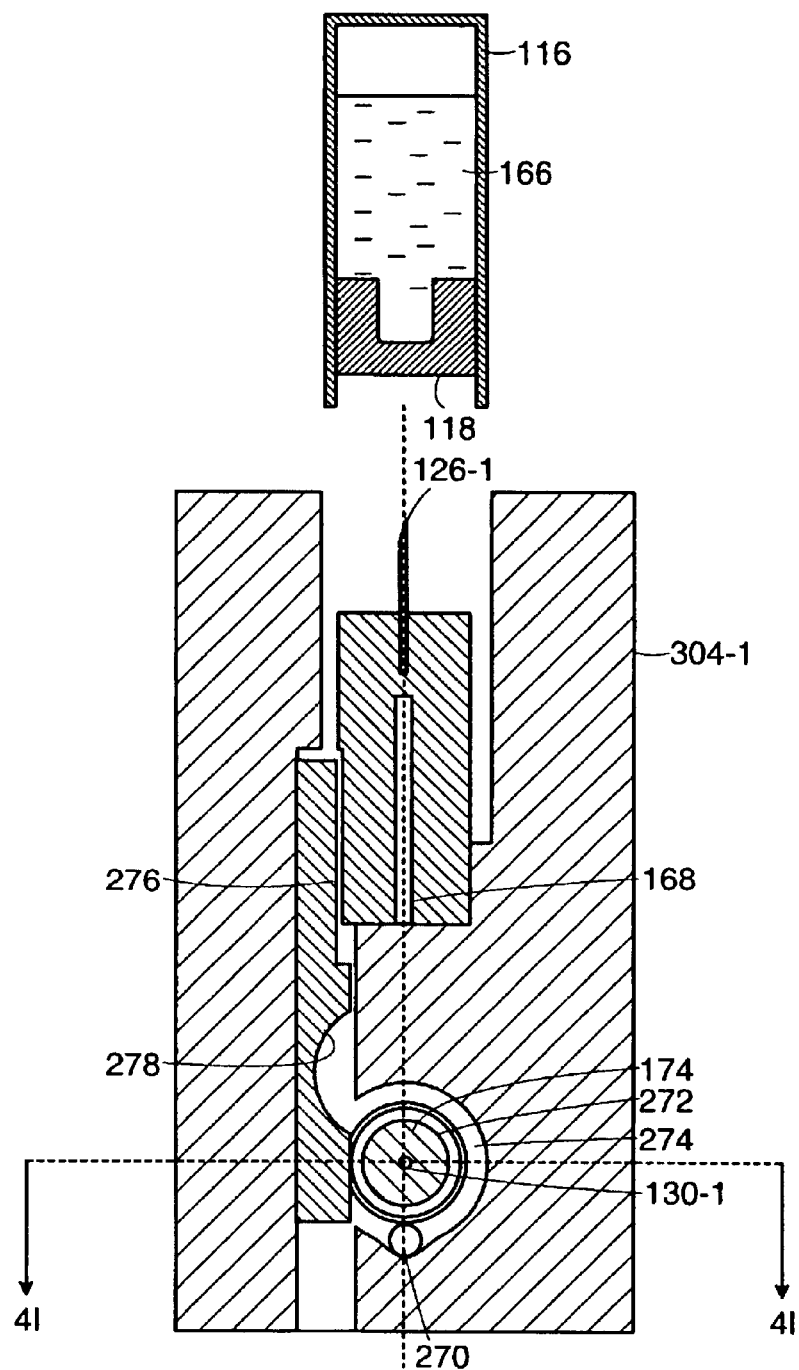

The locking assembly 268A comprises member 268 as shown in FIG. 4C having a first end configured to be moved by pushing member 174 and a second end configured to displace a ball 270 or other appropriate movable locking device. With the pushing member 174 in the first position such that injection needle 130 is within the housing, groove 272 of the pushing member 174 aligns with groove 274 such that ball 270 can freely travel around the groove 274 of the pushing member. When vial 102 is vertically oriented with the compressed gas above the liquid, thus being properly positioned for injection as shown in FIGS. 4B and 4C, ball 270 rests in the bottom of groove 274 allowing the pushing member 174 to displace the injection needle 130. If the vial 102 is not properly positioned (for example, the assembly being upside down such that compressed gas would be injected, as shown in FIGS. 4E and 4F), the ball 270 is positioned within grooves 272 and 274 to prevent displacement of the pushing member 174. The locking assembly 268A can be further configured to allow displacement of the pushing member 174 only after cartridge 116 is inserted. FIGS. 4G–4L illustrate this aspect of the invention. More particularly, FIG. 4G is similar to FIG. 4C except cartridge 116 is shown outside of the housing 304-1. FIG. 4H is a sectional view taken along line 4H—4H of FIG. 4G and shows member 276 of the locking mechanism having a slotted portion 278 therein.

Figure 4I:
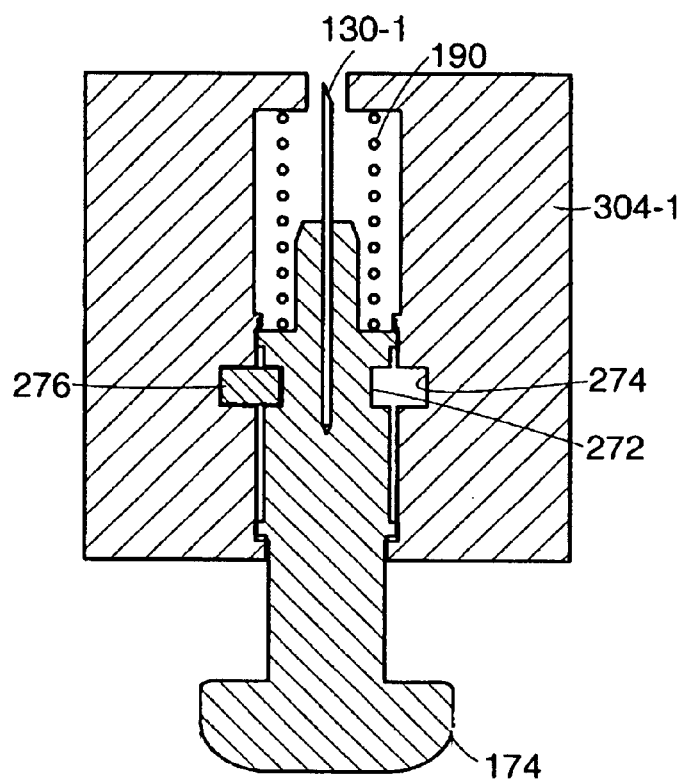

Member 276 is slidable within the housing 304-1 and configured to be moved by insertion of cartridge 116. The lower end of member 276 is positioned within grooves 272 and 274 as shown in FIG. 4I. Thus, with member 276 in the position shown in FIG. 4H, or before cartridge 116 is inserted into the housing 304-1, the pushing member 174, and hence injection needle 130-1, is prevented from moving to the injection position.

Figure 4L:
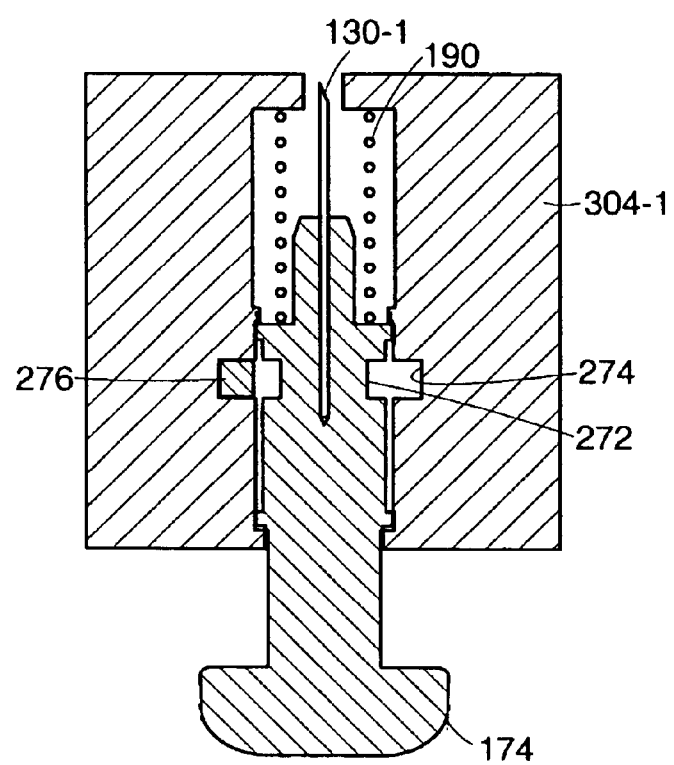

When the cartridge 116 is fully inserted into housing 304-1 as shown in FIG. 4J, member 276 is moved downward as shown in FIG. 4K. As shown in FIG. 4L, this allows slotted portion 278 to align such that pushing member 174 and hence injection needle 130-1 can be moved to the injection position.

Figure 4M:
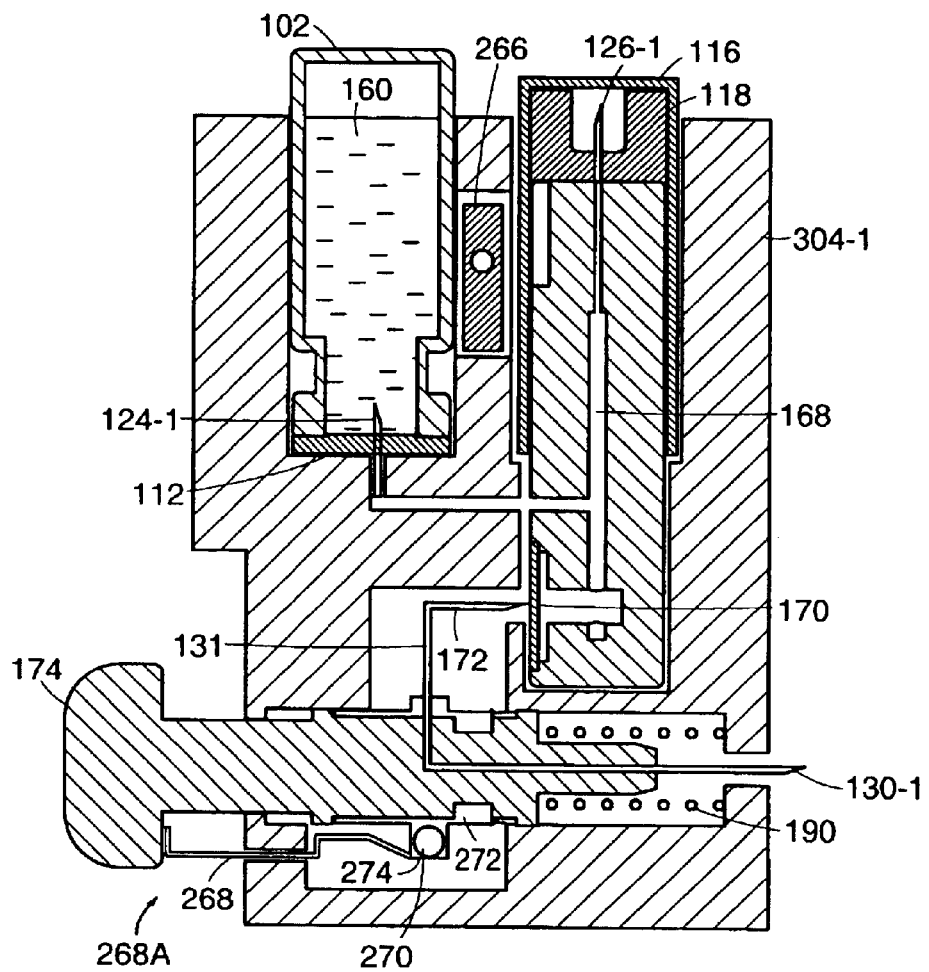
Figure 4N:
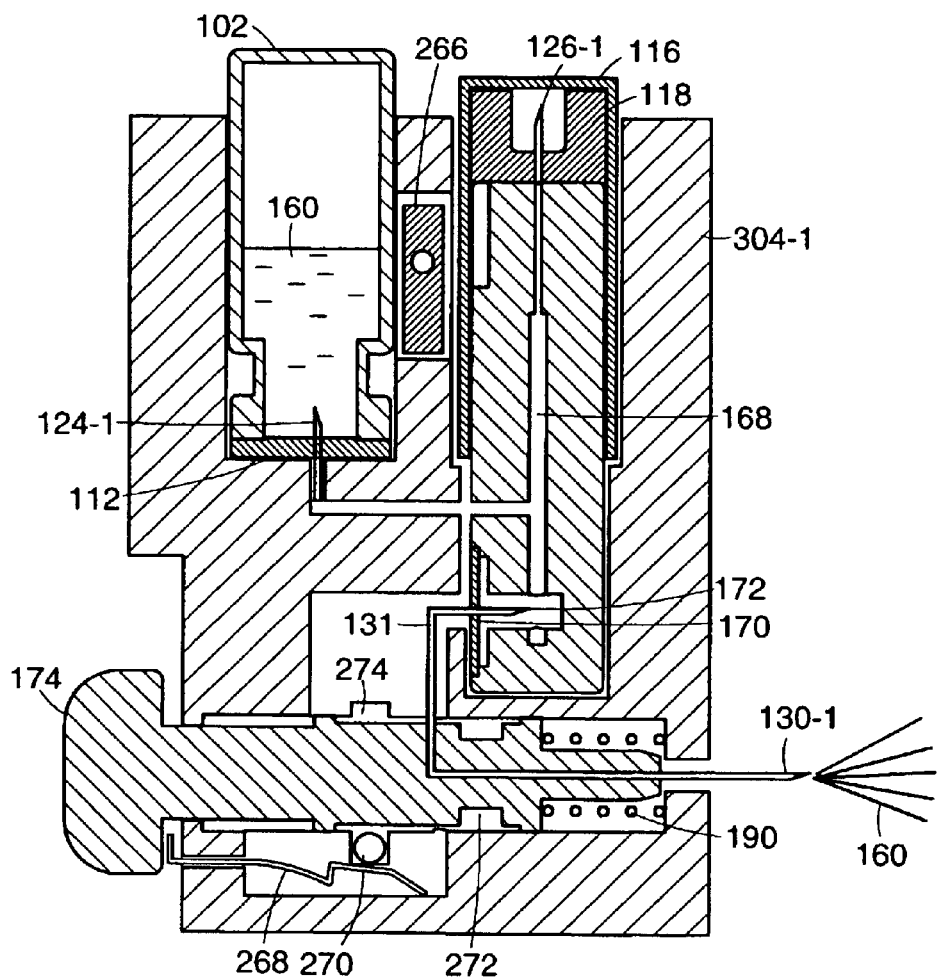
Figure 4O:
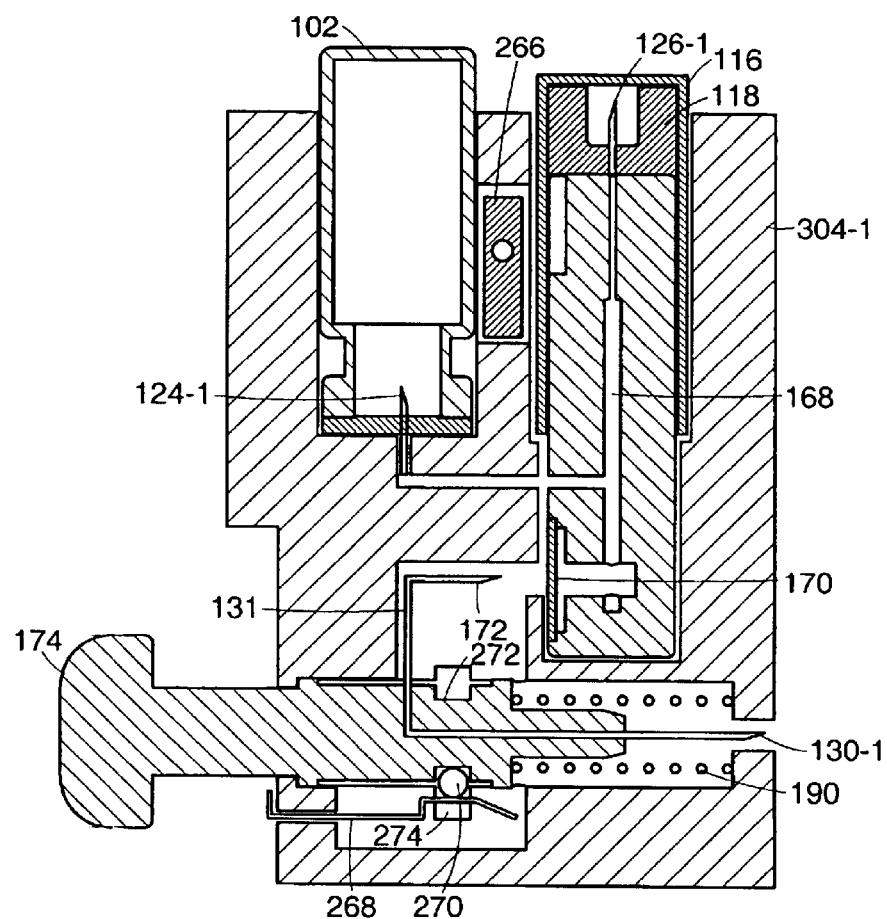

With the device 100-1 properly held by the user such that vial 102 is vertically oriented as shown in FIG. 4M, the user presses pushing member 174 such that the injection needle 130-1 first extends out of the housing 304-1, thus penetrating the skin of the person being injected. Continued pressing of pushing member 174 causes the second end 172 of injection needle 130-3 to puncture sealing member 170, thereby allowing the pressurized reconstituted lyophilized drug 166 to travel from vial 102 into the person being injected. It may take in the range of 10–30 seconds to deliver the injection fluid. This pressing motion compresses spring 190 such that upon release of pushing member 174, the member returns to the original position, i.e., the needle 130-1 is withdrawn within the housing 304-1 and locked therein. Insertion of the pushing member 174 into the housing 304-1 also moves in member 268 such that ball 270 is biased against the pushing member. This is shown in FIG. 4N. When the pushing member 174 is returned to the first position, the ball 270 is positioned and held within groove 272 by member 268, thereby preventing displacement of the pushing member and hence the injection needle 130-1 after a single injection. This configuration is illustrated in FIG. 4O. With the injection needle 130-1 locked within the housing 304-1, the device 100-1 may be safely discarded.

FIGS. 5A–5C illustrate a drug delivery device 100-2 in accordance with a preferred embodiment of the present invention. More particularly, FIG. 5A illustrates the device 100-2 with the cartridge 116 installed but not inserted or penetrated by any needle, and the vial 102 in place ready to be inserted. FIG. 5B illustrates the inserted vial 102, while FIG. 5C shows the subsequently inserted cartridge 116. At this stage, the diluent from cartridge 116 has been transferred to vial 102, resulting in a pressurized liquid in the vial. The device 100-2 is vigorously shaken to ensure proper mixing of the reconstituted lyophilized drug. The device 100-2 is now ready for injection. It should be noted that the housing 304-2 advantageously includes a cutaway portion 254 which allows the user to visually inspect vial 102 to verify that the lyophilized drug 160 is thoroughly mixed with diluent 166 and to verify that vial 102 is vertically oriented during injection to ensure air is not being injected into the injection site.

FIGS. 6A–6C are plan views of a similar device 100-3 corresponding to FIGS. 5A–5C, respectively. Accordingly, FIG. 6A illustrates the cartridge 116 installed but not punctured by needle 126-3. Vial 102, containing the lyophilized drug 164, is also shown ready to be inserted into housing 304-3.

FIG. 6B shows the inserted vial 102 which is punctured by needle 124-3. Vial 102 pushes first against surface 178-3 of puncturing device 182-3 and pushes device 182-3 downward before being pierced by needle 124. Pushing puncturing device 182 downward sets a spring which (as will be explained in FIGS. 7A–7C) moves puncturing device upward such that needle 128-3 penetrates vial 102. Alternatively, the spring can be preloaded. As shown, needles 124-3 and 126-3 are fluidly connected by a manifold 127 comprising a channel 129 or tube. Upon insertion of cartridge 116, the rubber stopper is first pierced by needle 126, and as cartridge 116 is further inserted into the circular opening 176-3 of housing 304-3, the rubber stopper 118 is forced to the bottom of cartridge 118, thereby forcing the diluent 166 through the manifold 127 into vial 102. This also compresses the gas that was heretofore contained in the vial 102 to a pressure sufficient for injection. The resulting stage is shown in FIG. 6C. The device 100-3 is preferably vigorously shaken to ensure proper mixing of the lyophilized drug 164. Now, the device 100-3 is ready to inject the reconstituted drug solution 160 contained in the vial 102.

Figure 7A:
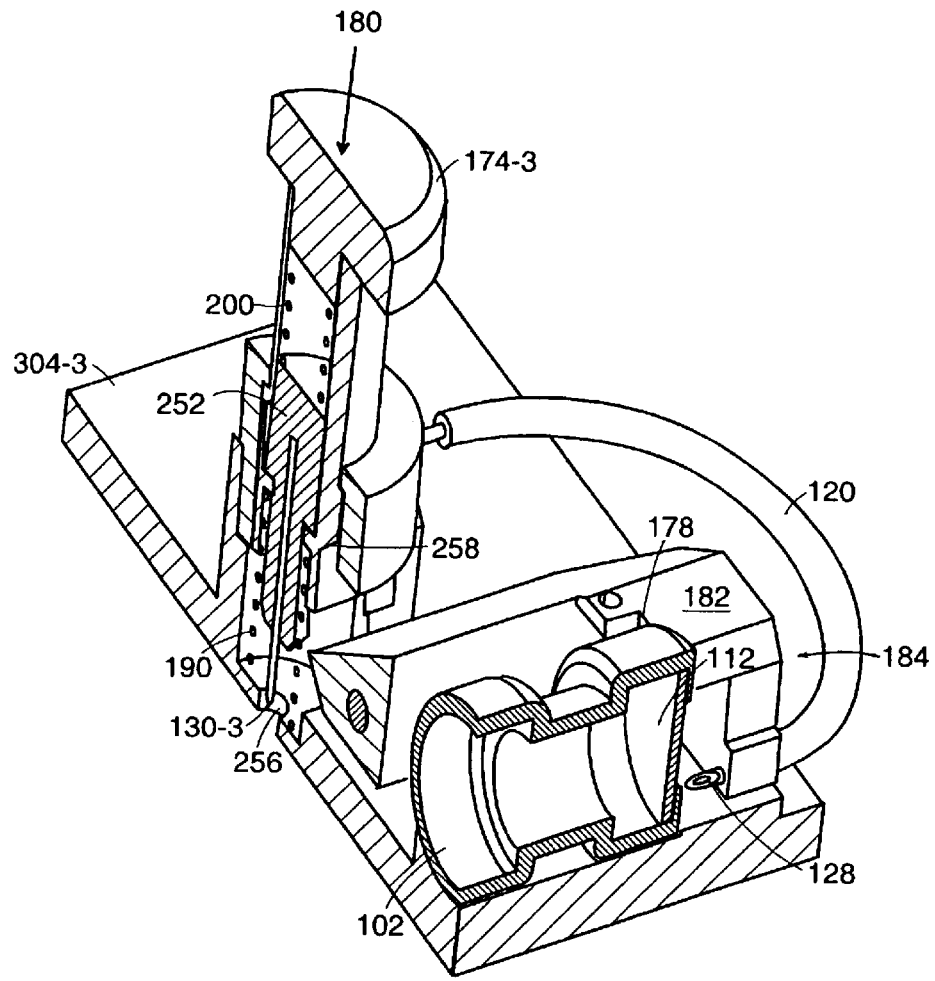
FIGS. 7A–7C are partial perspective views of the drug delivery device of FIGS. 5A–5C and 6A–6C illustrating the injection of the drug.
Figure 7B:
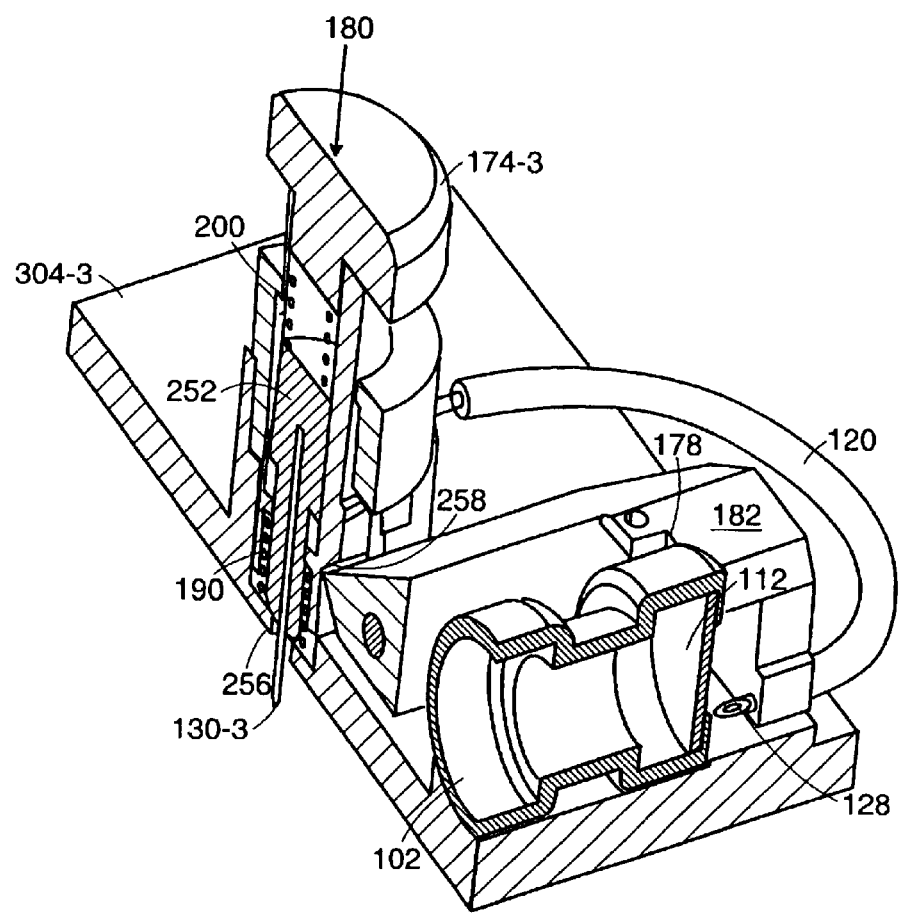
Figure 7C:
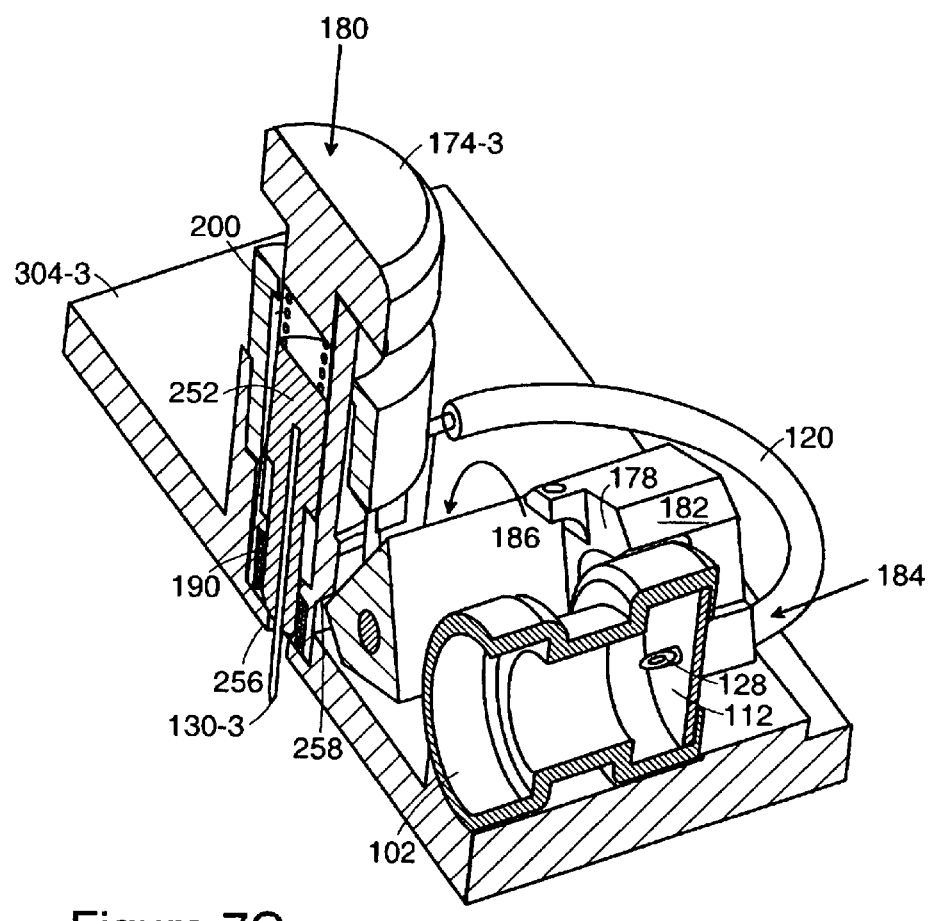

FIGS. 7A–7C illustrate partial perspective views of the device 100-2, 100-3 shown in FIGS. 5A–5C and 6A–6C. More particularly, FIG. 7A shows the pushing member 174-3 including an internal bore with member 252 slidably contained therein. Member 252 fixedly supports injection needle 130 which is in fluid communication with needle 128 via tube or channel 120. Needle 128 shown in FIG. 7A has yet to pierce the rubber stopper 112 of vial 102. Needle 128 is fixedly supported by puncturing device 182. As the pushing member 174-3 is pressed toward the housing 304-3 (i.e., in the direction of arrow 180), a first spring 190 is compressed allowing the member 252 to move downward until contacting the housing. This allows injection needle 130-3 to extend out of needle aperture 256 in housing 304-3 to penetrate the skin of the person being injected. The spring 190 is set such that it creates both axial and rotational movement. Only upon complete insertion of the vial 102 is the rotational movement of the spring enabled which in turn enables the puncturing of the vial 102. In the preferred embodiment, injection needle 130-3 extends in the range of 5–12 millimeters out of the housing through needle aperture 256. The injection needle 130 partially extending out of the housing 304-3 is illustrated in FIG. 7B.

As the pushing member 174 is further pressed toward housing 304-3, spring 200, which is stiffer than spring 190, is compressed allowing ridge 258 of pushing member 174-3 to contact puncture device 182. This causes rotation of puncturing device 182 in the direction of arrow 186 as shown in FIG. 7C, such that surface 178 no longer contacts the vial 102. The spring 190 which, as described above, was loaded upon insertion of vial 102, now causes the puncturing device 182 to rotate in the direction of arrow 184, thereby causing needle 128 to penetrate the rubber stopper 112 of vial 102. This arrangement is illustrated in FIG. 7C. The reconstituted drug 160 is forced by the compressed gas within vial 102 through injection needle 130 into the person being injected in a time range of approximately 10–30 seconds.

Figure 8B:
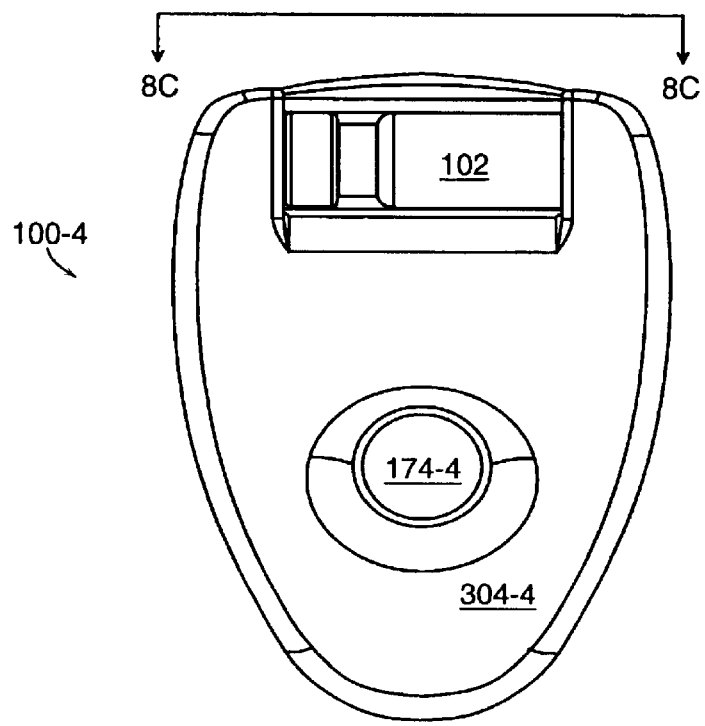

FIGS. 8A–8E illustrate a drug delivery system 100-4 in accordance with a preferred embodiment of the present invention wherein the same reference numbers refer to the same or similar elements. More particularly, FIG. 8A illustrates the device 100-4 which includes housing 304-4 having a first port or opening 176-4 for receiving cartridge 116 and a second port or opening 262-4 for receiving vial 102.

Vial 102 containing the reconstituted drug 164 is inserted into the housing 304, followed by the insertion of cartridge 116 containing the diluent 166. Again, a rubber stopper of the cartridge 116 is forced to the bottom of the cartridge which forces the diluent under pressure into vial 102. This stage is shown in FIG. 8B. Advantageously, the housing 304-4 includes a cutaway portion 400 such that vial 102 is substantially visible during reconstitution and injection. This allows the user to visually verify that the drug is properly reconstituted and that the vial 102 is vertically oriented during injection with the compressed gas above the reconstituted drug.

Figure 8C:
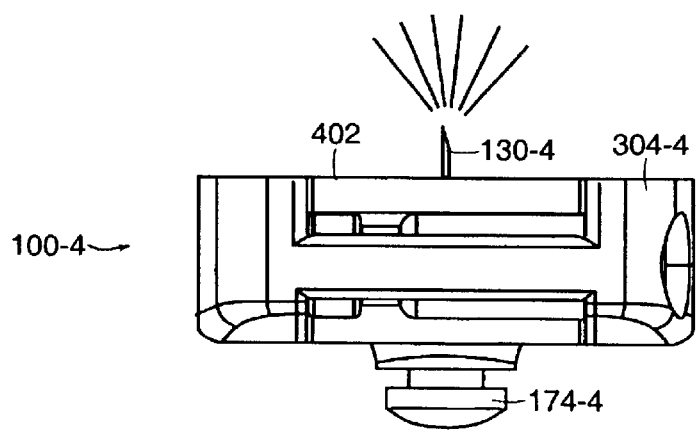
Figure 8D:
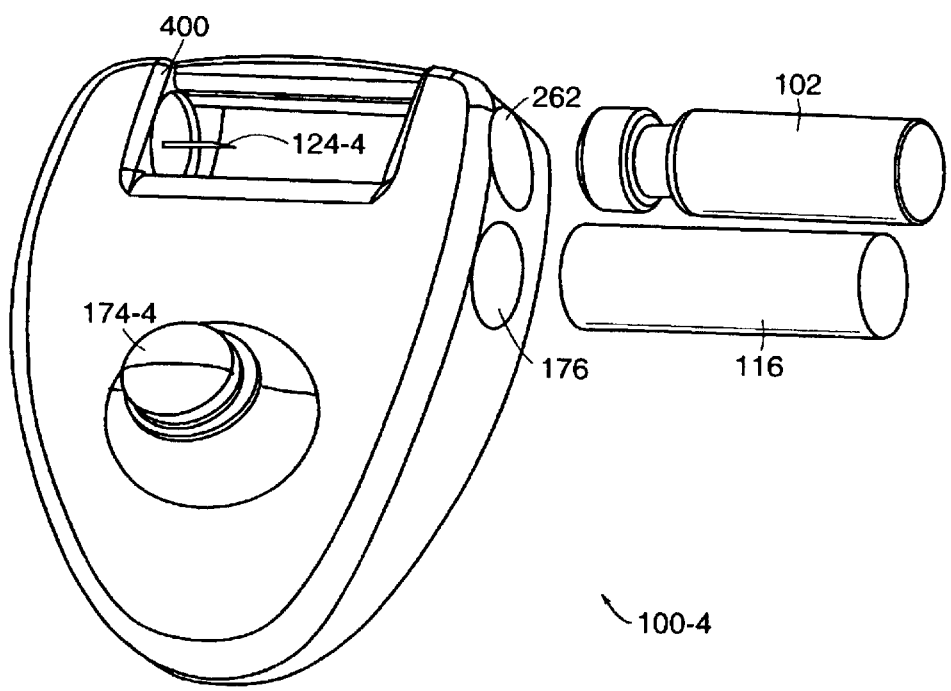
Figure 8E:
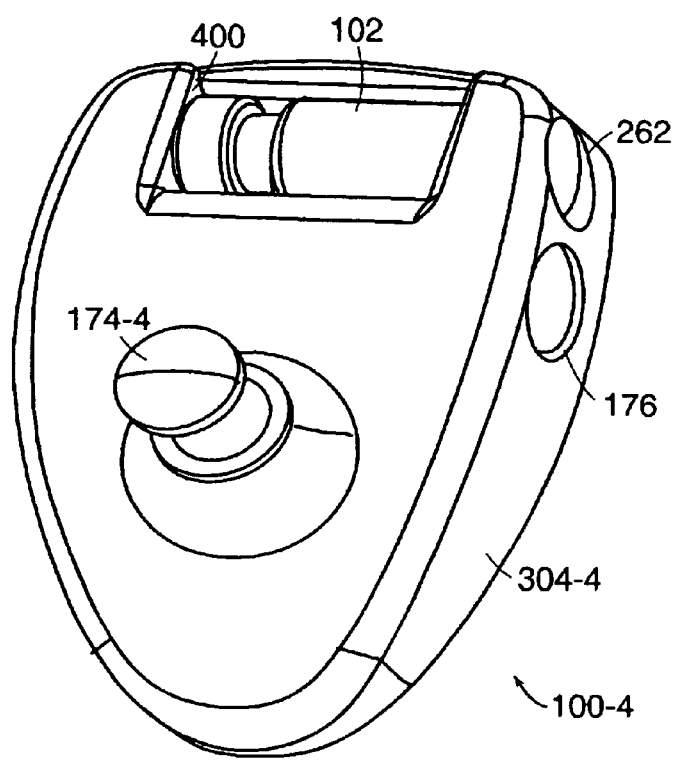
Figure 8F:
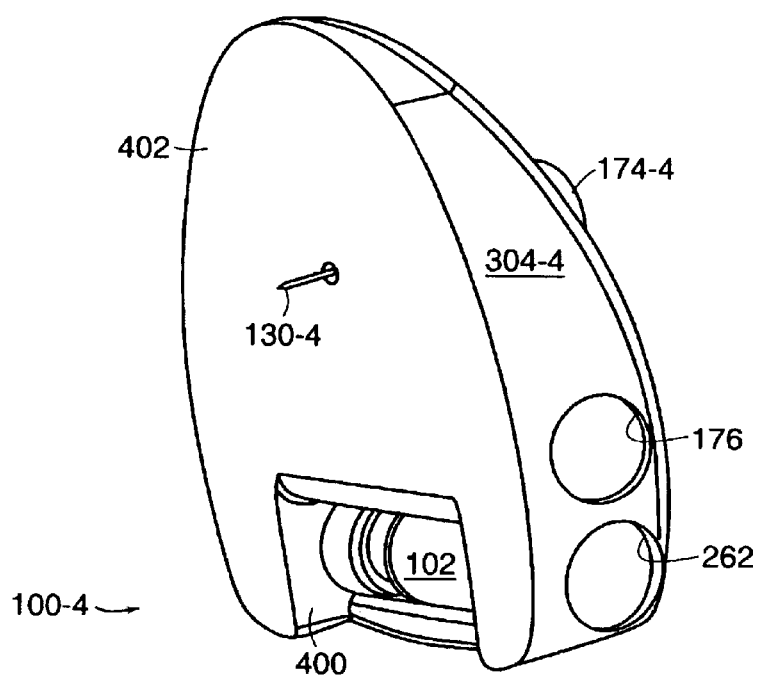

FIG. 8C is a rear view taken of FIG. 8B and illustrates the injection of the reconstituted drug. More particularly, the pushing member or actuator 174-4 is pressed into housing 304-4 which forces injection needle 130-4 out of the housing and into the person being injected. In the preferred embodiment, the injection needle extends out of the housing in the range of 5–12 millimeters. The reconstituted drug, in fluid communication with the vial 102, is transferred from the vial and into the person being injected. FIGS. 8D–8F are isometric views of the device 100-4 in the stages shown in FIGS. 8A–8C, respectively.

Figure 10A:
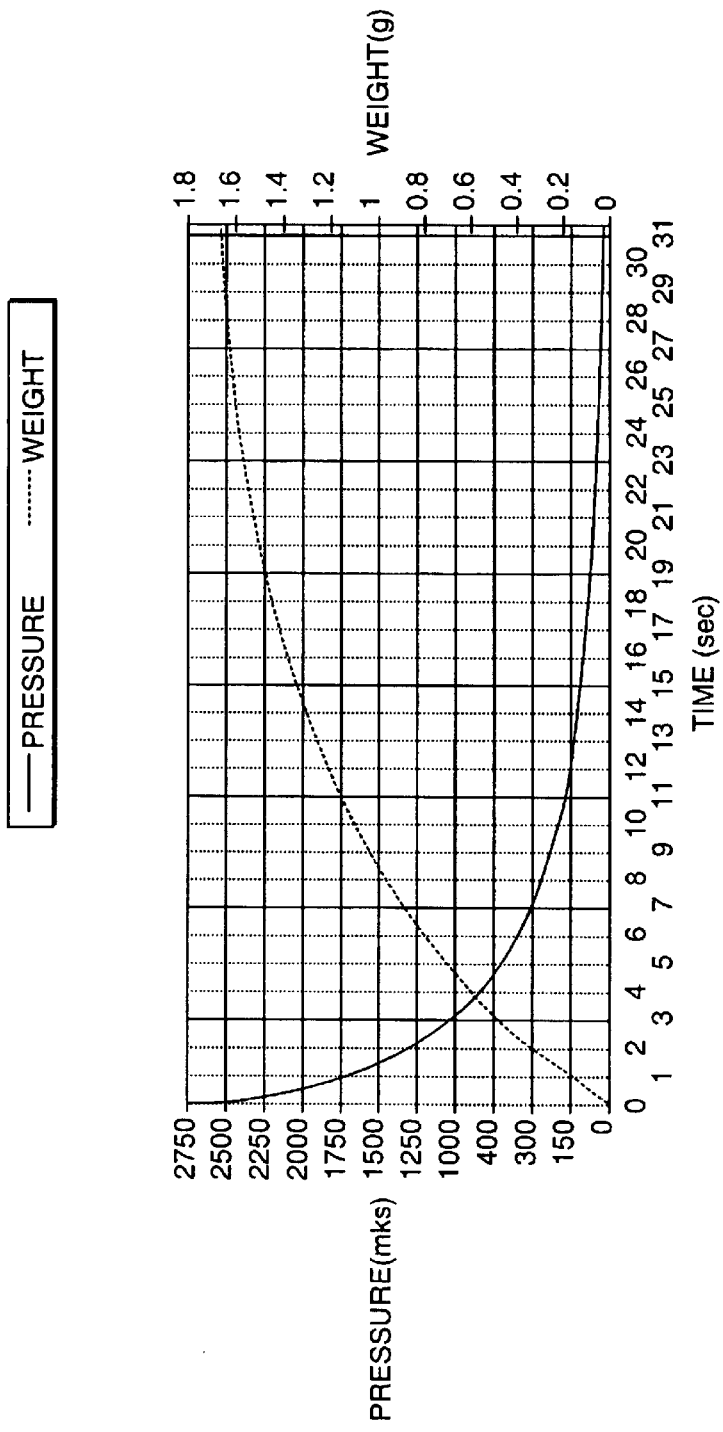
FIGS. 10A and 10B are graphical illustrations of the pressure, weight, and delivery characteristics of a preferred embodiment of the invention.
Figure 10B:
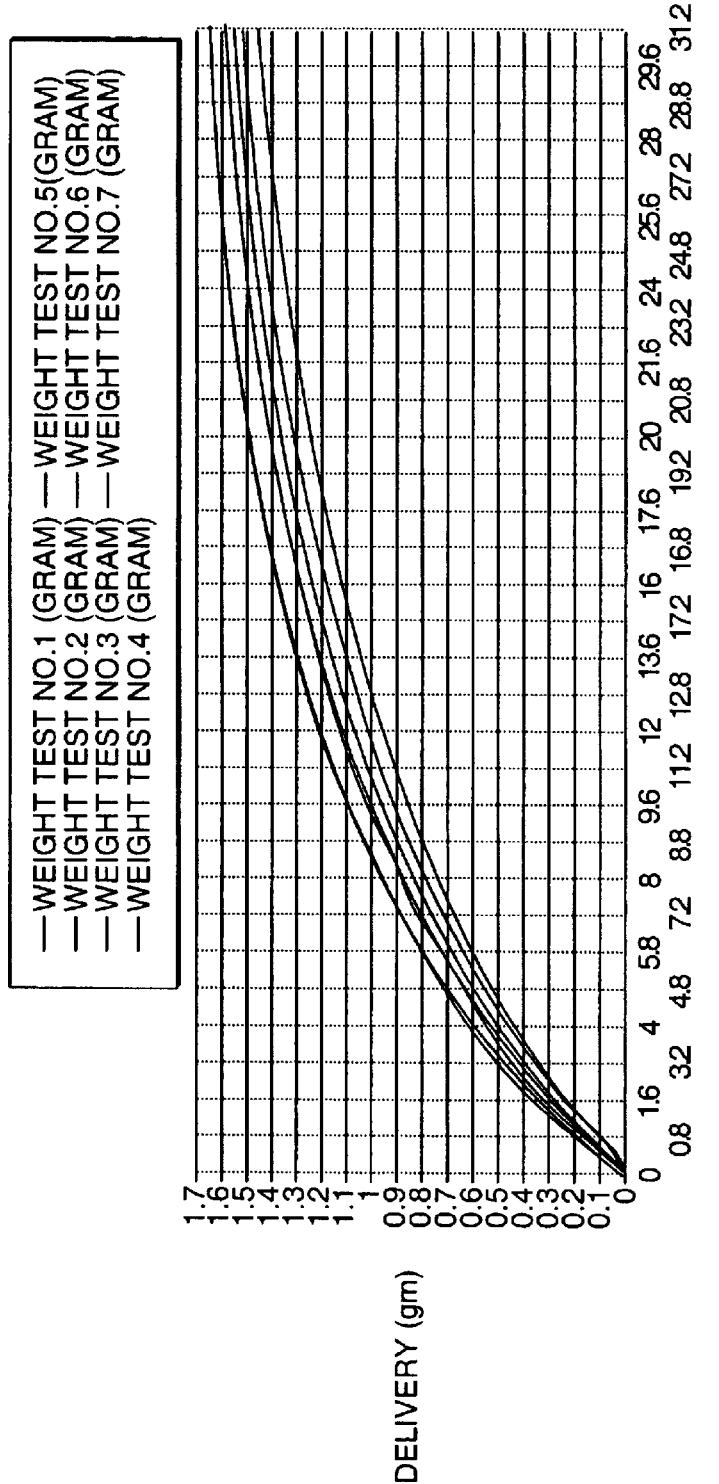

FIGS. 10A and 10B graphically illustrate system characteristics of a preferred embodiment of the drug delivery device. To provide effective delivery of a specified amount of fluid and minimize patient discomfort, the system requires a sufficient fluid pressure in the delivery vial that is manually actuated by the user within a short time period. FIG. 10A shows the pressure (millibars) and weight (grams) characteristics of the system during a delivery period of about 30 seconds for a delivery volume of about 1.6 milliliters. FIG. 10B illustrates test results of the delivery of 1.6 milliliters into different animals using a single drug delivery device for the same time period.

Referring to FIGS. 11A–11D, cutaway views of a preferred embodiment of a diluent container subassembly and a manifold, which may be used with the drug delivery devices or with an ordinary syringe or other drug delivery devices, are illustrated. The diluent container subassembly 300 includes a preassembled compression portion 310 which allows the user to hold the diluent container 312, which can be in the form of a compressible sealed bag, and insert it into a needle 314. The diluent container 312 contains about 1 milliliter diluent and a controlled volume of gas, such as air, for example, and upon insertion into housing 304-6, is pierced by the needle 314. During storage or shelf life, the diluent container 312 is sized to allow for expansion of the container as a result of changes to the environment. In addition, the compression portion 310 is used to compress the exterior of the diluent container and apply pressure to the contents of container during delivery of the diluent for mixing. The diluent containers are formed from flexible, collapsible materials, for example, polyethylene, polypropylene and nylon. The compression portion 310 includes a slider element 316 and two longitudinally extending arms 318, 320 extending therefrom. Two cylindrical drums 322, 324 are spaced between the longitudinally extending arms 318, 320.

Figure 11A:
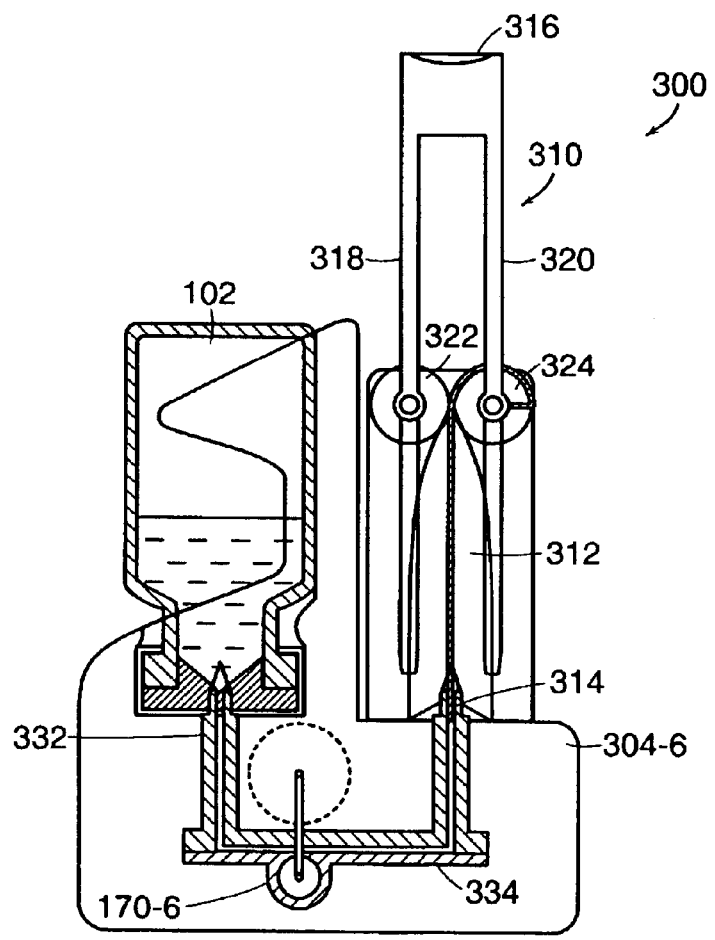
Figure 11D:
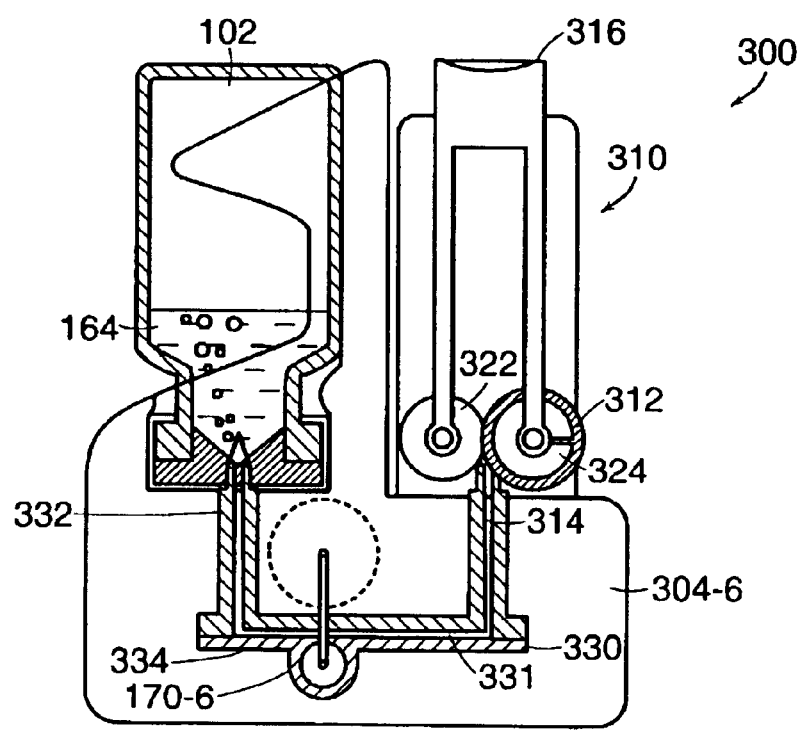

FIG. 11A illustrates the diluent container subassembly 300 positioned in the housing 304-6 of the drug delivery system in accordance with the present invention. FIG. 11D further illustrates the fully compressed state of a preferred embodiment of the diluent container subassembly 300. The slider element 316 of the compression portion 310 translates in at least one axis, for example, in the illustrated embodiment, it can move up or down. The downward movement of the slider element 316 causes the diluent container 312 to wrap around the cylindrical drum 324 which compresses the contents of the diluent container 312, thus forcing the diluent from the container 312 and through the needle 314 and into the vial 102. The movement of the slider element 316 is limited by an end of travel position. At this end of travel position, the slider element 316 may be locked by a locking mechanism which ensures that the diluent container is kept compressed.

A manifold 330 includes two needles 314, 332 fixedly mounted at the ends of an extending member 334. The needles can also comprise a penetrating member that is formed from an injection molded material such as medical grade polycarbonate or acrylic with the required level of rigidity to penetrate the vial or container. A channel 331 provides for fluid communication between the needles 314 and 332. Needle 314 pierces the diluent container 312 upon insertion of the container, while needle 332 pierces the vial 102 upon insertion of the vial containing the lyophilized drug 164. In a preferred embodiment of the present invention, container 312 contains approximately 1 milliliter of diluent and a controlled volume of air which is forced into vial 102, resulting in a pressure inside vial 102 of approximately 2.25 bars. The pressure inside vial 102 results from forcing the controlled volume of air in the diluent container 312 into the rigid volume in the vial 102. Thus, the diluent 166 is forced into vial 102 to mix with the lyophilized drug 164 contained therein. The entire assembly is preferably shaken to ensure the reconstituted drug 160 is properly mixed in preparation for injection. The vial 102 is vertically oriented during injection to ensure air is not being injected into the injection site.

Referring to FIG. 11C, the injector needle 130-6 is shown in a first position within the housing 304-6. As described hereinbefore, the injection needle 130-6 is in the range of a 24–28 gauge needle and is preferably a "U" shaped needle having a second end 172-6 configured to puncture sealing member 170-6. An area 171 is located adjacent to the sealing member 170-6 and is in communication with the channel 331 as shown in 11B.

When the user compresses the button 305, it causes the needle 130-6 to penetrate the skin and the second end 172 to penetrate the sealing member 170. The drug and diluent solution will flow from the needle 332, through the channel 331, and area 171 and to the user via the injector needle 130-6. As the user compresses the button 305, which is spring loaded by spring 306, a pair of mating pawls 307, 308 fit together and prevent the button from being pulled out and the reuse of the device as shown in FIG. 11C.

Figure 12A:
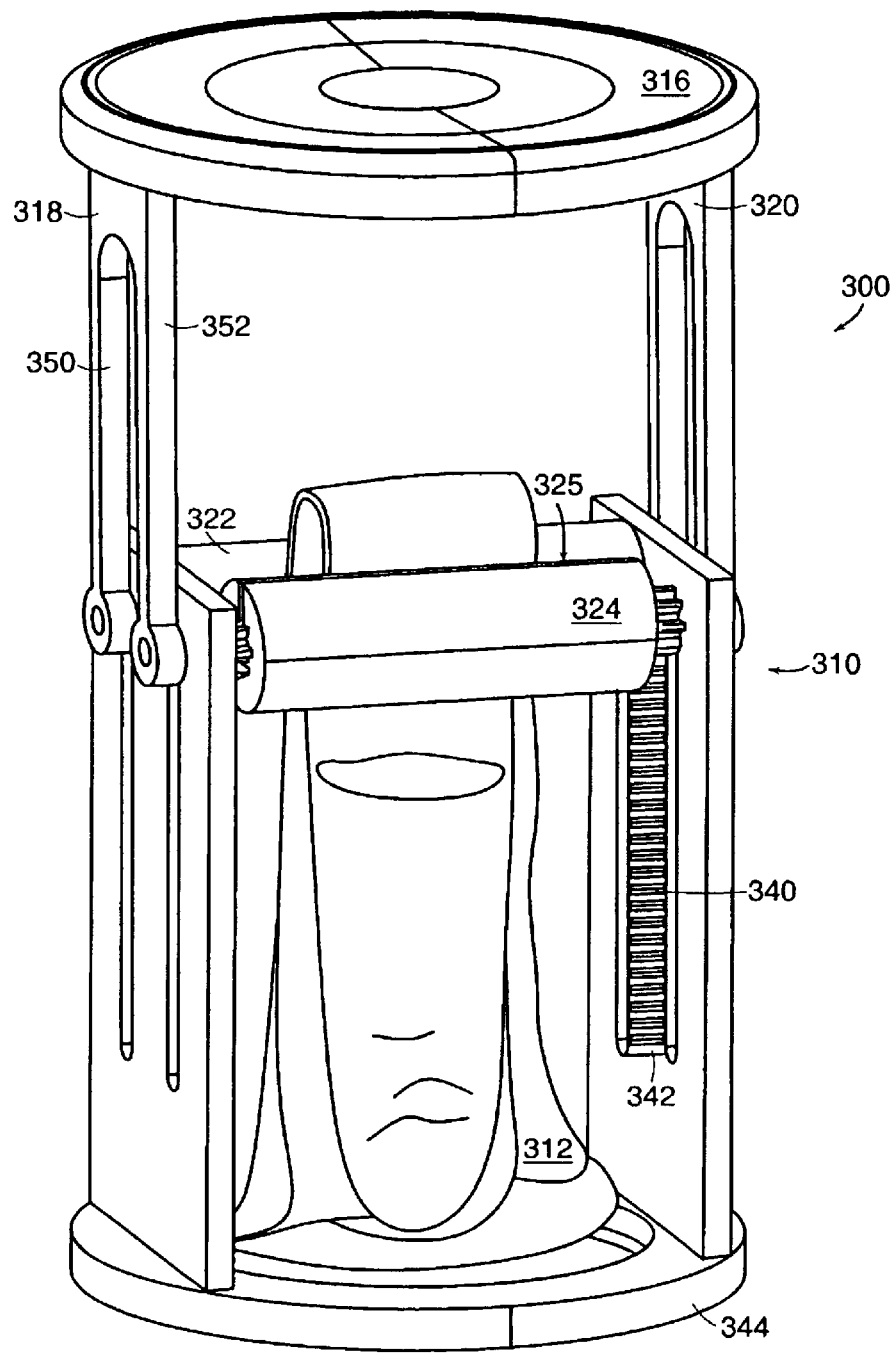
FIGS. 12A–12B illustrate perspective views of a preferred embodiment of the diluent container subassembly shown in FIGS. 11A–11D.
Figure 12B:
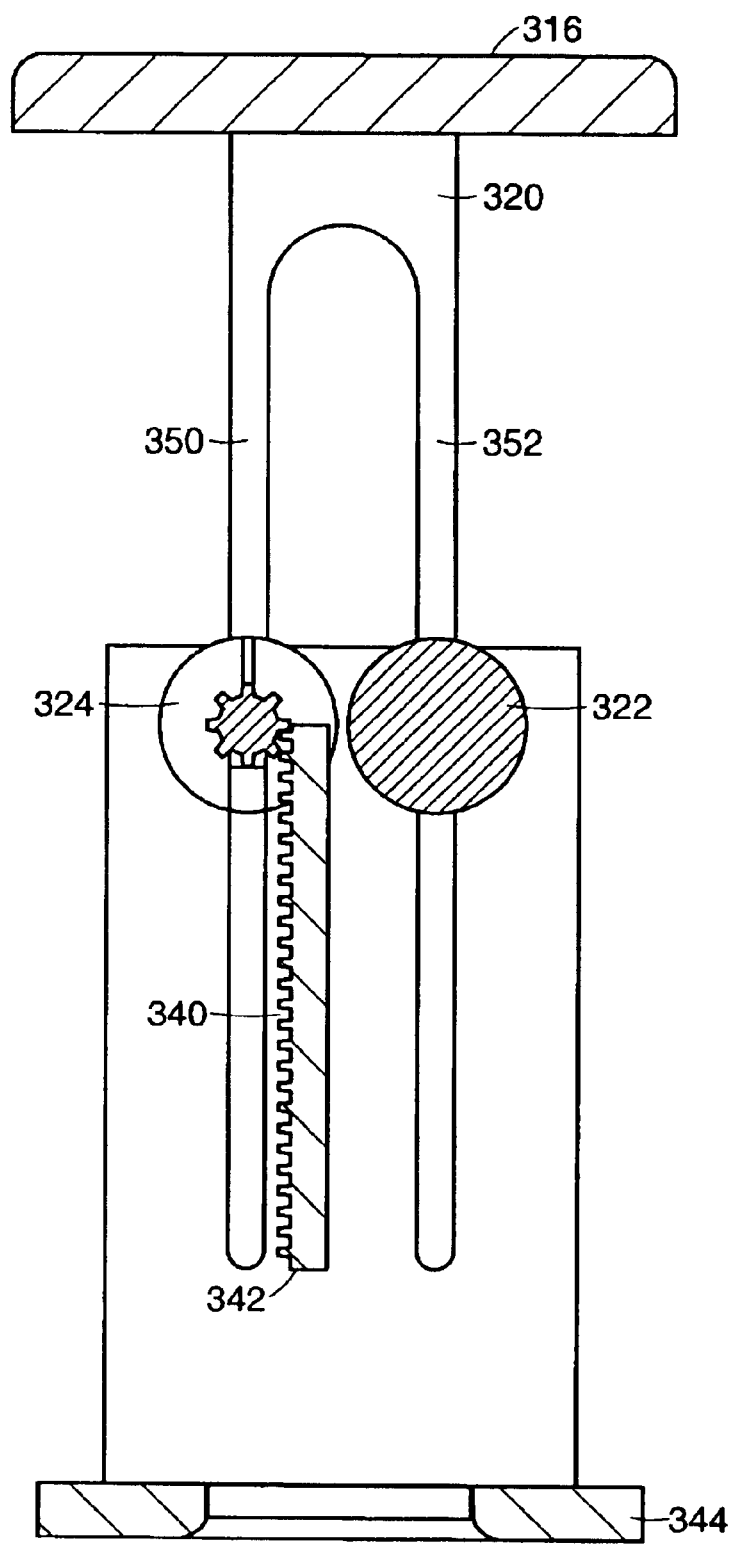

FIGS. 12A–12B illustrate perspective views of a preferred embodiment of the diluent container subassembly 300 and provide further details of the components of the compression portion 310. The cylindrical drum 324 is slotted such that the diluent container can be inserted therein. The cylindrical drum 322 serves as a backing drum. Thus, the diluent container 312 is typically inserted between the cylindrical drum 324 and the backing drum 322. The drum apparatus 322, 324 moves in a rack and pinion gear apparatus 340. An end of travel position 342 in the rack and pinion gear apparatus 340 constrains the movement of the cylindrical drum 324 at its end of movement position. This end of travel position correlates with the end of the wrapping of the diluent container 312 around the cylindrical drum and maximum compression of the contents of the container. A flange 344 can be used to hold the diluent container 312 at the bottom of the subassembly 300. The diluent container 312 can be sealed by means of heat welding techniques or ultra sonic techniques to the flange 344 after it has been filled with the diluent. The longitudinally extending arms 318, 320 in the compression portion 310 each comprise two members 350, 352, as shown in FIG. 12B. A cylindrical drum is attached to each member. The two members 350, 352 are spaced apart from each other to accommodate the wrapping of the diluent container on the cylindrical drum 324.

Referring to FIGS. 13A–13B, cutaway views illustrate an alternate embodiment of the invention similar to that shown in FIGS. 11A–11D including a manifold 350. The manifold 350 has two needles 352, 354 for the purpose of piercing the vial 102 and diluent container 312 respectively. Once the diluent 166 and the controlled volume of air are forced to move into vial 102, the diluent mixes with the lyophilized drug 164 and results in the reconstituted drug 160 which is under pressure. Because the reconstituted drug is under pressure due to the controlled volume of air, it is forced through the needle 352 and into the person being injected through a needle 351 that is actuated by movement of pushing member 353. This embodiment of the device provides a user comfort as it does not have to be vigorously shaken to ensure the reconstituted lyophilized drug 160 is properly mixed in preparation for injection. The controlled volume of air facilitates the mixing of the diluent and the lyophilized drug. The pushing member 353 displaces the injection needle 351 between a first position within the housing 304 and a second position outside the housing, or in an injection state.

It is preferable to prevent displacement of the injection needle 351 when the device 100-7 is not properly oriented, for example, upside down, in order to prevent the compressed gas in vial 102 from being injected. Also, it is preferable to lock the injection needle 351 within the housing 304-7 after a single injection to reduce and preferably to prevent the exposure to the contaminated needle. Additionally, it is preferable to only allow displacement of needle 351 after insertion of diluent container 312. Accordingly, a locking mechanism comprising member 268 as shown in FIG. 4B is provided to accomplish the foregoing. The member 268 has a first end configured to be moved by pushing member 353 and a second end configured to displace a movable locking device, substantially similar to the device shown in FIG. 4B.

With the device 100-7 properly held by the user such that vial 102 is vertically oriented, the user presses pushing member 353 such that the injection needle 351 first extends out of the housing 304-7, thus penetrating the skin of the person being injected. Continued pressing of the pushing member 353 causes the second end 355 of injection needle 351 to puncture sealing member 357, thereby allowing the pressurized reconstituted drug 166 to travel from vial 102 into the person being injected. It may take in the range of 10–30 seconds to deliver the injection fluid. The pressing motion compresses spring 359 such that upon release of pushing member 353, the member returns to the original position, i.e., the needle is withdrawn within the housing 304 and locked therein.

Referring to FIG. 14, a cutaway view illustrates a manifold of another preferred embodiment of the drug delivery device 100-8 in accordance with the present invention. The manifold 350 has two needles 352, 354 for the purpose of piercing vial 102 and diluent container 312, respectively. A flange, substantially similar to the flange 127 shown in FIG. 6B, holds the septum or stopper 313 in place in the container 312. An extending member or communication chamber 356 which is in fluid communication with the needles 352, 354, has a membrane such as a hydrophilic membrane or barrier 360 disposed therein. It should be noted that the hydrophilic membrane needs to be wetted before it functions to minimize or preferably prevent the flow of gas into a user's tissue. The hydrophilic membrane allows gas, for example, air to pass freely till it comes in contact with liquid and gets wet. Thus, when wet, no air such as the controlled volume of air in the diluent container 312 can pass through the hydrophilic membrane, preventing air from entering the user's tissue. The presence of the hydrophilic membrane prevents risks caused by any wrong use of the device 100-8 by the user such as incorrect positioning of vials or containers.

Figure 15A:
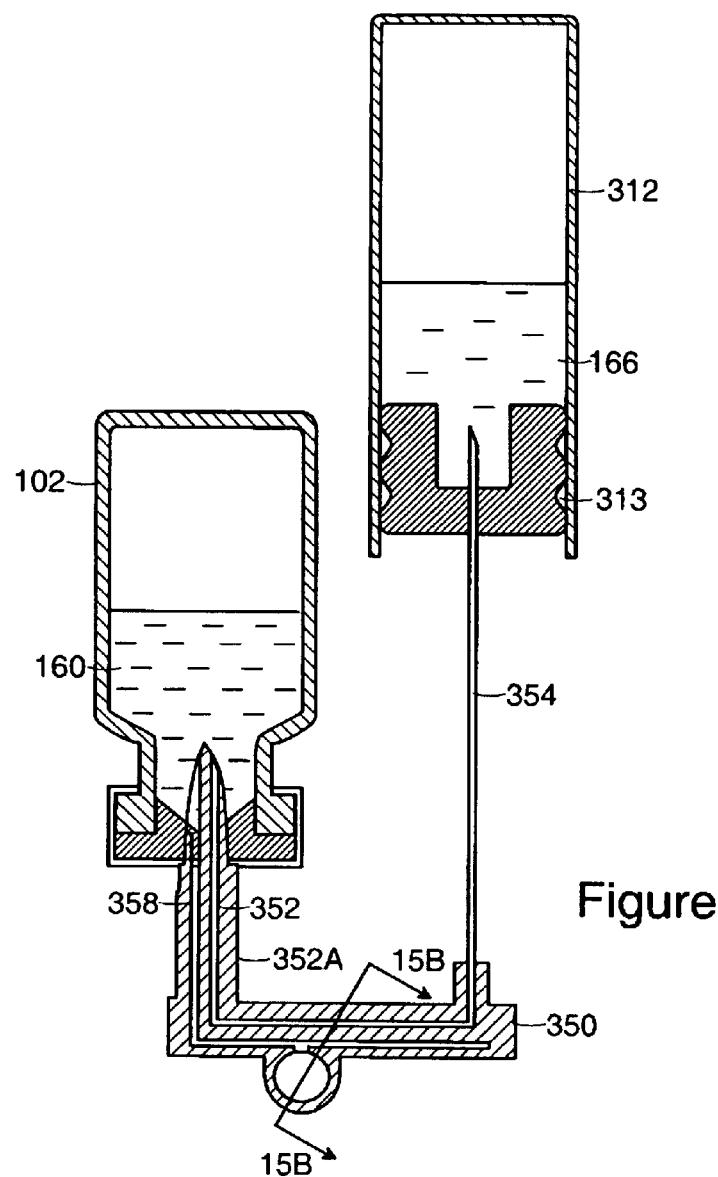
FIGS. 15A and 15B illustrate cutaway views of an alternate embodiment of the drug delivery device in accordance with the present invention.
Figure 15B:
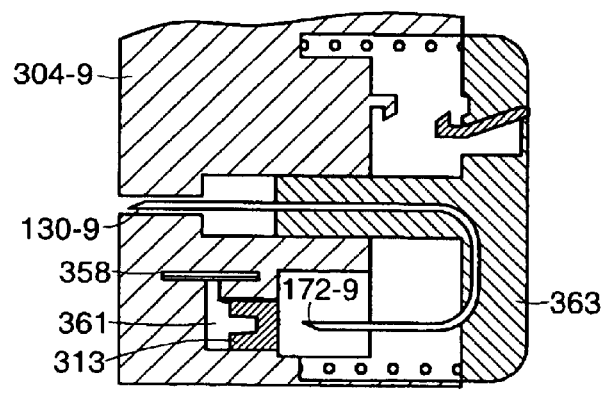

Referring to FIGS. 15A–15B, cutaway views illustrate another preferred embodiment of a manifold of the drug delivery device in accordance with the present invention. The needle 352 pierces the vial 102 while needle 354 pierces the diluent container 312. The needle 354 and channel 352 on spike 352A are in fluid communication. Diluent 166 moves from the diluent container 312 into vial 102, thus mixing with the lyophilized drug to result in a reconstituted drug. A channel 358 is in communication with an area 361 sealed by a stopper 313. Channel 358 also includes a hydrophilic membrane. Thus, upon the introduction of air to the channel, the membrane expands in the presence of air and disallows the passage of air therethrough.

In use, the user presses the button 363 which first moves injector needle 130 into the users skin. Further movement of the button 363 causes piercing member 172 to penetrate the stopper 313. This enables liquid drug/diluent solution to move, via the air pressure in the vial 102 through the injector needle 130 and the user's skin.

It should be noted that the embodiment illustrated with respect to FIGS. 15A and 15B being more position independent, is not subject to air blocking the flow of liquids through the gas impermeable membrane until all the drug solution has been transferred out of the vial 102.

FIG. 15A shows the position of channel 358 relative to channel 352. Thus, only if the vial 102 is completely filled with air would it pass into channel 358. In contrast, the embodiment illustrated with respect to FIG. 14 and the absence of the lower channel 358 is more position dependent and thus subject to air blocking the flow of liquids through the gas impermeable membrane even while the drug solution is being transferred out of the vial 102.

Further, it should be noted that the delivery times of the drugs is dependent on the volume of vial which maybe adjusted. The pressure is adjusted in part by adjusting the vial volume size. A large vial volume of air relative to the drug would result in greater air pressure and faster drug delivery.

In the preferred embodiments of the present invention the drug vials and the diluent containers are shown as being inserted in the housing 304 and aligned in the same direction along parallel axes. In the alternative, it is contemplated that the vials and containers may not be aligned in the same direction along parallel axes. The vials and containers may be inserted along two different axes that are oriented at oblique or orthogonal angles relative to each other.

Figure 16:
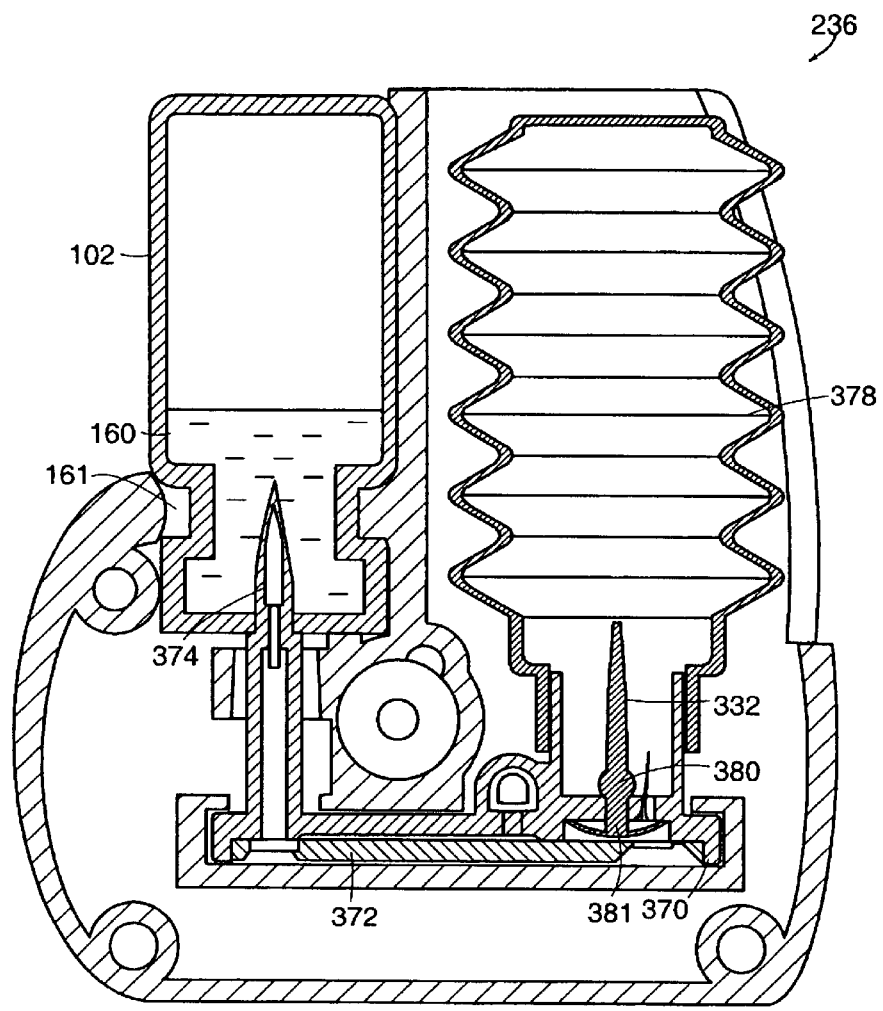
FIG. 16 illustrates a cutaway view of an injection device in accordance with the present invention.

Referring to FIG. 16 a cutaway view illustrates an alternate preferred embodiment of an injection device 236 in accordance with the present invention. The device 236 facilitates the sterilized injection of a prefilled cartridge or vial containing an injectable liquid, for example, a vial containing a liquid drug 160. The device 236 includes first opening 161 for receiving vial 102 and a manifold 370 including member 372 sealingly engaged with the first opening 161. Member 372 fixedly supports needle 374 and is supported by a collapsible volume, such as bellows 378, or any other device capable of injecting a fluid such as a gas upon being compressed. A check valve 380 ensures that the flow from the bellows is unidirectional, that is, the drug under pressure can not enter the bellows 378. The check valve 380 comprises a tubular member 381 adapted to deliver gas, for example air, to the vial 102. Air is moved out of the bellows and into the tubular member 332 by compressing, the bellows 378. The check valve 380 allows the flow of air out of the bellows 378 and into the vial but disallows the reverse flow of air from the vial into the bellows. Air from the bellows 378 is forced up through needle 374 and into vial 102 applying pressure to the contents of the vial 102. The liquid drug 160 is under pressure and is injected into the user directly from the vial 102. The injection process is the same as discussed earlier with respect to embodiments in FIGS. 13–15, in that the use of a U-shaped needle assembly is compressed into the skin to activate injection. As discussed earlier, due to the nature of the hydrophilic material, a hydrophilic membrane 360 in the drug delivery path minimizes and preferably prevents gas from being injected into the user.

Referring to FIGS. 17A–17C, cutaway views illustrate an alternate embodiment of the drug delivery device 100 in accordance with the present invention. The diluent container comprises a syringe 390. When pressure is applied to a plunger shaft 392, the diluent 166 is forced out of the syringe 390 through the channel 398 and into the contents of vial 102 via the needles 394, 396 which are in fluid communication with each other through the member 398. Thus, the diluent 166 is provided to vial 102 under pressure and is mixed with the reconstituted drug to result in a reconstituted drug solution ready for injection or delivery under pressure to a patient. The drug solution is delivered to a user using a u-shaped needle assembly as disclosed with respect to FIGS. 13A–13B, 14, and 15A and 15B. This syringe embodiment facilitates the use of a standard prefilled container or cartridge containing only a diluent. The device is flexible and does not require special means or training.

The present invention includes alternate preferred embodiments of injection devices. FIGS. 9A–9F illustrate an injection device 236 which facilitates the sterilized injection of a prefilled cartridge or vial containing an injectable liquid, for example, a vial containing a reconstituted drug 160. It is preferable to use a standard vial, for example, a 2 milliliter vial, with this device 236. As shown in FIG. 9A, device 236 includes a first opening for receiving the vial 102 and a manifold including member 232 which is slidably and sealingly engaged with the first opening. Member 232 fixedly supports needle 224 and is supported by a collapsible volume, such as bellows 228, or any other device capable of injecting air upon being compressed.

Needle 224 is in sealed communication with the bellows 228 as shown in FIG. 9A. The vial 102 is pressed into the housing 304-5 such that needle 224 pierces the rubber stopper 112. This arrangement is shown in FIG. 9B.

The vial 102 is further pressed into the housing 304-5 which forces member 232 to compress bellows 228, thus forcing the air contained in bellows 228 up through needle 224 and into cartridge 116. Now, as illustrated in FIG. 9C, the cartridge 116 is under pressure for forcing the drug 166 into the person being injected. The bellows or other compression device can also be actuated by member 174-5.

As shown in FIGS. 9A–9F, device 236 is further provided with a pushing member 226 for displacing the injection needle 130-5 between a first position within the housing 304-5 and a second position outside the housing, or in an injection state. In the preferred embodiment a distal end of the injection needle 130-5 can extend out of the housing 304-5 in the range of 5–12 millimeters. In this particular embodiment, the injection needle 130 is preferably a "U" type needle having a second end 250 configured to puncture sealing member 230. Sealing member 230, which may comprise any puncturable material such as butyl rubber, maintains the liquid in the upper part of housing 304. As the user presses pushing member 226 into housing 304, the first end of the injection needle 130 first penetrates the skin of the person being injected as shown in FIG. 9D. Continued pressing of pushing member 226 into the housing 304 causes the second end 250 of injection needle 130-5 to puncture sealing member 230, thereby allowing the reconstituted drug 160 to travel from cartridge 116 into the person being injected. This is illustrated in FIG. 9E. The pressing of the pushing member 226 into the housing 304-5 compresses a spring such that upon release of pushing member 226, the member returns to the original position, i.e., the injection needle 130-5 is in the first position within the housing 304-5 as shown in FIG. 9F. This embodiment may be further provided with a locking mechanism similar to that disclosed in FIGS. 4A–4K. With the injection needle locked within the housing 304-5, the device 236 may be safely discarded.

Further, FIGS. 18A–18C illustrate an injection device in accordance with an alternate preferred embodiment of the present invention. More particularly, the drug delivery device 400 includes a straight needle 402 having a lancet 404 disposed on a first end. A cavity 405 in the septum 406 contains a liquid drug under pressure. The straight needle 402 includes a side hole 407 disposed on the shaft. The second end 408 of the straight needle is blocked. In operation, as shown in FIGS. 18A, 18A-1, 18B and 18B-1, when the member 410 is moved forward toward the housing 412, the injection needle 402 is displaced from a first position in the housing 412 to a second position outside the housing such that the needle 402 penetrates the skin of the user. After the lancet 404 penetrates the user's tissue, continued pressing motion of the member 410 toward the housing causes the side hole 407 to be in fluid communication with the cavity 405 of the septum 406 creating a path for the drug under pressure to flow into the user's tissue. The straight needle punctures the septum 406 at two locations. As shown in FIG. 18C, as the member 410 is released, the injection needle is withdrawn within the housing 412.

More particularly, referring to FIG. 18A-1, a 3 part ring structure including member 414, latch 416, gap 418 and spring 419, as shown in FIG. 18A provide an interlocking system. This safety mechanism which includes the members 410, 414, latch 416, gap 418 and spring 419 provides an interlock to ensure against reuse of the drug delivery device 300 and exposure of needle 402 after the first use. Once the member 410 is compressed the mating ridges 413A and 413B come together. The ridges are angled on one side to allow ridge 413B to pass under 413A when member 410 is depressed against the housing 412. The ridges are pressed together when the force of the spring 419 moves member 410 away from the housing 412. Because the ridges interface at a right angle to the direction of movement of the member 410 they serve to prevent further movement by the member and the needle 402. This mechanism ensures that the device 400 is not reused.

FIGS. 19A–19F illustrate cutaway views of alternate preferred embodiments of systems which allow reconstitution of drug and subsequent transfer into a drug delivery device in accordance with the present invention. Once the drug is made into a solution it may be transferred into a user by means of direct injection as shown in FIG. 11, for example, or into a drug delivery device such as an infusion pump, needleless injector or the like. The systems include a vial 420 containing a predetermined volume of a drug and a vial 422 containing a volume of a diluent. The use of standard vials facilitate the use of the drug delivery device by different drug suppliers.

Figure 19A:
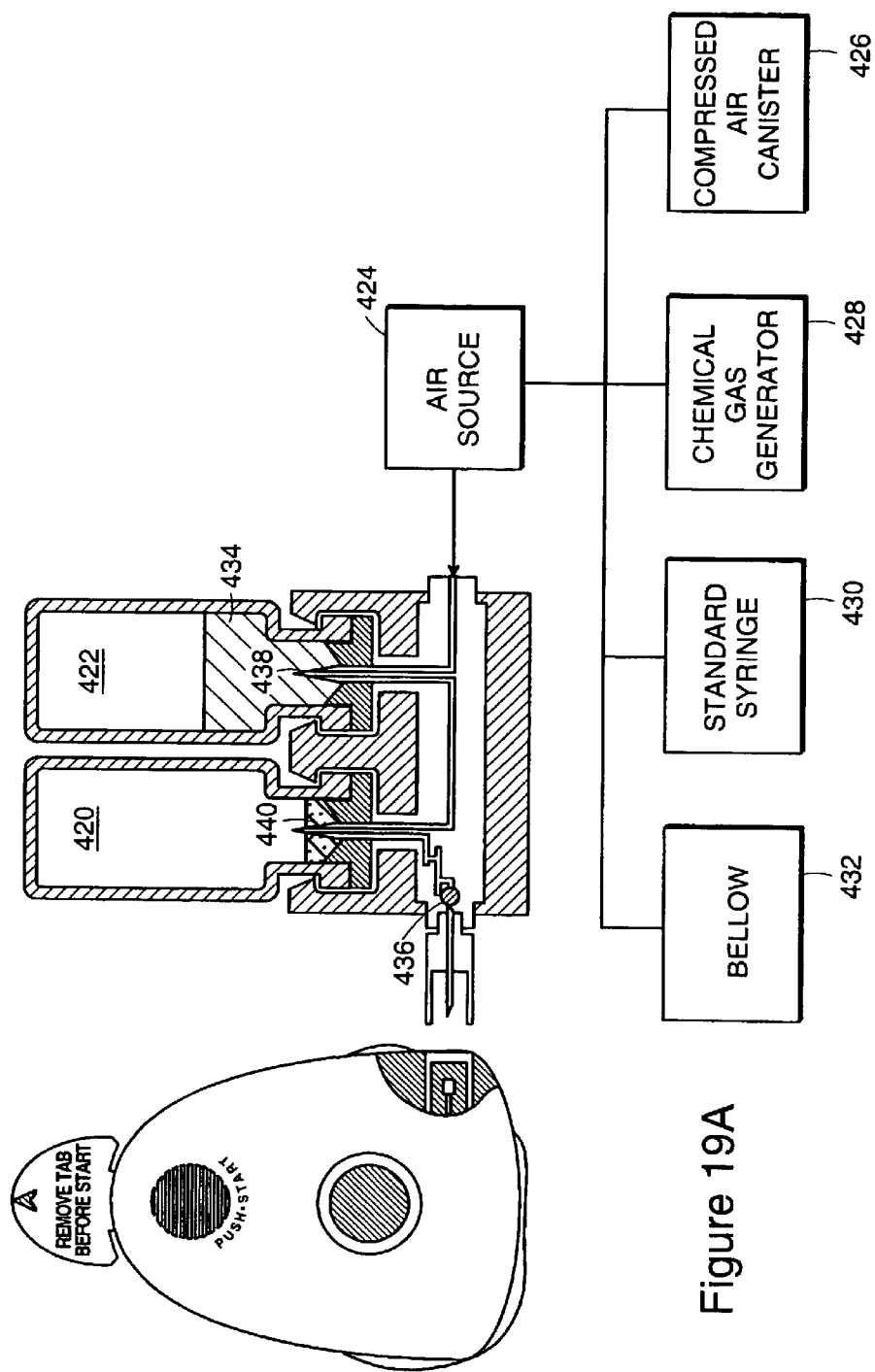
FIGS. 19A–19F illustrate alternate embodiments of pressurization systems included in the drug transfer system in accordance with the present transfer invention.

An air source 424 maybe included for the delivery of drugs. With drugs of higher viscosity, the use of pressure becomes more important. As illustrated in FIG. 19A, the sources of pressurized air can vary and may include, but are not limited to, a compressed air delivery supply 426, a chemical gas generator 428, a standard syringe 430 and a collapsible volume container, such as a bellow container 432. The air source supplies the driving force to the diluent volume which moves the diluent solution 434 into the standard lyophilized drug vial 420. Once reconstituted, the liquid drug is transferred via the air separator, such as a hydrophilic membrane 436, to a drug delivery system. It should be noted that spike 438 in the diluent vial 422 and spike 440 in the drug vial 420 each have two paths. The spike 438 has a first path for compressed air to enter the diluent vial 422 and a second path for the pressurized diluent 434 to be in fluid communication with the drug vial 420. The spike 440 has a first path for the pressurized diluent to enter the drug vial 420 and a second path for the delivery of the drug solution into a drug delivery device. As discussed earlier, it is contemplated that other drug delivery devices may be received into this system to receive the drug solution.

Figure 19B:
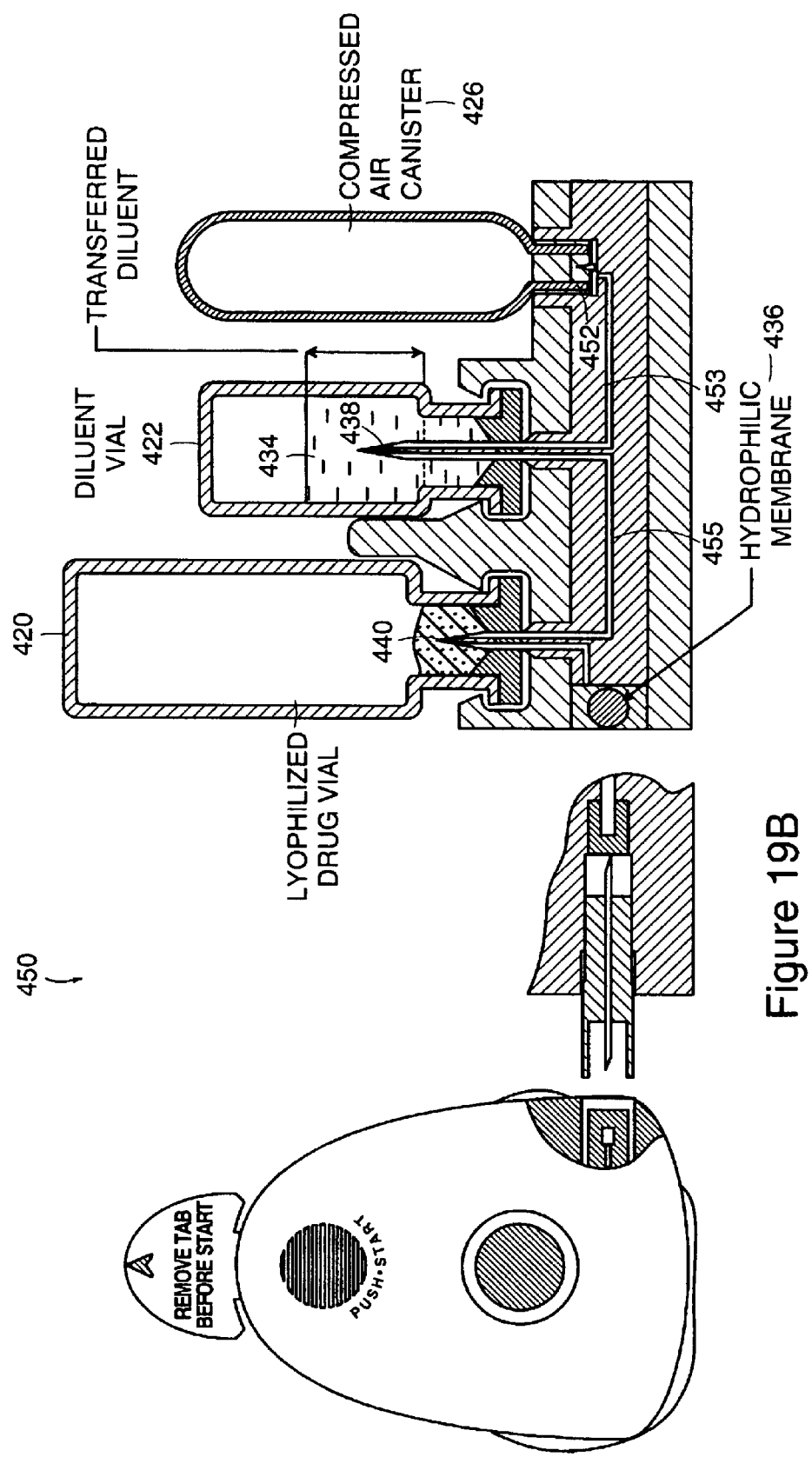

Referring to FIG. 19B, the air source is a compressed air canister 426. The compressed air canister typically is a standard addition for domestic drug delivery devices. The user attaches the compressed air canister 426 to the drug delivery system 450 and punctures a seal 452 located in the compressed air canister. The air canister is then in fluid communication with the diluent vial 422 by means of channel 453. Air is released from the compressed air canister 426 and is introduced into the diluent vial 422, which in turn forces the diluent solution 434 to move into the drug vial 420 via channel 455. After reconstitution is completed, the liquid drug is ready to be transferred. The concentration of the reconstituted drug can be controlled in this and other embodiments by changing the quantity of diluent transferred to reconstitute the drug. A hydrophilic membrane 436 in the drug delivery path minimizes and preferably prevents gas from being transferred to the drug delivery device.

Figure 19C:
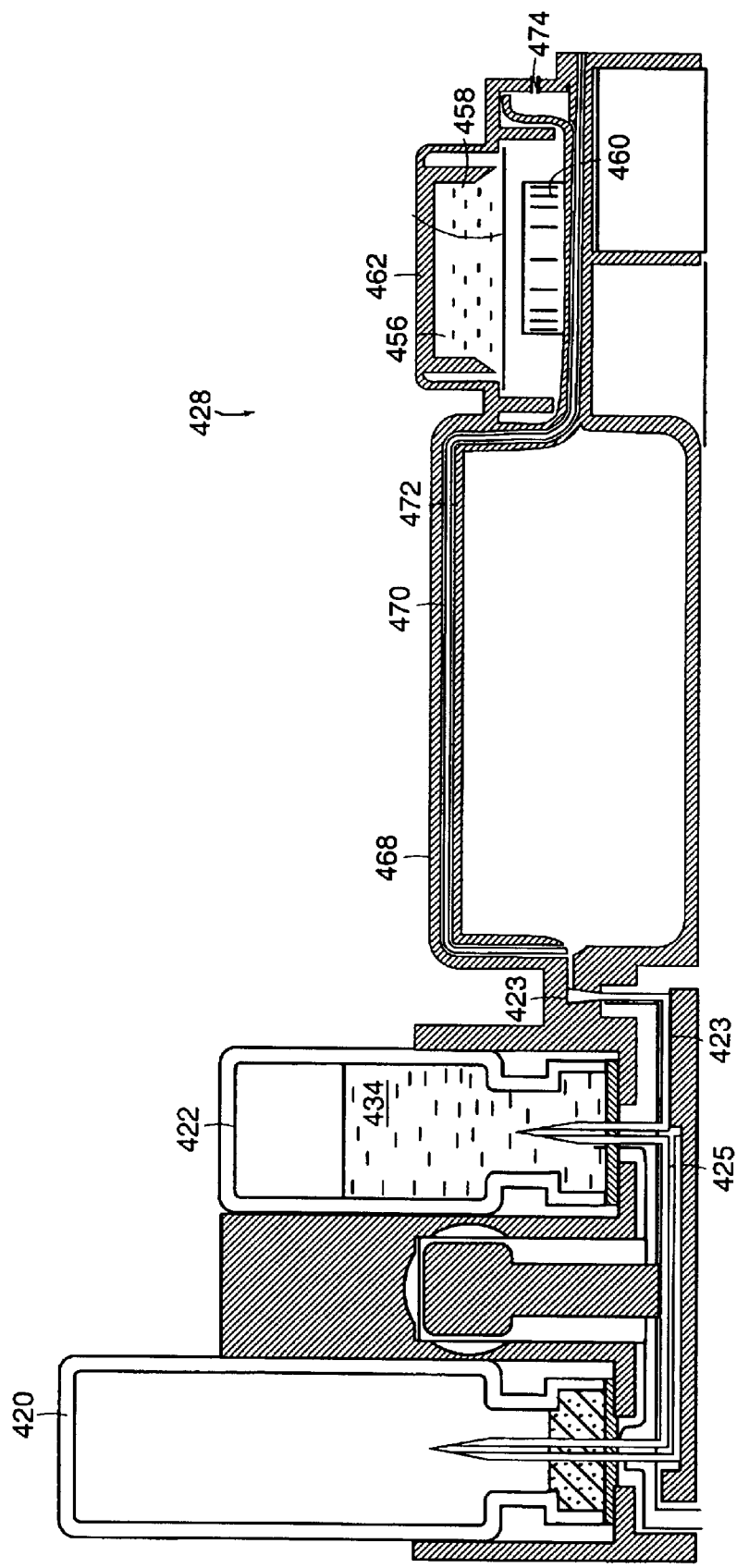

FIG. 19C shows a chemical gas generator 428 as the air source used in this particular embodiment to deliver the diluent 434 under pressure to the lyophilized drug vial. The chemical gas generator 428 includes a chemical compartment 456 which typically contains two materials 458, 460. The two materials 458, 460 can be two liquids or a liquid and a solid palette 460 that are separated during shelf life. It should be noted that the materials used in the chemical compartment 456 and the reaction that ensues during the mixing of the materials are safe and biocompatible. Pushing a member 462, in the chemical compartment 456 results in tearing of a seal 464, for example, aluminum foil, which separates the two materials 458, 460 during shelf life. The two materials are then in fluid communication and react to produce a gas such as, for example, carbon dioxide. The chemical gas generator 428 also includes a gas compartment 466 which is typically an air reservoir having a flexible enclosure 468. The carbon dioxide produced in the chemical compartment 456 due to the reactions enters the gas compartment 466 and is accommodated in the flexible layers 468 that form the gas compartment. The movement of the flexible layers 470, 472 force the air or carbon dioxide into the diluent vial 422 through the air pathway 423. It should be noted that the gas compartment 466 has a double layer 470, 472 comprising the flexible containment area. The two layers 470, 472 provide for safety as if the air or gas generated as a result of the reaction in the chemical compartment does leak, it can be accommodated between the flexible enclosure 468 of the gas compartment 466. Further, the gas compartment 466 is vented using a gas leakage pathway or vent port 474. The air that is released from the chemical gas generator 428 enters the diluent vial 422 via the channel 423 which in turn forces the diluent solution 434 to move into the drug vial 420 via the channel 425. After reconstitution is completed, the drug is ready to be used, and is transferred to a drug delivery system such as one described with respect to FIG. 19B.

Figure 19D:
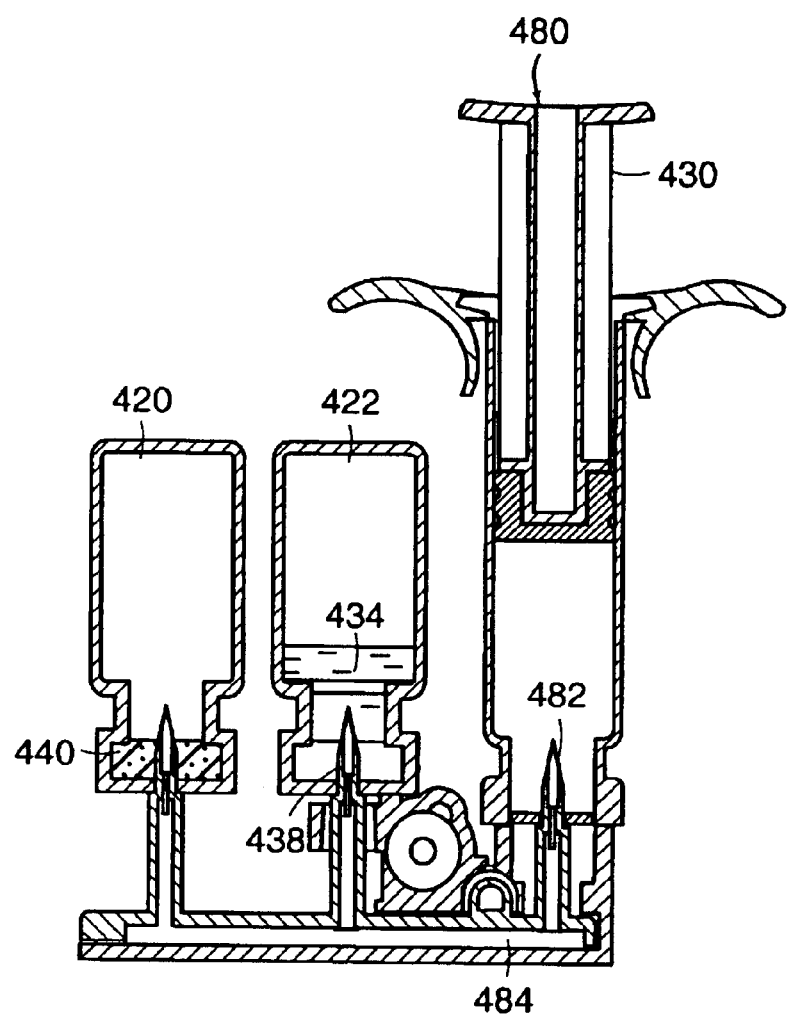

Referring to FIG. 19D, the air source used in this particular embodiment to deliver the diluent under pressure is a standard syringe 430 or an air reservoir. The syringe 430 is locked at an end of travel position. When pressure is applied to a plunger shaft 480 the air is forced out of the syringe 430 and into the contents of the diluent vial 422 through the needle 482 and needle 434 which are in fluid communication through the member 484. The diluent 434 is then forced into the drug compartment or drug vial 420 via member 484 under pressure which provides for the mixing with the lyophilized drug to result in a reconstituted drug which is then ready for injection or delivery under pressure to a user. In an alternate embodiment, a lever can be included to reduce the force required for pushing the plunger member 480. The lever will increase the displacement and thus delivery of pressurized air to the diluent container in this case, the drug solution may be injected as shown in FIG. 19D, the sectional of which is the same as shown and described in other needle assemblies, for example, shown in FIGS. 11, 13, 14, 15, 16, and 32 or transferred into a drug delivery device.

Figure 19E:
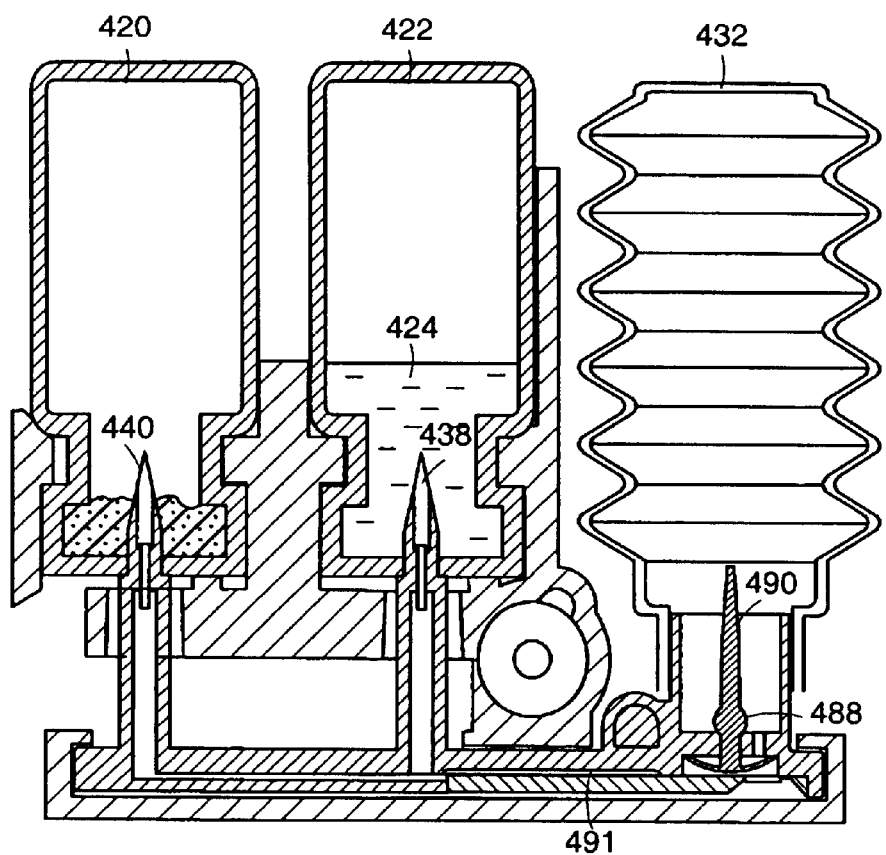

Referring to FIG. 19E, the air source used in this particular embodiment to deliver the diluent under pressure to the lyophilized drug is a collapsible volume container such as a bellow container 432. A check valve 488 or a one-way valve insures that the flow from the bellow container 432 is unidirectional, that is, the drug or diluent can not enter the bellows. The check valve 488 comprises a tubular member 490 adapted to deliver gas, for example air, to the diluent vial 422. The resilient nature of the bellows is checked by the check valve 480 which does not allow air to enter the bellows and thus reinflate the bellows once the bellows have been compressed and air has exited. Once compressed, air contained in the bellows 432 is forced through needle 438 and into the diluent vial 422 via channel 491 applying pressure to the contents of the diluent vial. The diluent solution 434 in turn, is delivered under pressure to the drug vial 420 where the drug is reconstituted and can be transferred either by injection as described above or into a drug delivery device, as also described and shown relating to the embodiment of FIG. 19A.

Figure 19F:
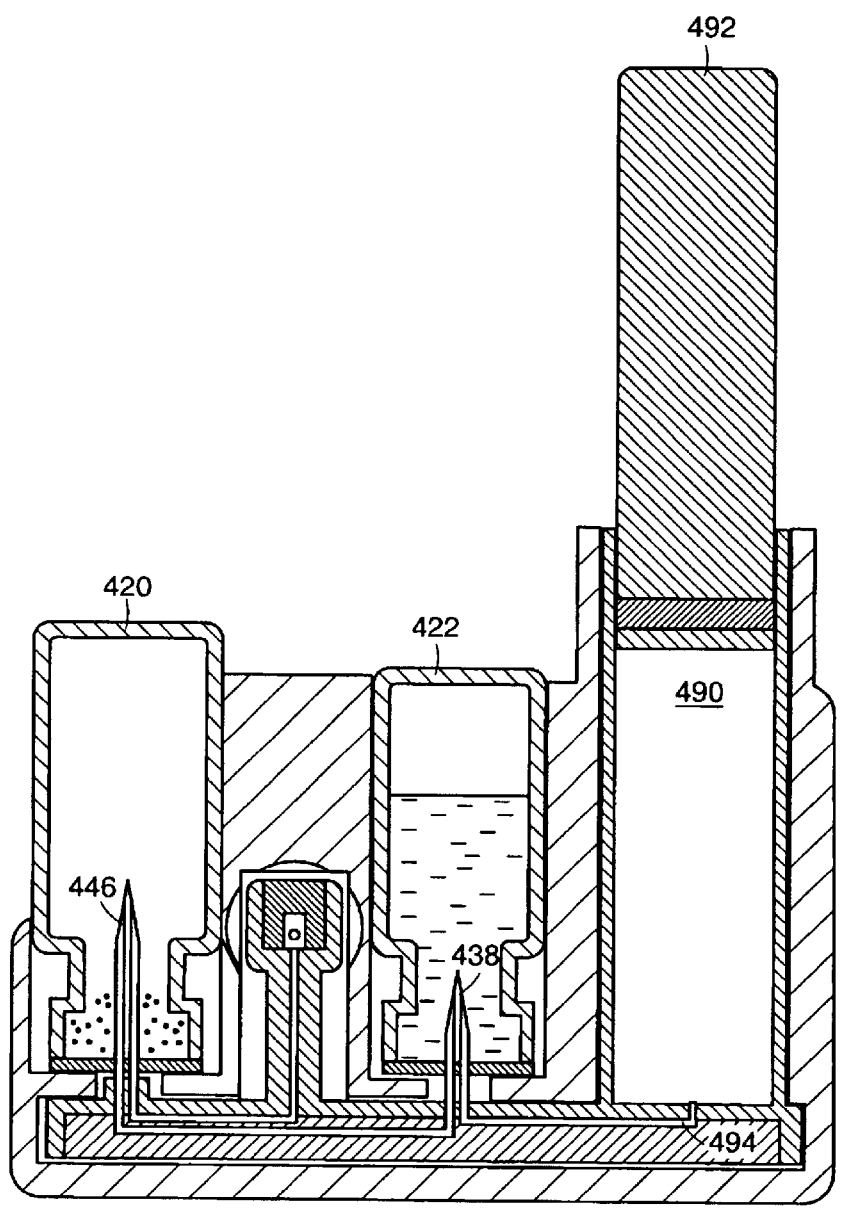

Referring to FIG. 19F, the air source used in this particular embodiment to deliver the diluent under pressure is cylinder 490. This embodiment is similar to the embodiment containing a standard syringe as described with respect to FIG. 19D. The plunger 492 is depressed to compress the air in the cylinder 490. The air is driven into the diluent vial 422 through channel 494 which brings the cylinder and the diluent vial in fluid communication. The pressurized diluent in diluent vial 422 then moves into the vial 420 and mixed with the drug. The pressurized drug solution is then ready to be delivered. This can either comprise delivery to a drug delivery device as described with respect to the embodiment of FIG. 19A or injected as shown in the present embodiment having a straight needle assembly as shown and described in FIG. 18.

Figures 3, 20B:
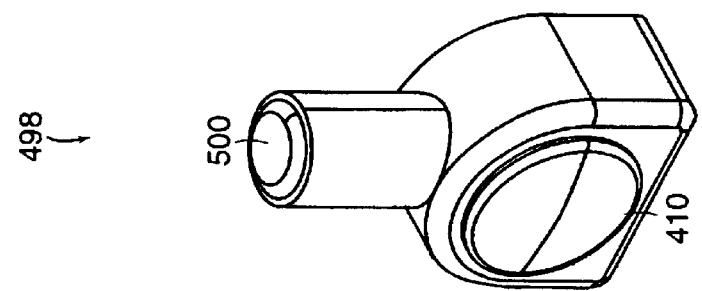
Figures 2, 20B:
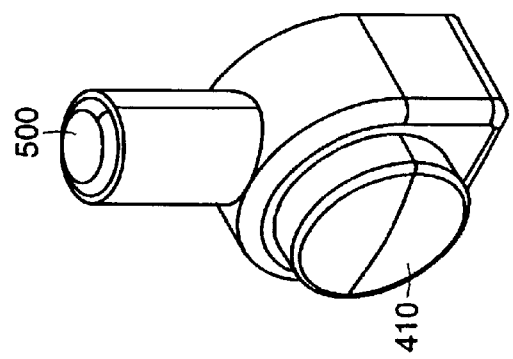
Figures 1, 20B:
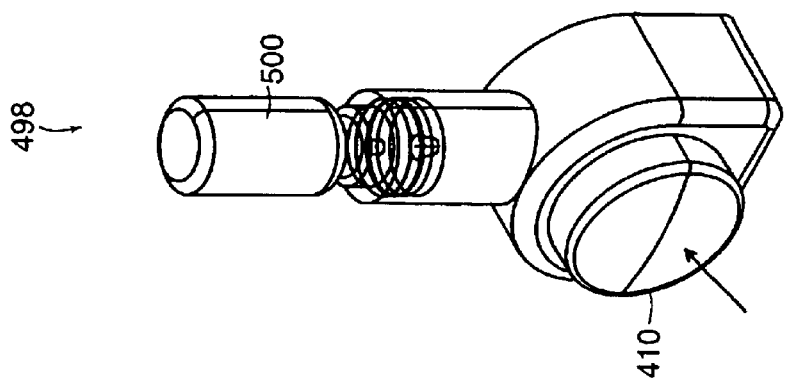
Figures 3, 20C:
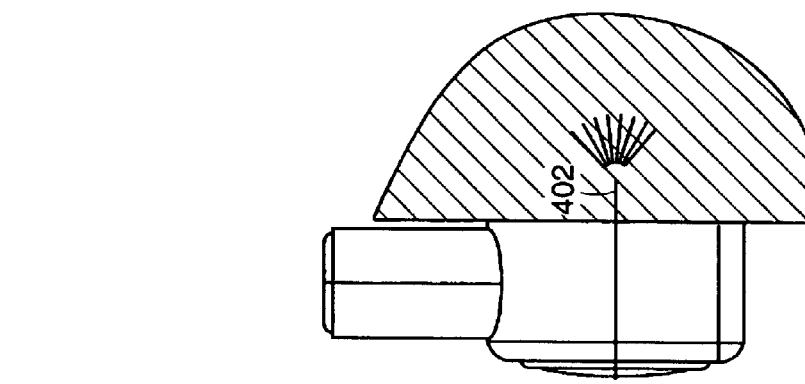
Figures 2, 20C:
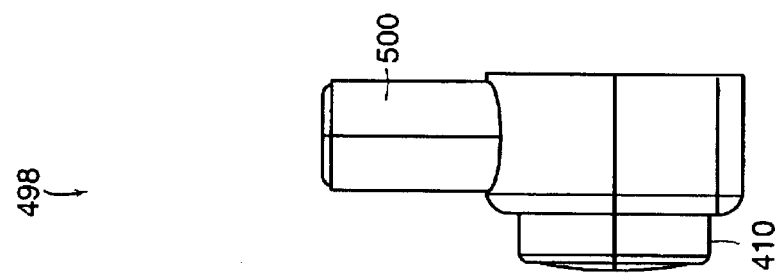
Figures 1, 20C:
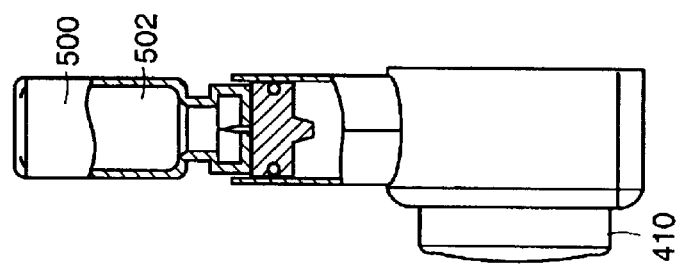

Referring to FIGS. 20A–20C, an alternate embodiment of the drug delivery system 498 in accordance with the present invention includes standard vial 500 containing a liquid drug 502. A volume of gas, for example air, contained in an air chamber 504 is introduced in the standard liquid drug vial 500, creating air pressure above the liquid drug which allows for delivery of a liquid drug under pressure. The usage is position dependent, that is the delivery of the liquid drug, is performed with the standard vial 500 in a vertical position. In addition, a hydrophilic membrane minimizes or preferably prevents the introduction of the extra volume of air into the user's tissue.

In use, as shown in FIG. 20A, the standard vial 500 containing the liquid medicament 502 is inserted into the drug delivery device 498 in accordance with the present invention. An air chamber 504 is provided which upon insertion of the drug vial 500 and the puncturing of the seal 506 of the vial, is in fluid communication with the drug vial. Once inserted, the lip 505A of a standard vial 500 is locked into position by means of a pair of arms 505 having ridges 507 projecting inwardly therefrom. The injector system is the straight needle 402 embodiment as disclosed in FIGS. 18A–18C. Once the air from the air chamber is introduced into the standard drug vial 500 the liquid drug is pressurized and is ready to be injected using the injector system described with respect to FIGS. 18A–18C. After injection into the user's tissue, the needle is retracted automatically. The drug delivery device 498 is then disposed.

Figure 21:
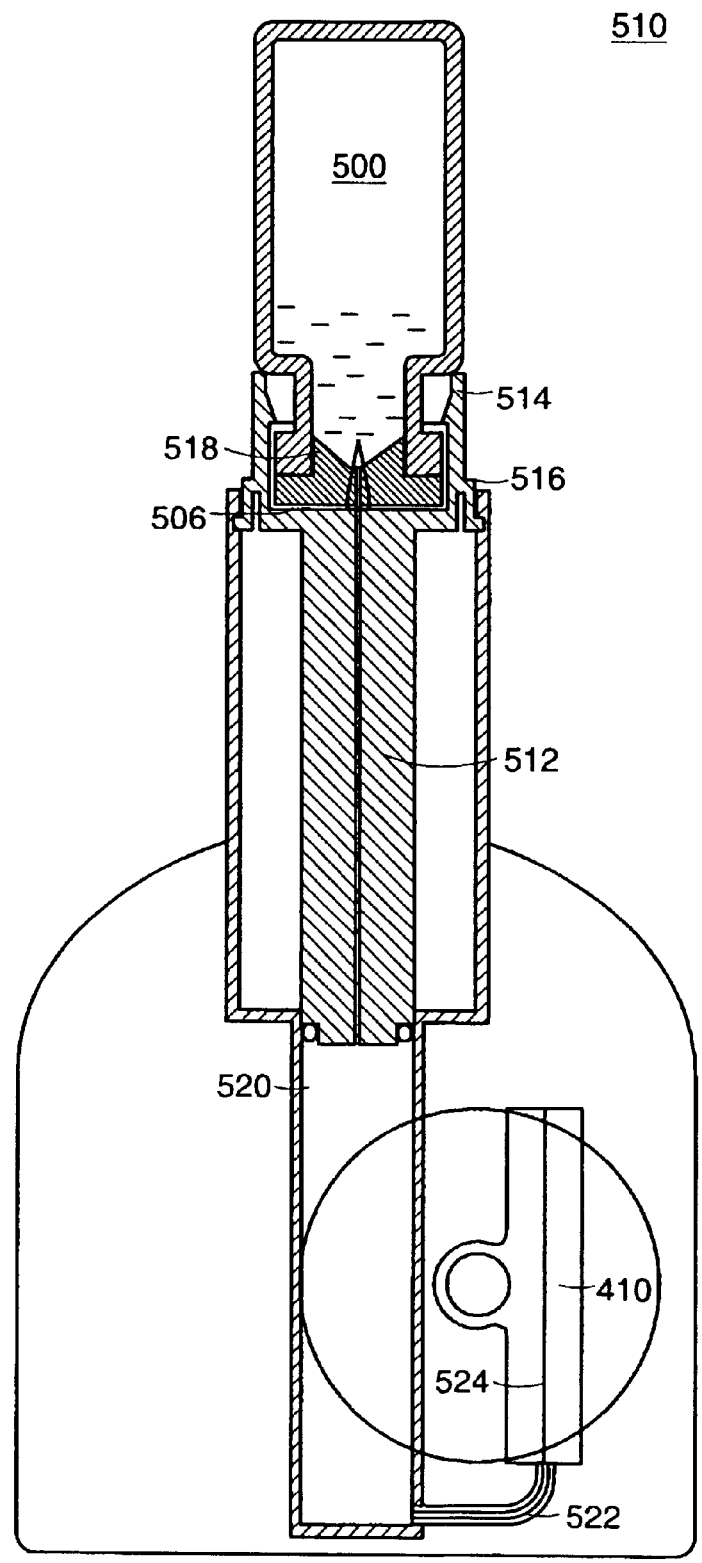
FIG. 21 illustrates a view of another preferred embodiment of the drug delivery system in accordance with the present invention which uses standard vials containing a liquid medicament.

Referring to FIG. 21, an alternate preferred embodiment of a drug delivery system 510 which uses standard vial 500 containing a medicament is disclosed. A plunger 512 is included in the drug delivery device 510. In order to reduce forces which are required to insert the standard vial 500 in the drug delivery device 510. In an alternate embodiment, the drug delivery system 510 can have a compact configuration without a plunger. Snaps 514 lock the standard vial 500 into position. Snaps 516 hold the end portion of the vial having the seal 506 in place to ensure that the spike 518 pierces the seal 506 of the vial 500 before the vial is moved in the downward direction. Air in the air chamber 520 is delivered to the vial 500 when the air is compressed and displaced by the downward movement of the vial 500. The liquid drug under pressure is delivered to an injector using tubing 522. A hydrophilic membrane 524 minimizes or preferably prevents gas from entering the user's tissue. The injector system used can be similar to one described with respect to FIGS. 18A–18C. The member 410 is moved to displace the injection needle 402.

Figure 22A:
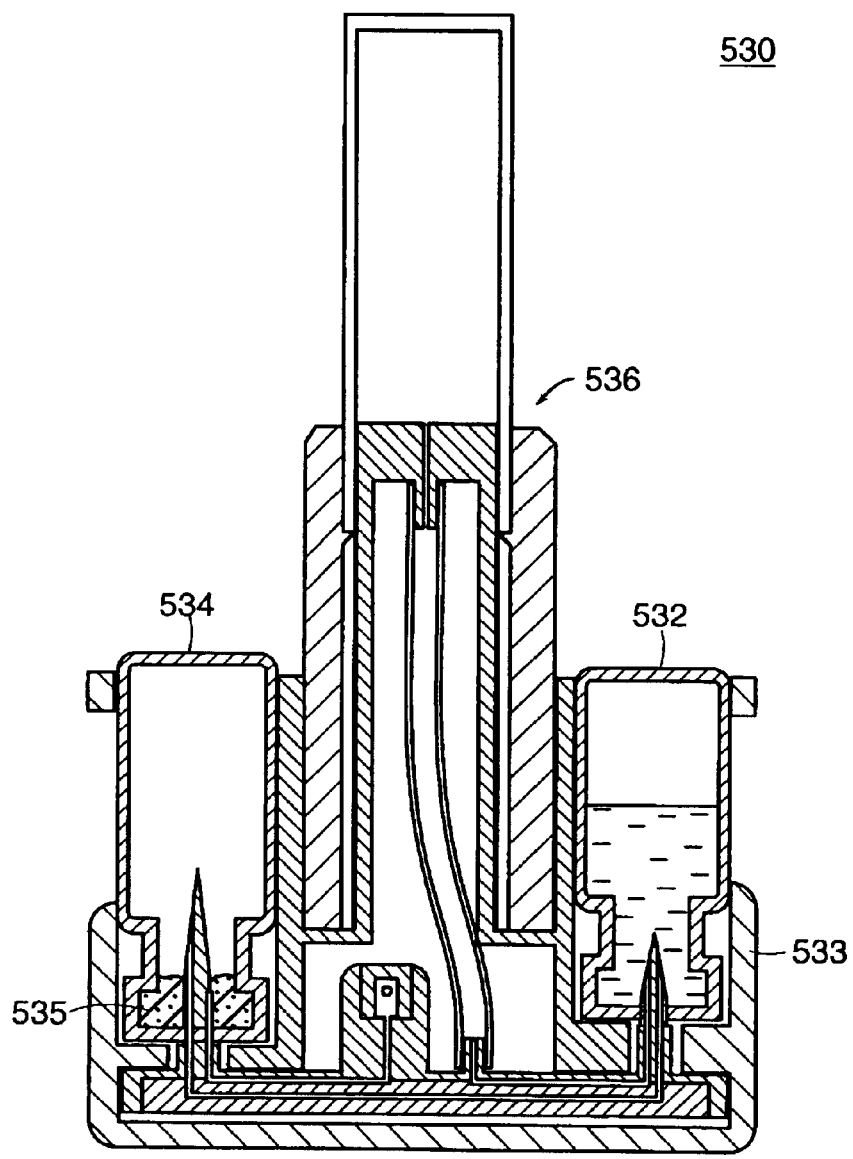
FIGS. 22A–22E illustrate cutaway and perspective views of an alternate embodiment of the drug delivery system in accordance with the present invention.
Figure 22B:
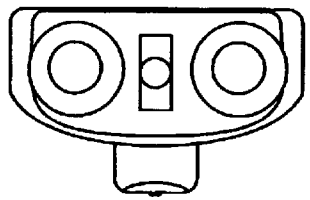
Figure 22C:
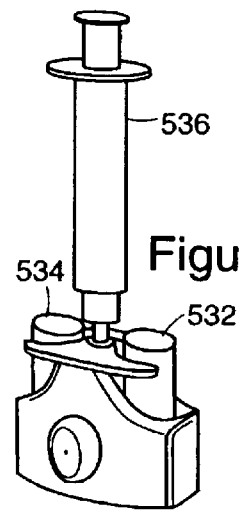
Figure 22D:
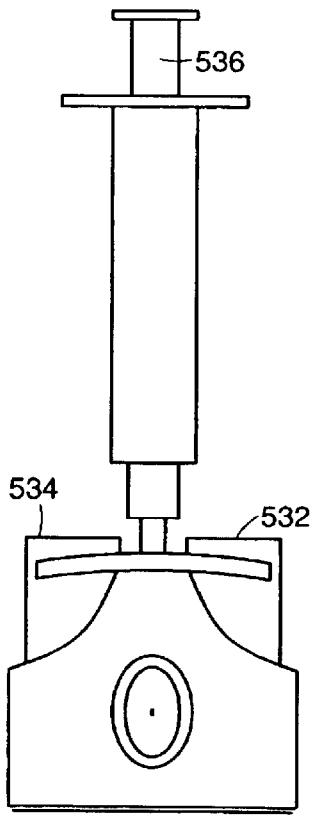
Figure 22E:
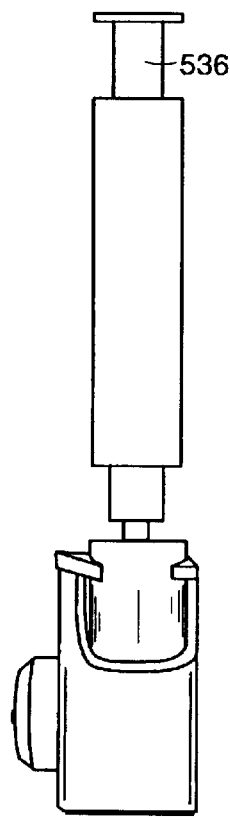
Figure 23A:
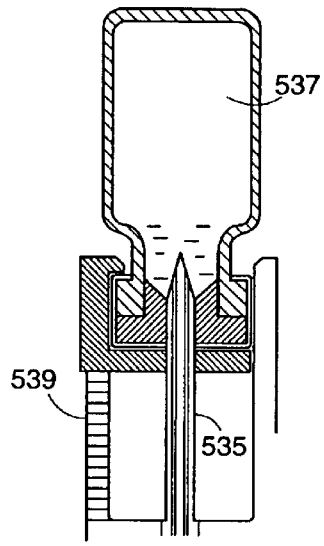
FIGS. 23A and 23B illustrate alternate preferred embodiments to control the dose of drugs in accordance with the present invention.
Figure 23B:
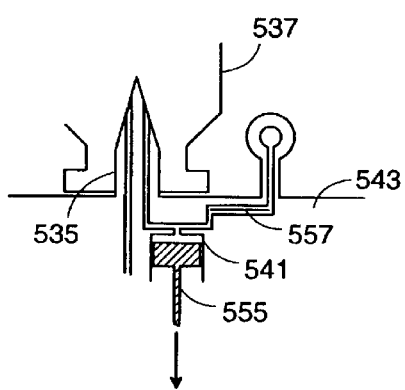

Referring to FIGS. 22A–22E, the views illustrate an alternate preferred embodiment of the drug delivery system 530 in accordance with the present invention. This particular embodiment may be used as a reconstituted system and a drug delivery system and includes two vials 532, 534 a first containing a diluent 533 and a second containing the lyophilized drug 535. In addition, there is an air delivery system for pressurizing system, such as a built-in air cylinder 533 in fluid communication with the diluent vial 532 which is disposed between the lyophilized drug vial 534 and the diluent vial 532. Air is pushed into the diluent vial 532 forcing the diluent 533 from its vial into the lyophilized drug compartment or vial 534. After reconstitution is completed, the liquid drug is ready for injection. A hydrophilic membrane is used as an air separator to minimize or preferably prevent the entry of air into the user's tissue. This particular embodiment uses a straight needle 402 injector system as described with respect to FIGS. 18A–18C. Additionally, a positioning interlock, such as the mechanism, described with respect to FIGS. 2A–2B is used. Further, in an alternate embodiment, the air cylinder can be replaced with a standard syringe to be the air source as shown in FIGS. 22D and 22E. A check valve (as shown in FIG. 16) disposed in the air inlet between the syringe and manifold is included in the embodiment containing the syringe. The drug delivery system of the present invention is used to deliver an accurate volume of a drug solution. The predetermined volume can be delivered using different methodologies. A first embodiment controls the dose by changing the height of the outlet spike 535 in the liquid drug vial 537 as shown in FIGS. 23A, i.e. the higher the spike, the lesser is the amount of drug transferred out of the vial 537. The spike is adjusted by means of threads 539 upon which the spike rotates or upon which it sealably slides. This can be used for to transfer or to inject the drug solution. Another preferred embodiment which increases the accuracy of the volume of drug delivered uses the residual drug volume as a parameter to indicate the volume delivered. One way of controlling delivered drug solution volume is to use the assembly shown in FIG. 23B. After the drug is pushed in solution in vial 102 the solution may be pulled into cavity 541 by piston 555. The cavity 541 has indications thereon to aid the user in determining the proper volume. At the desired level, the piston is stopped. The drug solution is then transferred from the cavity 541 either via a needle into a user or into a drug delivery device. Yet another embodiment to provide an accurate volume of drug is disclosed with respect to FIGS. 24A–24C and FIG. 25. The reconstitution system having the vial containing the reconstituted drug is essentially used as a filling station by a detachable delivery device, for example, a standard syringe or a pen type pump.

Figure 24A:
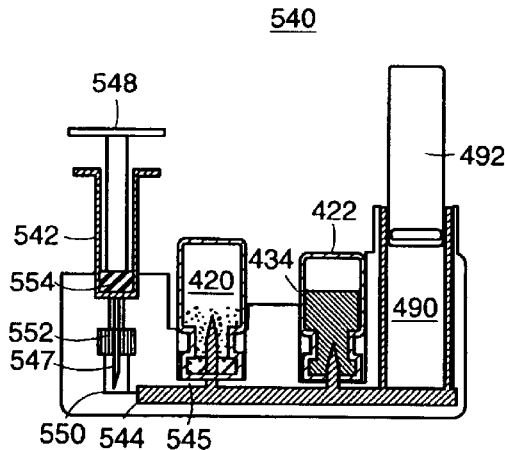
FIGS. 24A–24C illustrate cutaway views of an alternate embodiment of the drug delivery system in accordance with the present invention incorporating filling devices, for example a syringe, to inject the drug system.
Figure 24B:
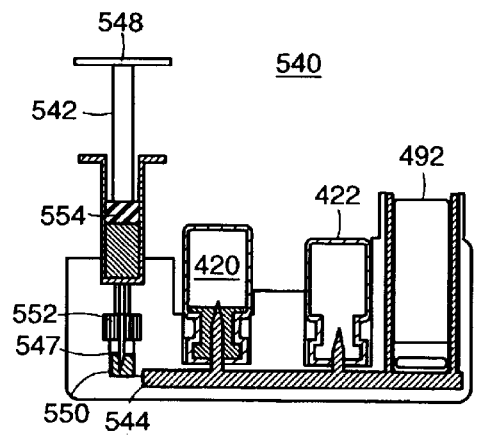
Figure 24C:
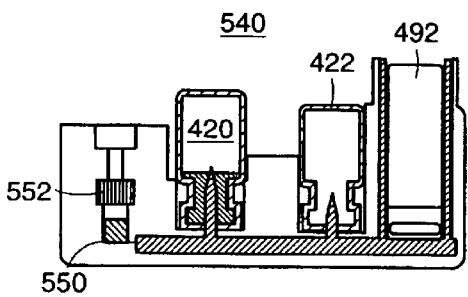

Referring to FIGS. 24A–24C a position independent injector system 540 is illustrated. The drug 545 is reconstituted similar to the description provided with respect to earlier systems such as illustrated in FIG. 19F. After the drug has been reconstituted it can be aspirated by a conventional standard syringe 542 for the exact dose required. The accuracy using this method is about +/−5%. The fluid level in the cavity 550 is controlled by adjusting the pressure and geometry of the device 540. The needle is held in place by the elastomeric septum or stopper 552. In use, once the reconstituted drug is aspirated into the syringe 542 by moving plunger 548 which moves the stopper 554 upwards allowing the syringe 542 to be filled with the liquid drug, the syringe 542 is removed from the drug delivery device 540. The accuracy of the volume of the liquid drug delivered is determined by the scale on the syringe. The user then injects the drug and disposes of the syringe by one of several potential ways. One of the ways of disposing the syringe is by attaching the syringe to the open cavity 550 left in the drug delivery device 540. A second way is by securing the needle 547 prior to disposing the syringe by locking it with a piece of plastic tubing. The system 540 and procedure used is free of air inclusions and does not require an air separator. The syringe needle 547 is placed in a closed cavity penetrating a septum 544 and thus allows for fluid communication between the needle 547 and the reconstituted drug. The volume of the closed cavity is designed to ensure the availability of the liquid drug to the needle 547 under controlled pressurized conditions. The position of the syringe piston 548 is fixed under pressurized conditions and the dose is manually aspirated from the syringe.

Figure 25:
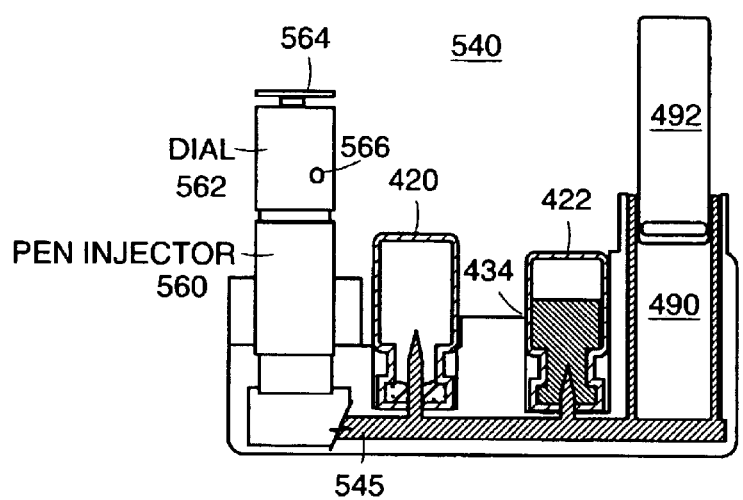
FIG. 25 illustrates a cutaway view of an alternate embodiment of the drug transfer system in accordance with the present invention incorporating filling devices, for example a pen type pump to inject the liquid medicament.
Figure 26A:
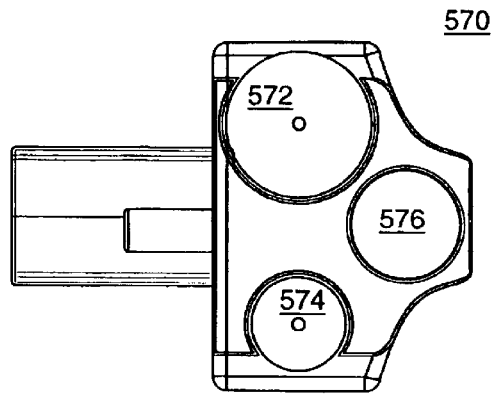
FIGS. 26A–26D illustrate perspective views of a preferred embodiment of a drug transfer system in accordance with the present invention.
Figure 26B:
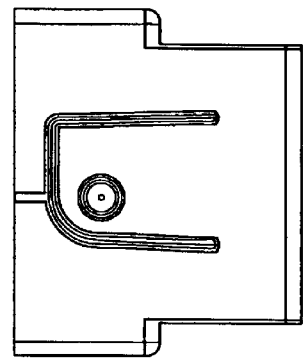
Figure 26C:
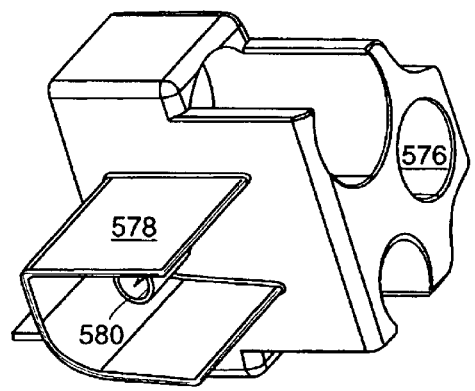
Figure 26D:
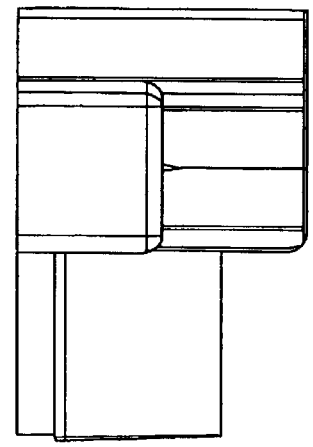

Referring to FIG. 25 an alternate preferred embodiment of the drug delivery system 540 as described in FIGS. 24A–24C is illustrated. The reconstitution stage is similar to the one described with respect to FIGS. 24A–24C. However, the injector system including an attachable delivery device is different. The user dials or tunes the required dose using a pen type pump 560 that includes a dial 562 that is inserted into the drug delivery device. The dialing process retracts a floating piston which moves upward and creates an internal pressure which provides for aspiration of the reconstituted drug. A trigger 564 releases a preloaded spring to push the floating piston. Thus aspiration occurs by dialing the dose into the pen-type injector.

Once the pump 560 is filled as indicated by an indicator 566, it is disconnected from the filling device. Injection and disposal of the pump is performed after disconnection with a process similar to the process described with respect to FIGS. 2A–24C.

FIGS. 26A–26D are perspective views of a drug transfer system having a drug delivery device 510 in accordance with the present invention. A diluent vial is inserted in a cavity 572 and a lyophilized drug vial is inserted in cavity 574. A cavity 576 accommodates an air pressurization system to deliver drugs having a low level of viscosity. Further, the drug transfer system includes an access 578 to receive a drug delivery device. The drug is transferred thereto via a needle 580.

Figure 27A:
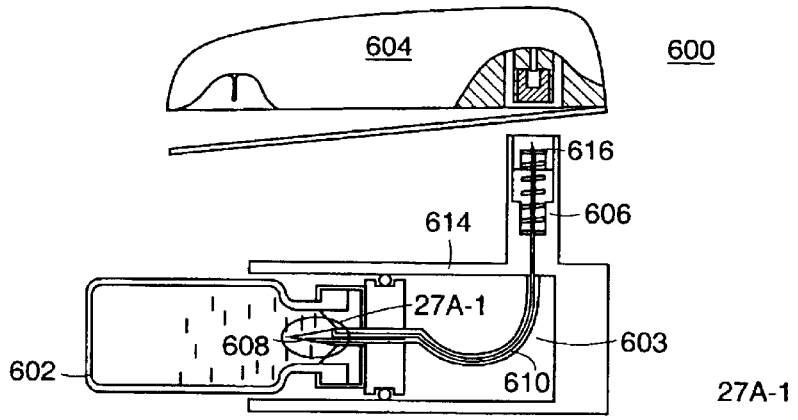
FIGS. 27A–27C illustrate cutaway views of a preferred embodiment of a drug delivery system in accordance with the present invention.
Figure 27B:
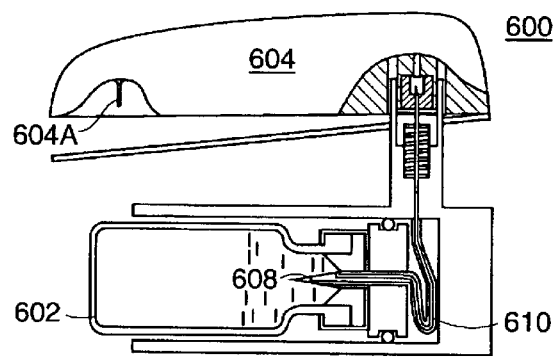
Figures 1, 27A:
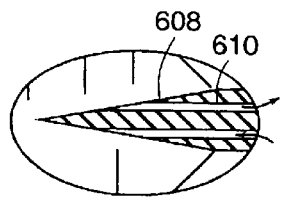
Figure 27C:
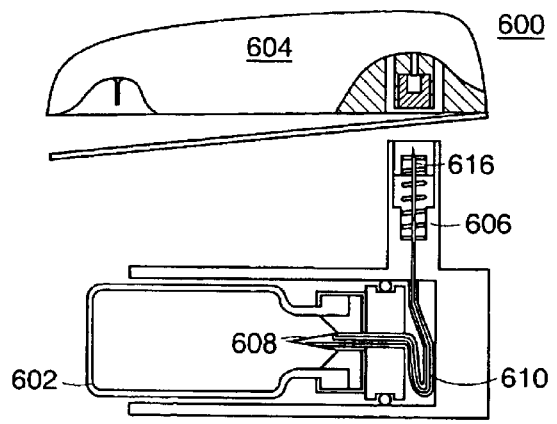

FIGS. 27A–27C are cutaway views of a preferred embodiment of a transfer system 600 in accordance with the present invention. Once pressurized by the air in cavity 603, the liquid drug from vial 602 is transferred to a drug delivery device 604 via an extension 606. The liquid drug flows out of the vial 602 through spike 608 and through the tubing 610 into the needle 616 which is received into the drug delivery device 604.

Referring to FIG. 27B, the drug delivery device 604 is attached to the transfer system 600. The filling process continues until the entire drug level reaches the outlet 604A (shown in phantom in FIG. 26B) of the device 604. At this point the filling process is completed. It should be noted that during the filling process, if the user stops pushing the vial 602 into the transfer system 600 the drug may drain into the cylinder 614. This is prevented by getting the friction forces higher than the impedence of the tubing 610 to the drug flow. In the alternative, it is also possible to dispose a one-way valve at the end of the tubing 610. Once the drug delivery device 604 is filled with a liquid drug, it is disconnected from the transfer system 600. Any residual drug in the system 600 can stay protected, and the needle 616 is retracted and as described earlier with respect to the needle locking mechanisms is secured in the cover 606, and cannot be reexposed to cause harm or injury.

FIGS. 28A–28C are cutaway views of the operation of another preferred embodiment of a drug delivery system 630, in particular of a position independent injection system in accordance with the present invention. In this embodiment, the injection system 630 is position independent, that is the injector is not required to be in a vertical position during the injection process. Referring to 28A, the drug delivery system 630 includes a vial 632 containing the liquid drug 634. The liquid drug 634 flows through the spike 636 along a tube 644A into a cavity 652. The spike includes two paths, one path 642 for delivering pressurized air into vial 632 from chamber 641 and another path 644 to deliver the liquid drug to the user via a needle 664. The liquid drug exits from the path 644 and travels along tube 644A disposed at the bottom of the spike. A one-way valve 638 insures the unidirectional flow of the liquid drug 634 into the cavity 652A. Spring 640 holds piston 656 within the cavity 652. A floating piston 650 moves in the cavity 652. A seal 654 is included in the floating piston. Member 660 rests atop a needle assembly 664A. Member 660 is hingedly connected to member 662. Member 662 has a finger 662A. Prior to use, the finger 662A rests within an aperture 662B of the housing 660A. The notch 658 is the end of travel position for the piston 656.

The path 642 from the air chamber 641 to the vial 102 pressurizes the vial by delivering air thereto. The air chamber 641 is depleted of air when the vial is moved downward. As the vial moves downward, a member 641A sealably slides within the walls of the chamber and forces the air into the vial. The member 641A is prevented from leaking air out of the chamber by the seal 641B.

In use, when vial 632 is pushed into the device 630, air from the cavity 641 enters into the vial 632 and pressurizes the liquid drug. This drug 634 under pressure flows via path 644 through the one-way valve 638 into the left side of the cavity 652. Pressurized air pushes the floating piston 650 to the right side of the cavity 652. The floating piston 650 moves until the position of the notch 658, which is the end of travel position for the piston 656 and thus for filling of the cavity 652. Thus, as illustrated in FIG. 28B, an accurate volume of liquid drug is filled in cavity 652 and the device 630 is ready to be used.

As illustrated with respect to FIG. 28C, once the member 660 is depressed, it causes the needle 664 to move downwardly outside the housing 660A and into the user's tissue. Member 662 is hingedly connected to member 660. When 660 is depressed, it causes member 662 to move upwardly disengaging the finger 662A from the aperture 662B and enables the spring 640 to return to a less compressed state. As it does, the spring 640 forces the piston towards the opposing end of the cavity 652. This causes the liquid drug therein to move via channel 652A and needle 664 into the user's tissue, the piston 656 is released due to the movement of member 662 in the upward direction. The piston 656 moves to the left. The floating piston 650 is under pressure and moves the liquid drug in cavity 652 through the injector needle 664 and into the user. It should be noted that after delivery of the liquid drug, the position of the floating piston 650 depends on the load on the spring 640. To prevent the flow of residual drug under pressure, the spring 640 continues to be in a preloaded state. The seal 654 is pushed to the left side of the cavity 652 under pressure of spring 640 to seal against the exit of the pressurized residual drug via the channel 652A. Although disclosed as having a pushing spring 640, other mechanisms may be included in the injector system to result in a position independent injector.

Figure 28D:
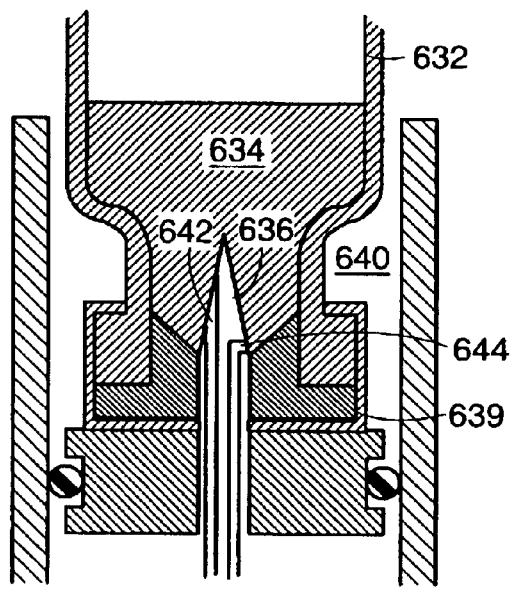
FIG. 28D illustrates an enlarged cutaway view of a preferred embodiment of the spike which brings the liquid drug in communication with the delivery system in FIGS. 28A–28C.

Referring to FIG. 28D, a cutaway view of a spike 636 which brings the liquid drug 634 in fluid communication with the injector system is illustrated. The spike 636 penetrates the septum 639 of the vial 632 when the vial is inserted into the cavity 640. The spike functions as a piston 641A and is sealably and slidably movable by means of the seal 641B within the interior walls of the chamber 641. As described hereinabove, the spike also consists of two paths, an air inlet 642 and a drug outlet 644. Once the vial 632 is inserted, pressurized air enters the vial 632 from an air chamber 641 and forces the liquid drug 634 via a flexible tube 644A to the injector system. The filling process for the injector system in a preferred embodiment is preferably done under a maximum pressure gradient of 0.3 bar. This includes a margin for example, priming at an altitude of 5,500 feet and is the maximum expected back pressure.

Figures 1, 29A:
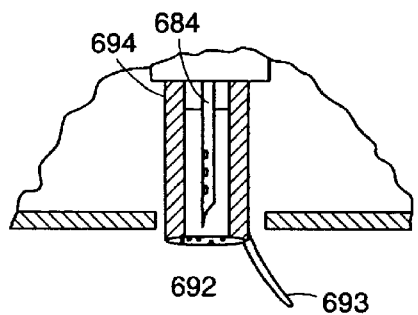
FIGS. 29A and 29B illustrate partial cutaway views of a preferred embodiment of the drug transfer delivery system in accordance with the present invention.
Figure 29A:
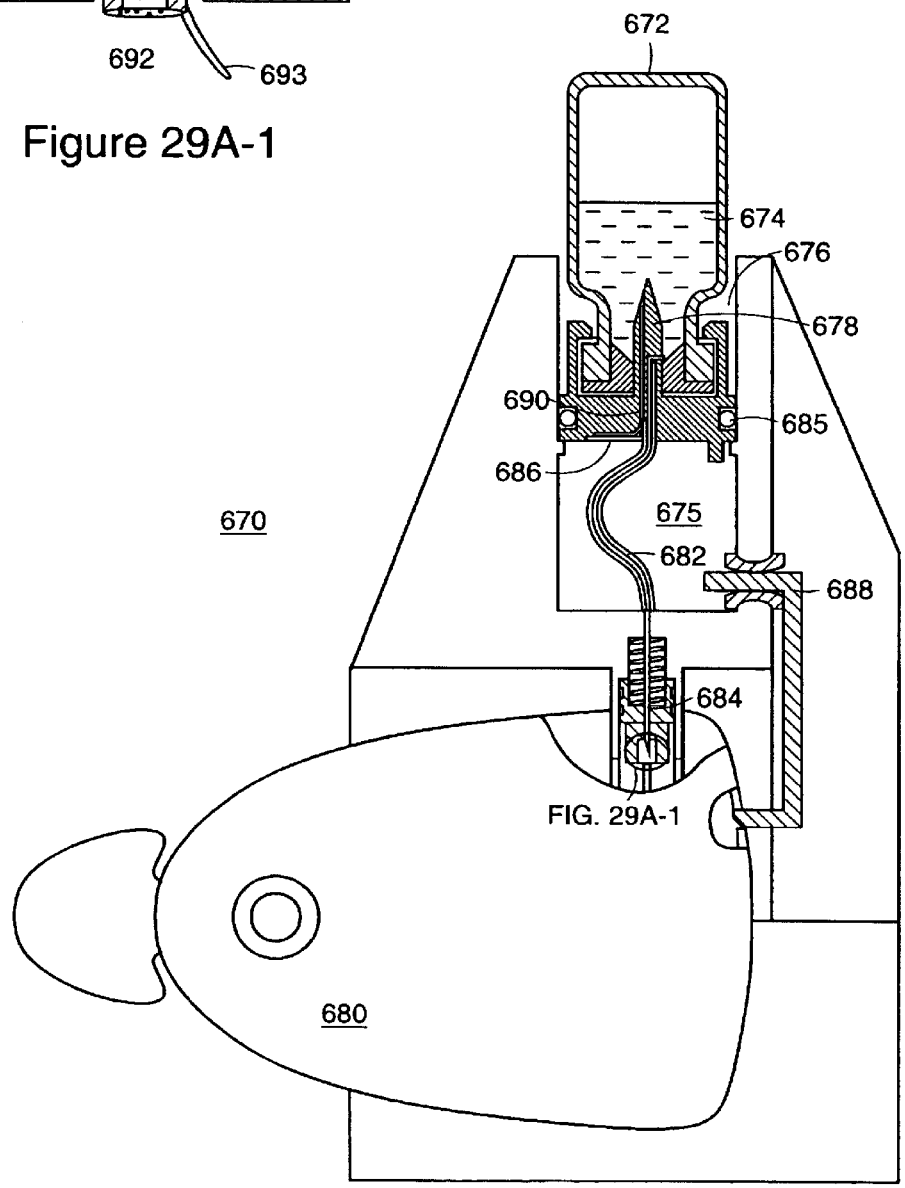
Figure 29B:
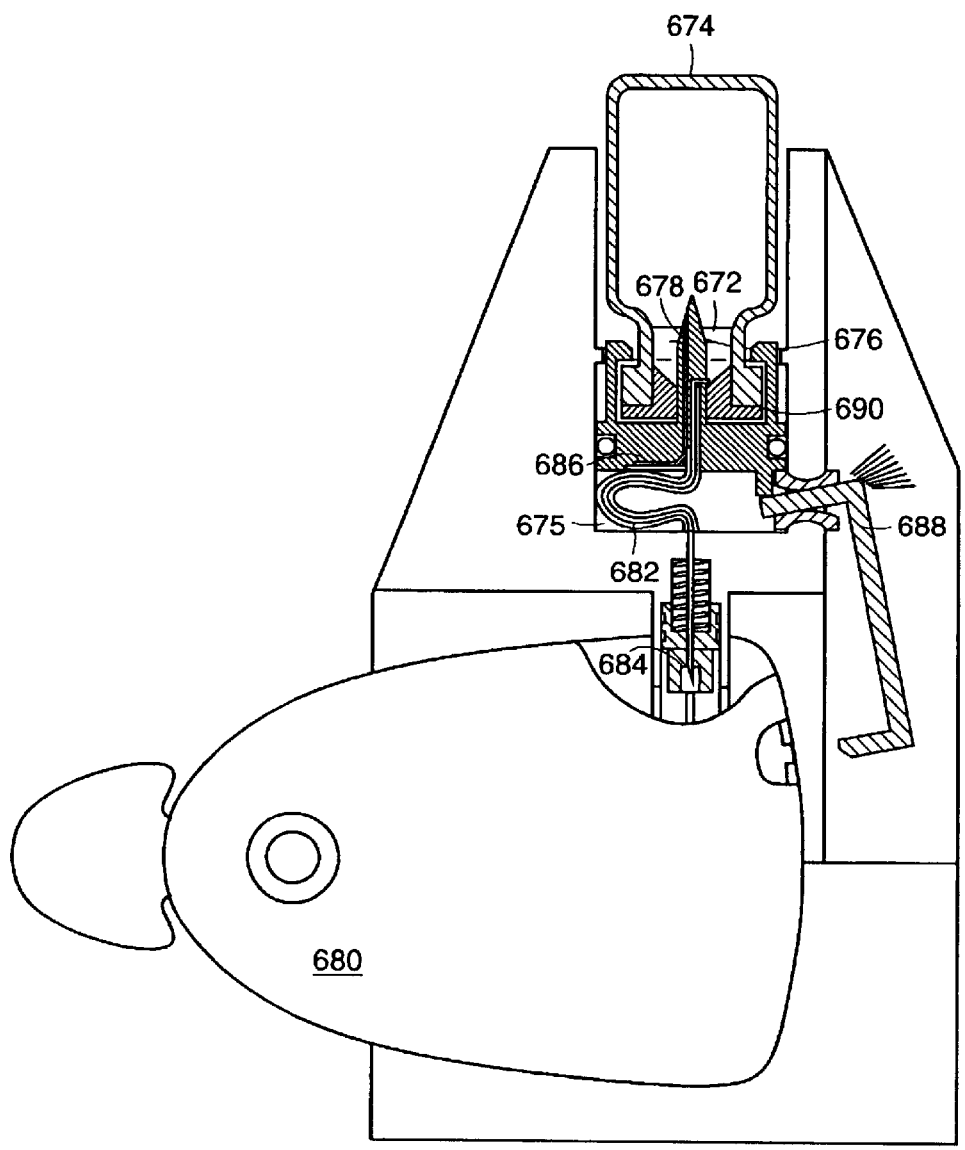

FIGS. 29A and 29B illustrate partial cutaway views of another preferred embodiment of the drug transfer system 670 in accordance with the present invention.

The drug vial 672 containing the liquid drug 674 is inserted into a cavity 676. A spike 678 provides air into the liquid drug vial 672 for pressurization of the drug 674 and additionally the spike provides for an outlet for the liquid drug to be delivered to a drug delivery system 680. The drug transfer system 670 is in fluid communication with the liquid drug vial 672 through a flexible tubing 682 and a needle 684.

A hydrophobic membrane 686 is disposed in the flexible tubing 682 to prevent the transfer of air into the drug delivery system. This hydrophobic membrane 686 prevents back flow. The air to pressurize the liquid drug 674 is provided by air in the reservoir 675. Further, a latch mechanism 688 secures the vial 672 to the detachable delivery system 680 during a filling process.

Referring to FIG. 29A-1, an enlarged view of the interface between the drug transfer system 670 and the detachable drug delivery device 680 is illustrated. A hydrophobic membrane 692 is disposed at the interface for blocking the flow of the drug once the drug delivery device 680 is filled. An elastomeric cover 694 is disposed around the needle 684 for protection against the needle 684. Tab 693 is pulled off to remove the hydrophobic membrane 692 prior to use of the device 680.

In operation the liquid drug vial 672 is pressed into the cavity 676 which causes the air in the reservoir 675 to be compressed and enter the liquid drug vial 672. Air is prevented from leaking out of the cavity 675 by means of seal 685. The liquid drug 674 is pressurized and delivered through the spike outlet 690. Residual air from the air reservoir 675 is vented from an opening in the latch mechanism 688 once the latch is disengaged from the drug delivery device at the end of travel of the vial and subsequent end of the transfer process.

Figures 30A, 30B:
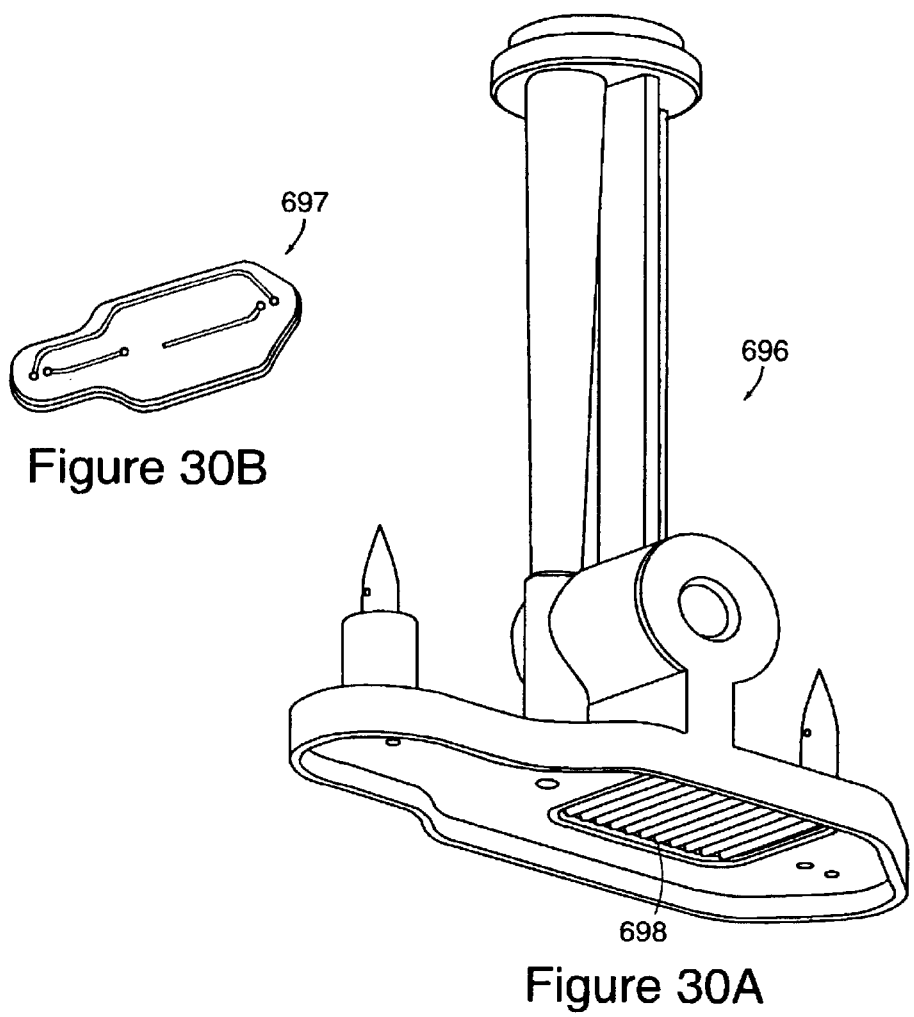
FIGS. 30A and 30B are views showing the two piece construction of the manifold in accordance with the drug delivery system of the present invention.

Referring to FIGS. 30A and 30B, the two piece 696, 697 construction of the manifold in accordance with the present invention is illustrated. The manifold is a biocompatible material such as, for example, polycarbonate or acrylic or pvc molding having a gas impermeable membrane 698 welded in the part 696. The two pieces 696, 697 are ultrasonically welded together.

Referring to FIGS. 31A–31E, perspective views illustrate an alternate preferred embodiment of a drug delivery system 700 in accordance with the present invention. This particular embodiment maybe used with the reconstituted drug delivery system and includes two vials 702 and 704, a first containing a diluent and a second containing a drug that needs to be reconstituted. In addition there is a pressurizing system, such as a built-in cylinder 706 in fluid communication with the diluent vial 702. The built-in pressurization system such as the cylinder 706, is disposed between the lyophilized drug vial and the diluent vial. A plunger 708 is slidably received into the cylinder 706 to provide the necessary air pressure to effect drug transfer. Air is pushed into the diluent vial forcing the diluent from its vial into the lyophilized drug compartment or vial 704. As discussed previously, a hydrophilic membrane is used as an air separator to minimize or preferably prevent the entry of air into the user's tissue. In use, a diluent vial is inserted into the drug delivery system 700 followed by the insertion of a drug vial. The plunger 708 is pushed downwards to pressurize the air in the cylinder 706 and deliver it to the diluent vial 702. Once the diluent solution is pressurized it is delivered to the drug vial 704 to reconstitute the drug. Pressing the knob mechanism 710 displaces an injection needle which is used to inject the reconstituted drug into a user tissue. The depression of the knob mechanism and subsequent injection is similar to that described earlier with regard to either the straight needle assembly shown in FIG. 18 or the U-shaped needle shown in FIGS. 11, 13 through 17.

Figure 31A:
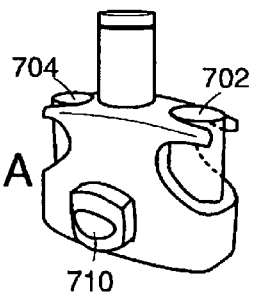
FIGS. 31A–31G are perspective views of a preferred embodiment of a drug delivery system in accordance with the present invention.
Figure 31B:
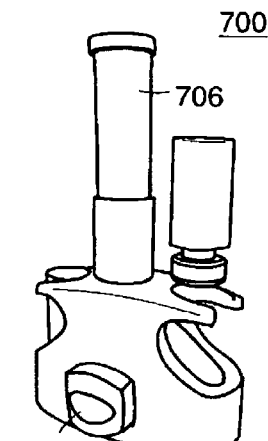
Figure 31C:
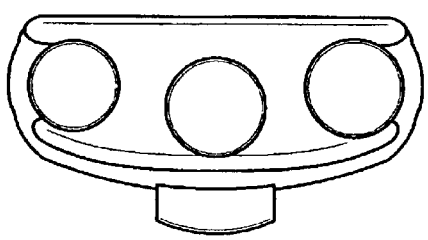
Figure 31D:
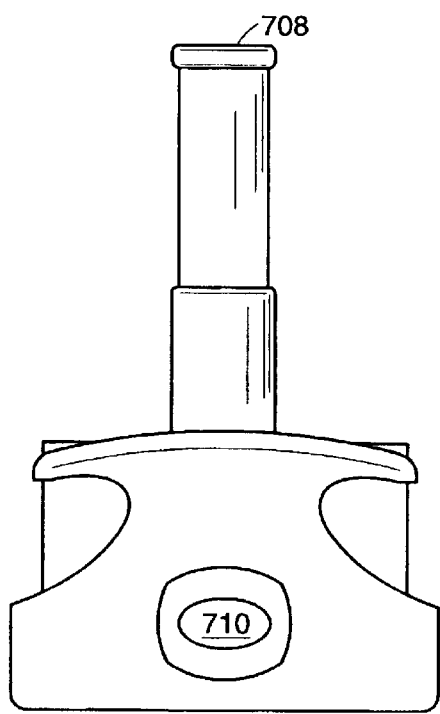
Figure 31E:
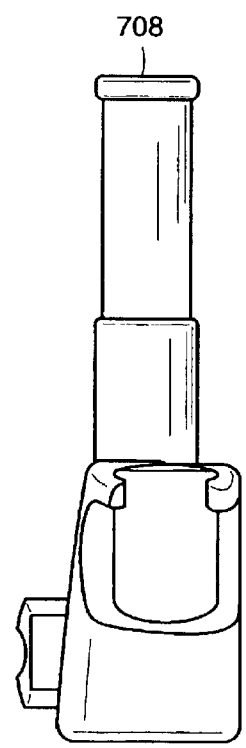
Figure 31F:
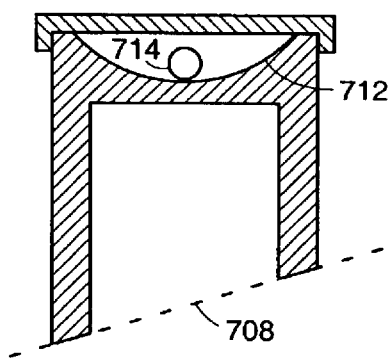
Figure 31G:
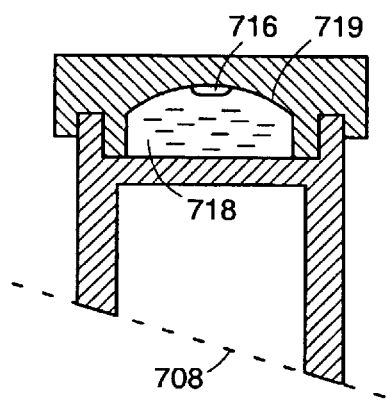
Figure 32A:
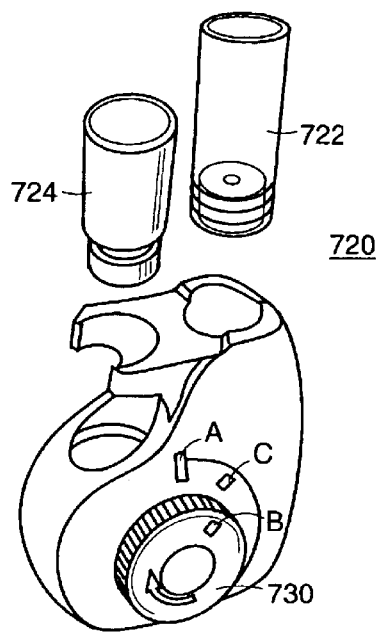
FIGS. 32A–32E are perspective views of another preferred embodiment of a drug delivery system in accordance with the present invention.
Figure 32B:
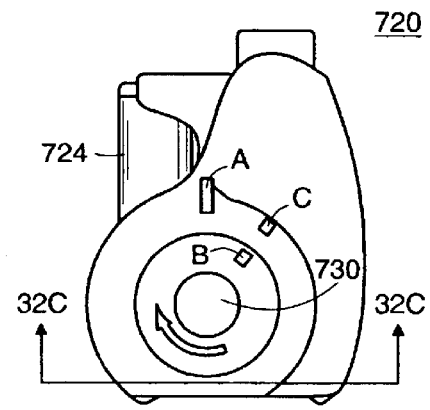
Figure 32C:
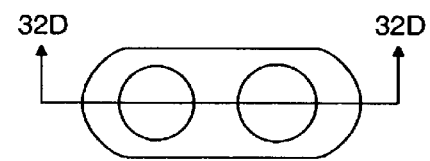
Figure 32D:
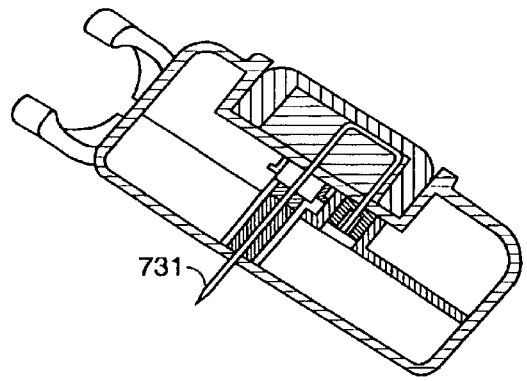
Figure 32E:
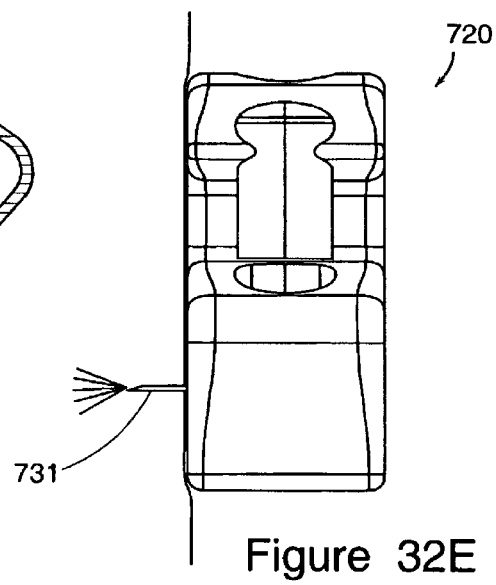

Referring to FIGS. 31F and 31G, two preferred embodiments 711, 713 which provide a visual indication of device orientation are illustrated. The vertical indicators 711, 713 are shown as being disposed on the top of the plunger 708, however their location can vary to provide appropriate visual indication. In the first embodiment of the vertical indicator 711, a metal ball 714 rests upon a curved surface having visual indicators or scale 712 thereon. The ball 714 is enclosed within a clear casing 712A. The positioning of the ball 714 in the middle of the scale is an indication of vertical orientation. In the second embodiment 713 of the vertical indicator, an air bubble 716 disposed in a liquid 718 enclosed within a clear housing 718A is used as the visual indicator of orientation with respect to the scale 719. The positioning of the air bubble 716 in the middle of the scale is an indication of vertical orientation.

Referring to FIGS. 32A–32E, perspective views illustrate a further alternate embodiment of the drug delivery system 720 in particular a reconstitution and injection system, in accordance with the present invention. In this embodiment the reconstitution of the drug occurs by the mixing of the diluent solution with the drug. A separate pressurization system for the diluent is not required for this particular embodiment and can only be used with low viscosity drugs. In use, the knob 730 is moved in a counter clockwise direction to begin the reconstitution process of the drug which opens a pathway connecting the diluent with the drug. The knob 730 is turned from a non-use position (as indicated when notches A and B align) to a ready to use position as indicated with the alignment of notches B and C. At this point, the knob 730 may be depressed and the solution injected. The internal pressure of the diluent vial and gravity cause the diluent to transfer to the vial containing the drug. Further movement of the knob or dial 730 activates an injection needle which interfaces with the user's tissue to deliver the reconstituted drug. Again, the injection assembly is similar to the embodiments shown in FIGS. 11, 13–17.

Figure 33D:
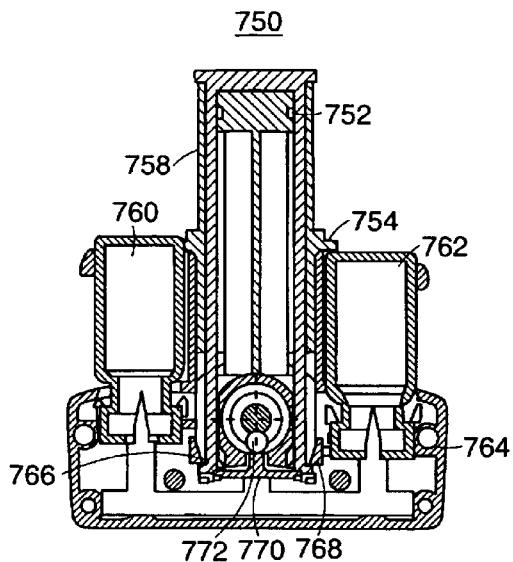

Referring to FIGS. 33A–33I, cutaway views of preferred embodiments of the drug delivery system emphasizing the interlocks disposed to provide for a safe system are illustrated. Referring in particular to FIGS. 33A and 33B, the interlocks as required during shelf life of the drug delivery device 750 are illustrated. The end of the cylinder 752 has a biasing lip 766 extending outward to matingly fit with wall 758 and the lip must be flexible enough to bend with the pressure of wall 758 when vials are inserted in the assembly. During shelf life the cylinder 752 is secured by latch 754 and mating lip 756. This mating fit prevents the movement of the movable cylinder 752 in the vertical direction prior to use. As previously described, the cylinder 752 provides pressurized air to the drug delivery system 750. The movement in the downward direction of the cylinder 752 is minimized or preferably prevented by holding the latches 754 and 756 on the wall 758. An upward movement of the cylinder 752 is prevented by latch 754.

Referring to FIG. 33C, the next step includes the insertion of the vials 760 and 762 into the device 750. Only after the insertion of both vials 760, 762 is the cylinder 752 free to be pushed in the vertical direction. The insertion of the vials forces the lip 766 inward enabling it to clear the wall 758 and thus enable the cylinder 752 to move downward. In addition, the latches 754 secure the vials in the device 750.

Figure 33E:
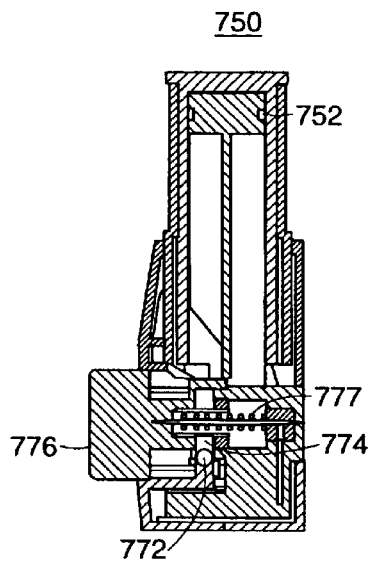

Referring to FIGS. 33D and 33E, the interlocks that play a role once the cylinder 752 is pushed as illustrated. The cylinder 752 is pushed downward until the end of travel position and is locked by the mating of lip 766 and interlock element 768. Again, as described above with regard to pre-use, the lip 766 moves downward and catches on element 768 and moves to a radially expanded position which prevents the cylinder from travelling upward again. A locking element 768 keeps the cylinder in the bottomed out position. The element 768 is formed as a part of the wall 758.

In the area where the drug solution is injected there is a pushing member that moves in a relative perpendicular fashion to the direction of travel by the cylinder. A ball 772 is positioned prior to use within the housing to prevent depression of the member 776. When the cylinder is fully depressed, the lip 766, pushes a member 770 which allows the ball 772 to drop into a groove 774 making the movement of the pushing member 776 possible only if the device is in a vertical orientation.

Figure 33F:
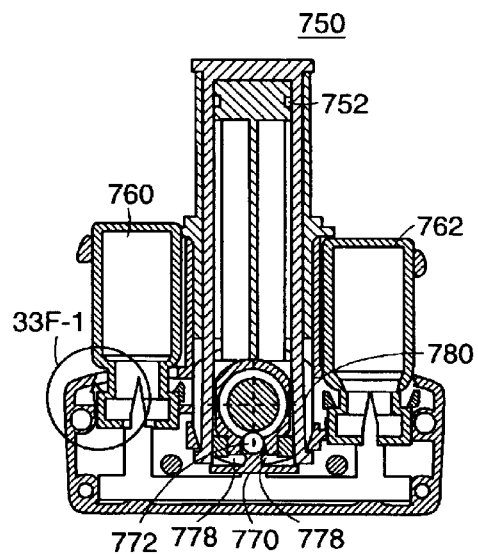
Figure 33G:
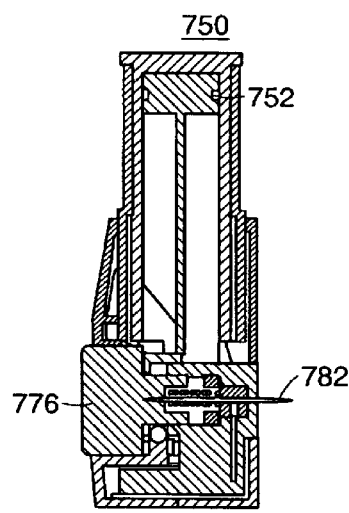
Figures 1, 33F:
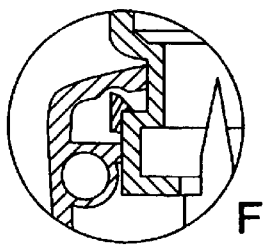

Referring to FIGS. 33F and 33G, during the injection process different interlock elements insure the safe use of the drug delivery system. As the pushing member 776 is depressed, which is only allowed if the drug delivery system 750 is in a vertical orientation, the horns 778 spread the latch 780 which allows the member 770 to press the ball 772 in the upward direction. Note the pushing member 776 is already pushed to expose the needle 782.

Figures 33H, 33I:
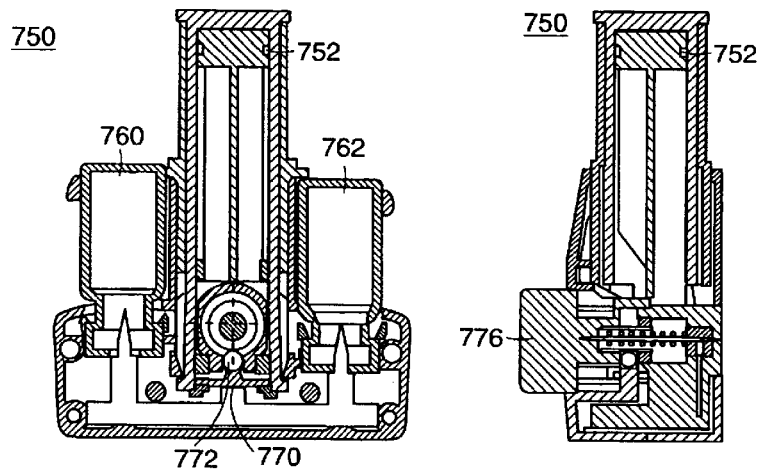

Referring to FIGS. 33H and 33I, the interlocks during the phase of disposing of the drug delivery device which follows the injection phase are illustrated. The pushing member 776 is released by the action of the spring 777 pushing the member 776. Since the movement of the ball 772 was limited by the body of the member 776, with the release of the member 776, the ball 772 can now move back into the groove 774 as it is assisted by the pressure applied by the rear shell latch 780. This locks the pushing member 776 into position thereby preventing further use of the drug delivery device 750.

Referring to FIGS. 34A through 34D, a preferred embodiment of the drug delivery device having an end of delivery indicator is illustrated. As discussed previously with respect to preferred embodiments of the drug delivery system of the present invention, the drug delivery system is activated by pressurized gas, for example, air. The air forces the drug to the injection site by pressurizing the drug. A hydrophillic membrane minimizes and preferably prevents the passage of air into the user's body. The hydrophillic membrane is disposed in the drug path to the user's tissue. Once wetted, the hydrophillic membrane allows liquid drug to proceed into the user's tissue and stops the passage of air into the user's tissue. In order to insure the effectiveness of the membrane, the hydrophillic membrane has to become wetted. To enhance the effectivity of the drug delivery device, a hydrophobic membrane is also positioned in the drug path. Referring to the FIGS. 34A and 34B, an inlet 800 which provides the liquid drug 802 into a cavity 803 has both a hydrophobic membrane 806 and a hydrophillic membrane 810 disposed therein. The hydrophobic membrane 806 allows air to pass, but stops liquids. On the other side of the cavity 803 the hydrophillic membrane 810 allows liquid drug to pass while stopping the flow of gas. At one end of the hydrophobic membrane 806 a flexible elastomeric diaphragm is disposed that acts as an indicator once filled with gas, for example, air. The membrane being flexible, once filled with air gives an external indication for end of delivery.

Figure 34A:
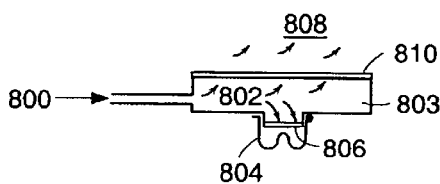
FIGS. 34A–34D are views of a preferred embodiment illustrating an end of delivery indicator of the drug delivery system in accordance with the present invention.
Figure 34C:
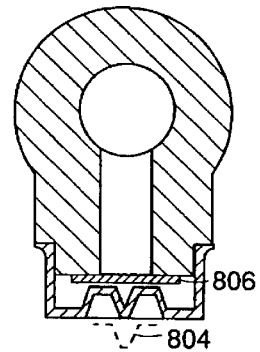
Figure 34B:
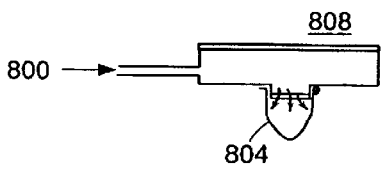
Figure 34D:
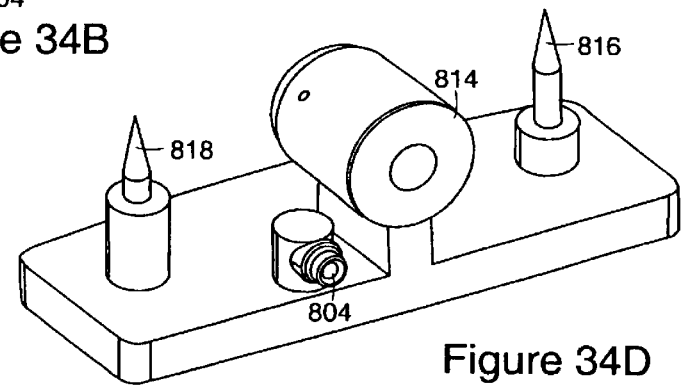

The presence of air occurs only once the liquid drug has been delivered. It should be noted that the hydrophillic membrane 810 is disposed close to the injection site as it allows liquid to go through to the injection site minimizing or preventing the flow of gas into the user's tissue. FIG. 34D illustrates a manifold structure utilizing the end of delivery indicator 804 built into the manifold. The septum 814 surrounds a cavity containing the liquid drug. The spikes 816 and 818 interface with the elastomeric stoppers of vials containing a diluent and a medicament.

Figure 35:
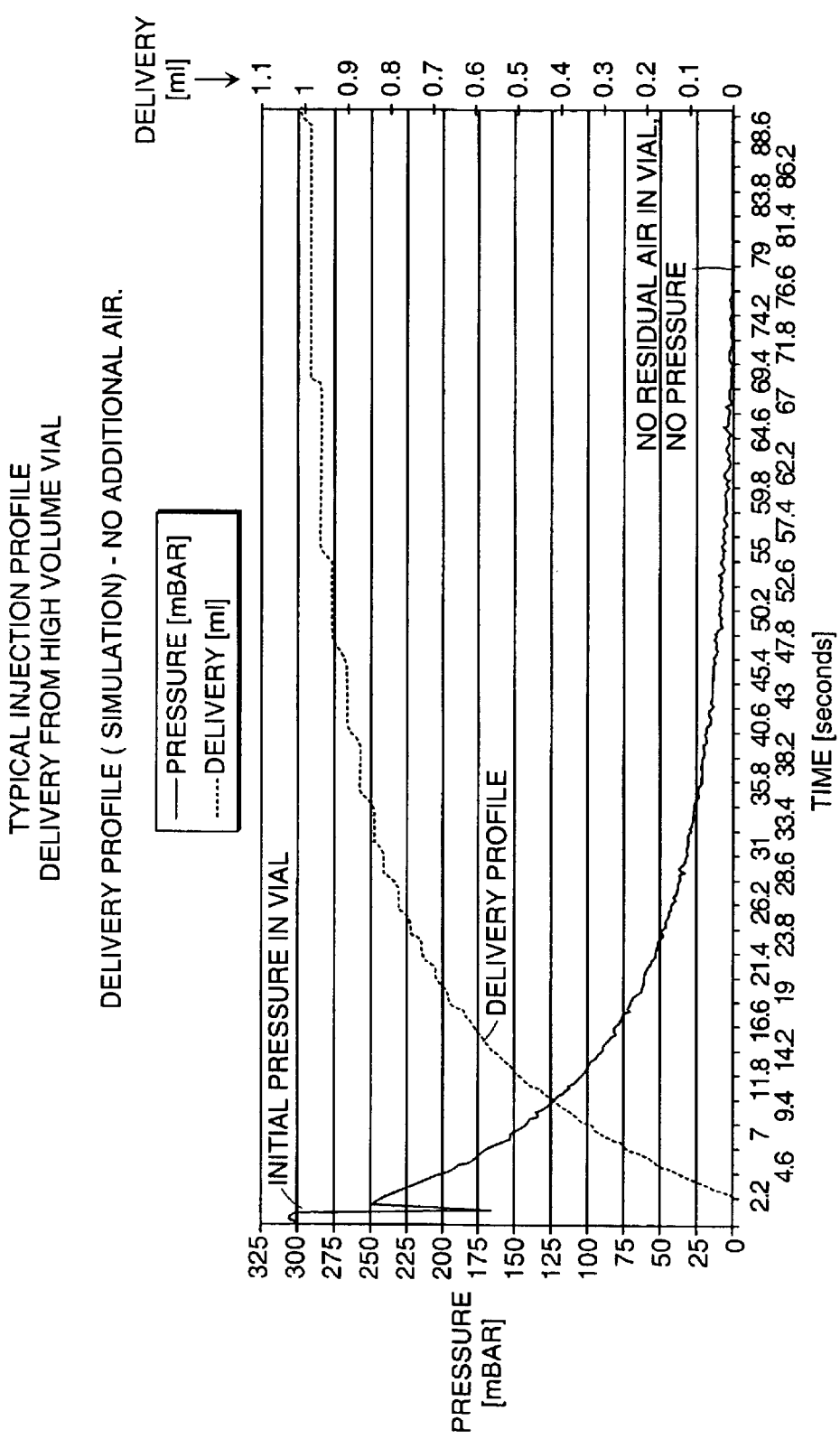
FIG. 35 is a graphical illustration of a delivery profile of a preferred embodiment of the drug delivery system with no additional volume of air in the liquid vial in accordance with the present invention.

FIG. 35 graphically illustrates the delivery profile from a high volume vial having no additional air pressure in the vial. The profile illustrates pressure (in millibars) versus time (in seconds). The initial pressure in the vial is in the order of about 300 millibars which decreases during the delivery process to approximately 0 millibars at the end of delivery process. This is in contrast to the pressure in a vial that initially contained approximately 3 milliliters of air as illustrated with respect to FIG. 33. As a result, there is no residual air pressure in the vial once delivery is complete. The delivery process spanned a time period of approximately 86.4 seconds.

Figure 36:
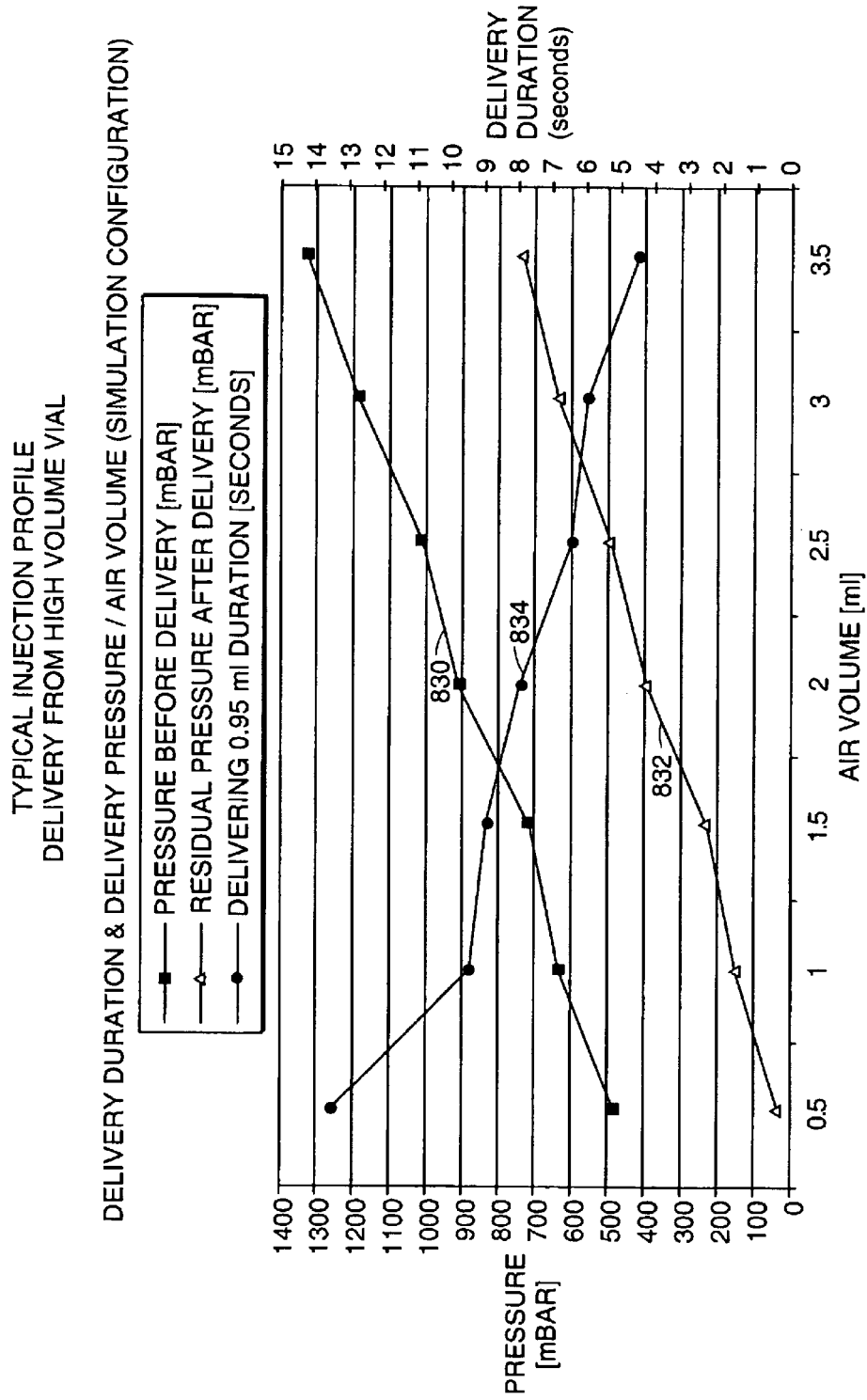
FIG. 36 is a graphical illustration of the delivery duration and delivery pressure of a preferred embodiment of the drug delivery system in accordance with the present invention.

FIG. 36 graphically illustrates delivery duration and delivery pressure with respect to an air volume in a vial. Three different profiles are illustrated with a first one 830 which is indicative of the pressure (in millibars) before delivery, a second profile 832 indicative of the residual pressure of the delivery and a third profile 834 which is indicative of delivering 0.95 ml of a liquid drug over a time span of about 8 seconds.

Figure 37:
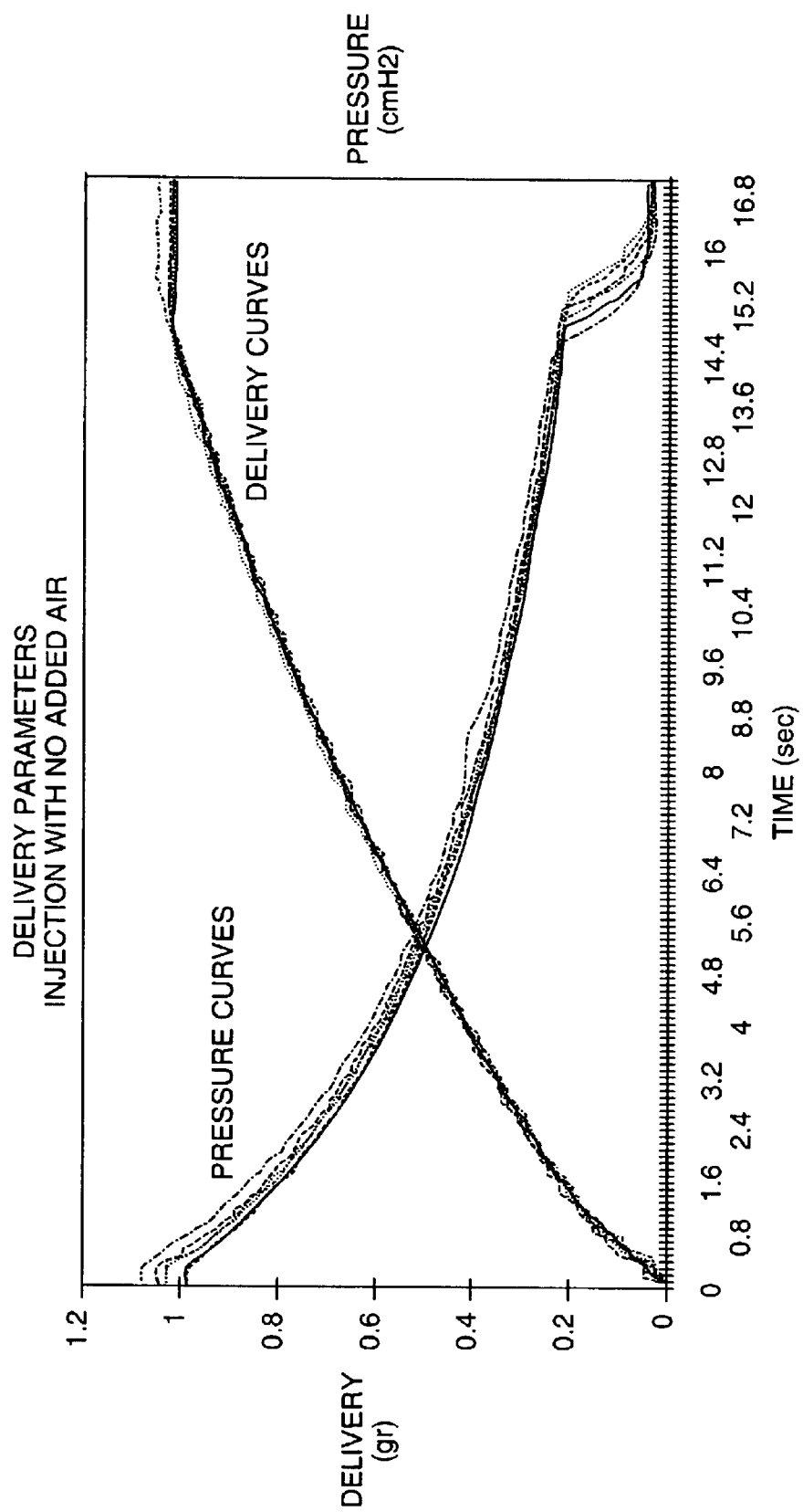
FIG. 37 is a graphical illustration of delivery parameters of injecting a drug with no additional volume of air in accordance with the present invention.

FIG. 37 is a graphical illustration of the delivery parameters for an injection of a liquid drug having no additional air in the vial. As delivery of the drug occurs, the pressurization within the liquid vial decreases over the approximately 17 seconds of delivery. These curves illustrate test results of the delivery process of approximately 1 gram of liquid drug using a single drug delivery device for the same time period.

Figure 38:
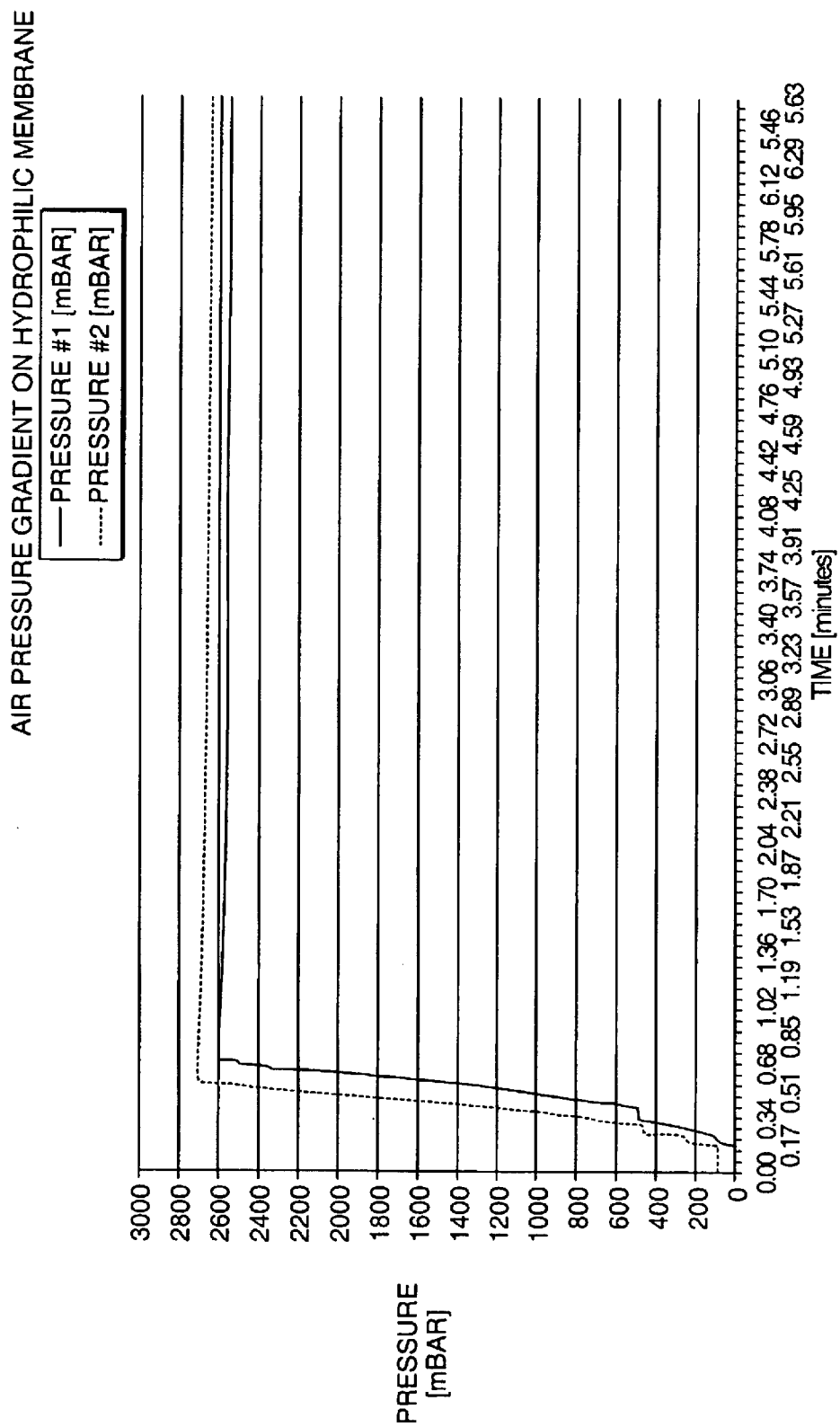
FIG. 38 is a graphical illustration of the air pressure gradient on a hydrophilic membrane in the drug delivery system in accordance with the present invention.

FIG. 38 illustrates test results showing the air pressure gradient on hydrophilic membranes used to minimize or preferably prevent the entry of gas for example, air into the user's tissue. The test results prove membrane safety to insure that the membrane can withstand the pressures in the order of 2,700 millibars for a time duration of about six minutes.

Figure 39:
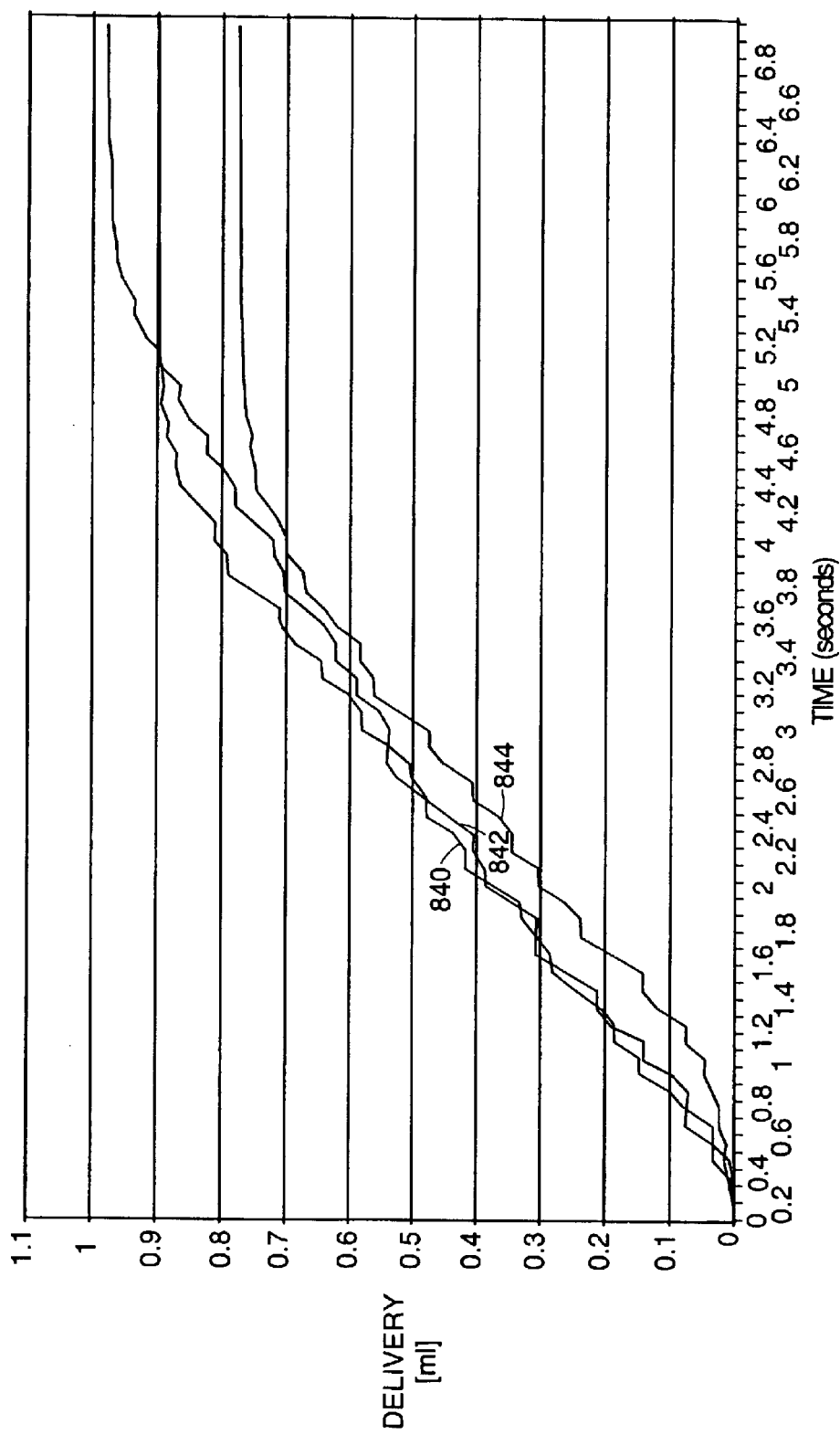
FIG. 39 is a graphical illustration of the delivery profile with respect to time for a vial system containing about 7.5 ml of air in accordance with the present invention.

FIG. 39 graphically illustrates the performance of a drug delivery device in accordance with the present invention. Three delivery profiles 840, 842, 844 (in ml) vs. time (in seconds) are illustrated for a reconstituted lyophilized drug delivery system. The system includes a 0.45 micron pore size hydrophilic membrane to minimize or preferably prevent the flow of gas into the user's tissue. This particular pore size of the membrane provides an adequate particle filter and also allows the shortest time to deliver the drug to the user's tissue.

Figure 40:
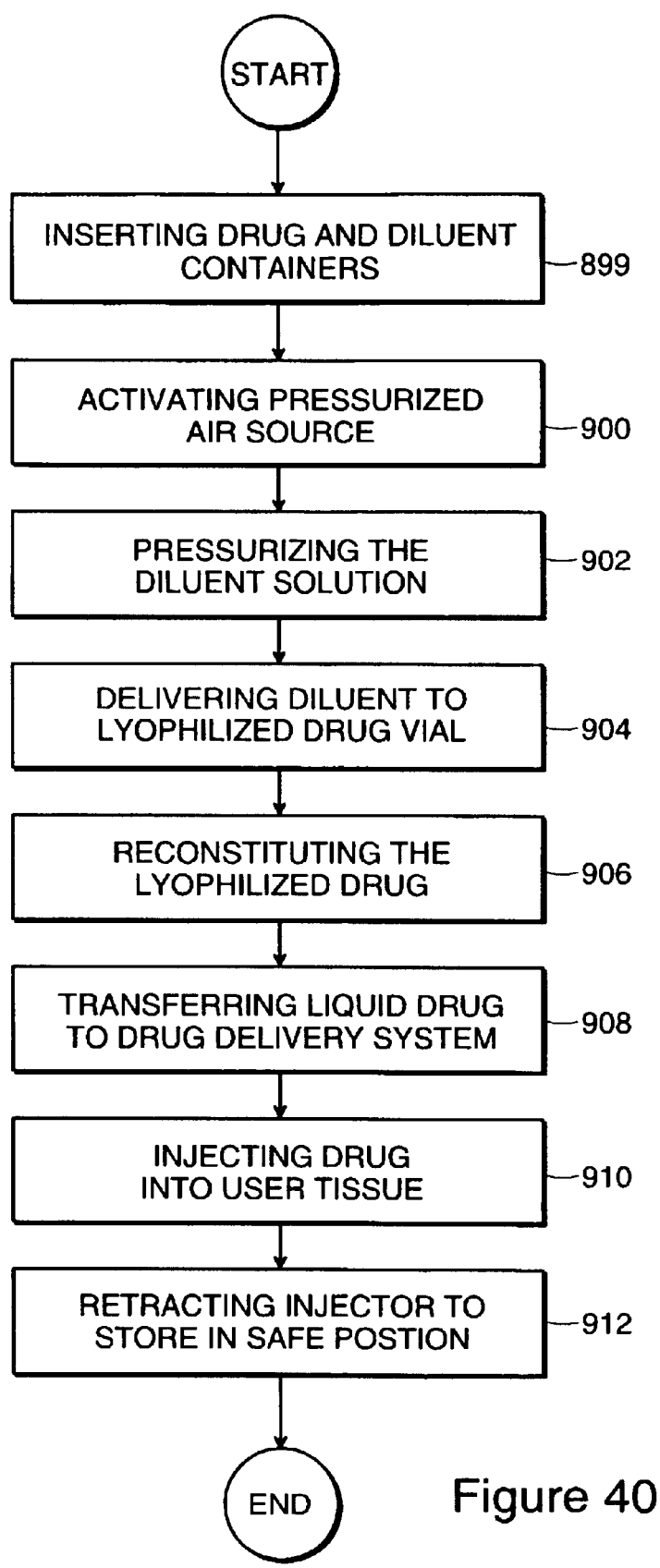
FIG. 40 is a flowchart describing the method of delivery of a reconstituted drug in accordance with the present invention.

FIG. 40 is a flow chart that describes the methods for delivery of a lyophilized drug in accordance with the present invention. The methods include the step 899 of inserting the drug and diluent containers into the drug delivery device. Further per step 900, the method includes activating a pressurized air source which in turn is followed by the step 902 of pressurizing a diluent solution in a diluent vial. As discussed with respect to FIGS. 19A–19F, the pressurizing can be provided by subsystems which include but are not limited to a compressed air supply, a chemical gas generator, a collapsible volume air supply, a standard syringe or cylinder.

The methods further include the step 904 of delivering the pressurized diluent solution to the lyophilized drug vial. The lyophilized drug is reconstituted per step 906 as a result of the mixing of the diluent with the lyophilized drug. The methods further include the step 908 of providing the liquid drug to an injector system or transferring the liquid drug to a detachable delivery device. The liquid drug is then injected into a user's tissue per step 910. The injection needle is then moved to a safe storage position per step 912.

Figure 41:
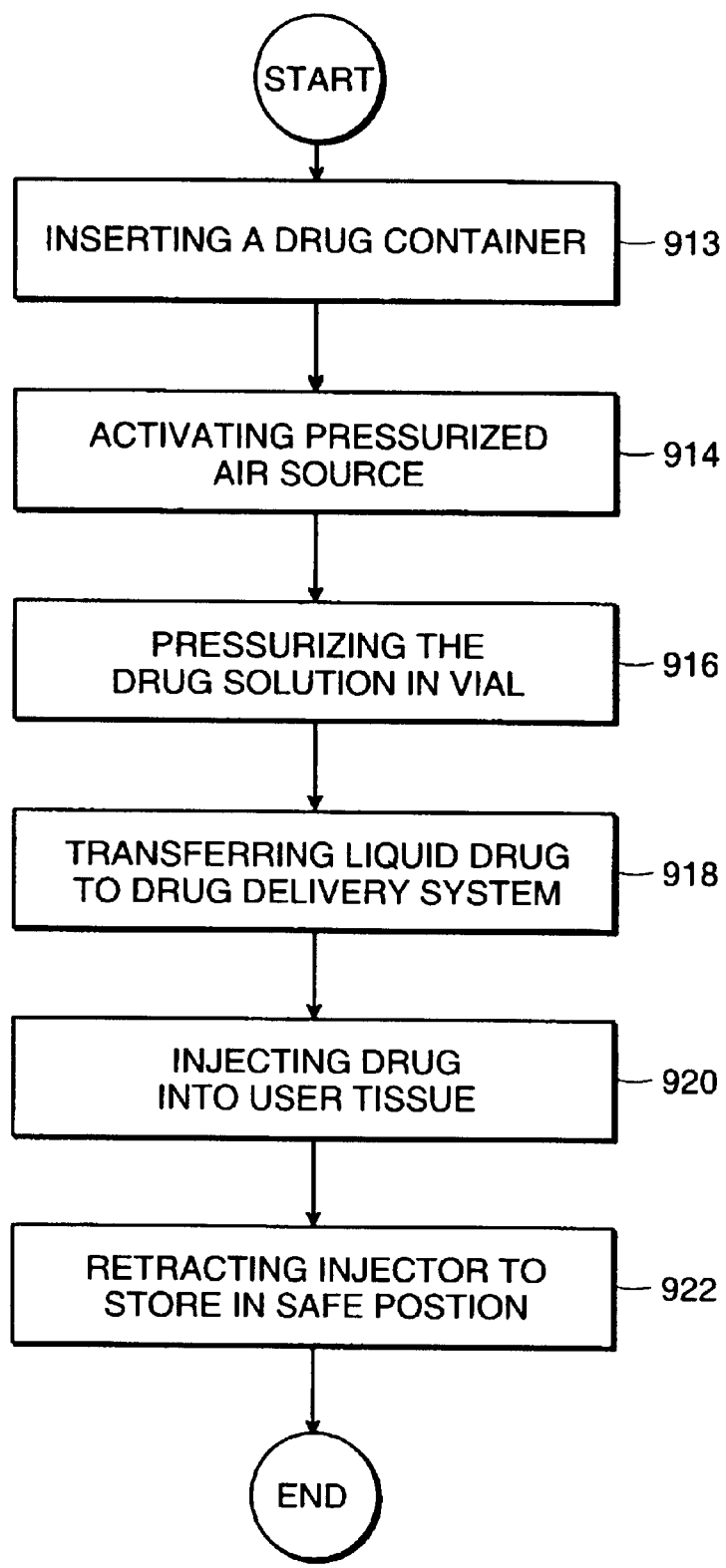
FIG. 41 is a flowchart describing the method of delivery of a liquid drug in accordance with the present invention.

FIG. 41 is a flow chart that describes the methods for delivering a liquid medicament in accordance with the present invention. The methods include the step 913 of inserting a drug container such as a vial into the drug delivery system. Further, per step 914 the method includes activating a pressurized air source for low viscosity drugs. It should be noted that for drugs with a high level of viscosity no pressurization may be required. The method then includes the step 916 of pressurizing the standard drug vial. The pressurized liquid drug is transferred to a drug delivery system such as an injector system, or detachable delivery devices per step 918. The liquid drug is then injected into the tissue of a user per step 920. The method further includes the step 922 of retracting the injector into a safe storage position.

Figure 42:
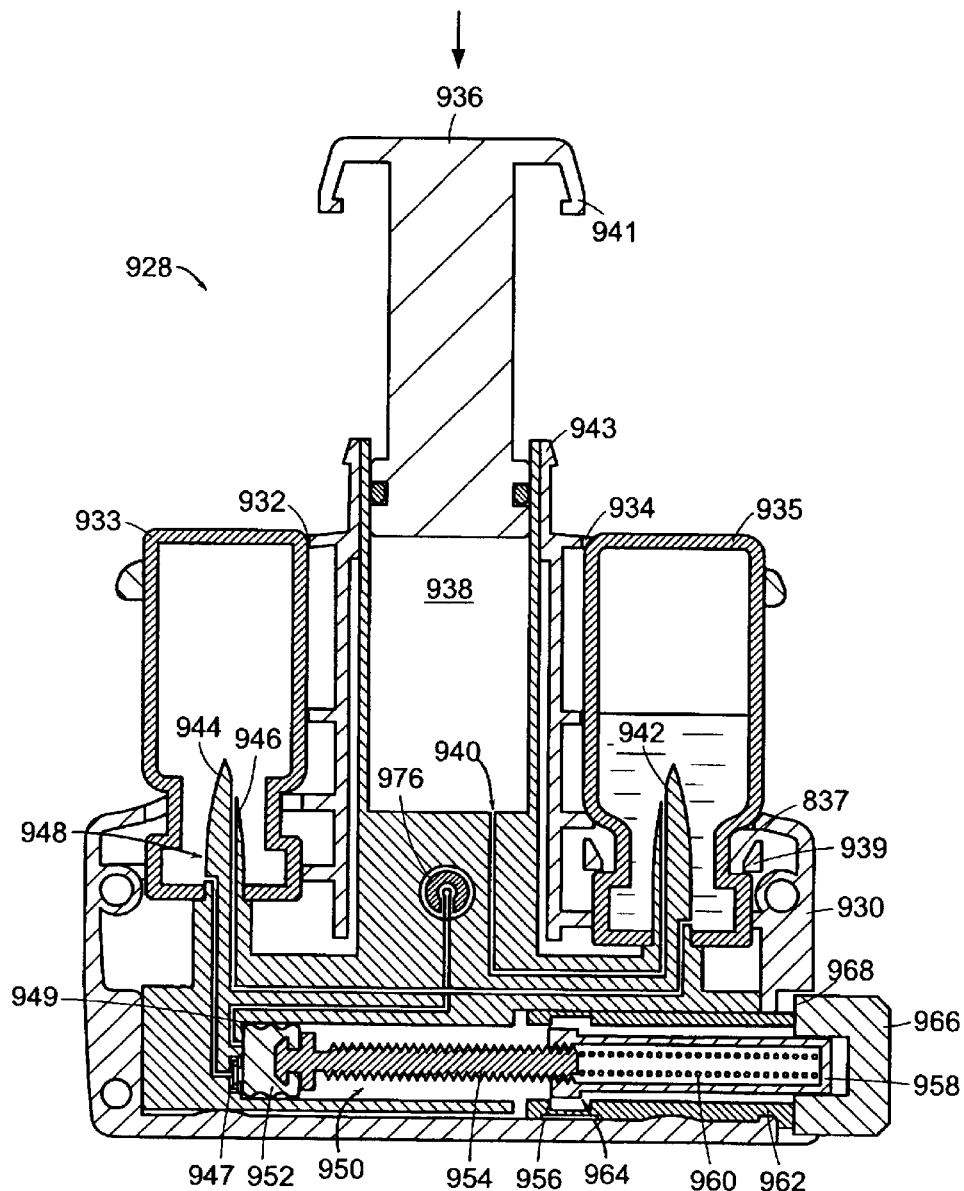
FIG. 42 is a front cross-section view of a preferred embodiment of the liquid drug measurement assembly incorporated into a lyophilization and injection system.

FIG. 42 is a front cross sectional view of a further embodiment of the present invention 928. This embodiment includes a housing 930 having a first recess 932 for receiving a drug container 933 having drug therein and a second recess 934 for receiving a diluent container 935 having diluent therein. The dilent container 935 has an upper lip 937 for locking reception into a snap 939 within the second recess 934. The housing 930 further includes a plunger 936 sealably and slidably engaged in a third recess 938 containing air. The plunger has a catch 941 extending radially inward for locking engagement with a locking collar 943 on the housing 930. The third recess 938 is in communication with the second recess by means of a first channel 940. The diluent container is slidably received on a first spike 942. The drug container is slidably received on a second spike 944. The first spike 942 is in liquid communication with the second spike 944 by means of a second channel 946. The second spike further includes a third channel 948 providing liquid communication between the drug container and a measurement chamber 950. There is a check valve 947 located between the measurement chamber 950 and the third channel 948. The check valve 947 is in the form of flap of rubber covering the entrance to the third channel 948 into the measurement chamber 950 which opens from pressure from the third channel to allow the flow of fluid from the third channel into the measurement chamber, but closes when pressure is applied in the opposite direction and will not allow the flow of fluid into the third channel from the measurement chamber. There is a fourth channel 949 that provides liquid communication between the measurement chamber 950 and a delivery chamber 951.

The measurement chamber 950 includes a piston 952 fixed to one end of a threaded rod 954. The piston 952 is slidably engaged in the measurement chamber 950. The second end of the threaded rod 954 is threadably received into a pair of jaws 956 having mating threads to receive the second end of the threaded rod. The jaws 956 are part of a resilient member 958. The member 958 receives an axial spring 960 therein. The spring 960 is aligned so that its longitudinal axis is parallel to the longitudial axis of the member 958. The spring 960 rests against the second end of the threaded rod 952. The member 958 is held within the housing 930 within a sleeve 962. The sleeve 962 has a radial recess 964 on its internal surface. The radial recess 964 is sized to receive the jaws 956 during use. The member 958 is matingly received into an outer knob 966 in such a way so that the outer knob can control the radial rotation of the member during use. The knob has an internal face 968 which presses against the sleeve 962. The housing 930 further includes an activation assembly 970, shown in detail in FIGS. 46A–C. The activation assembly 970 includes a button 972 slidably engaged within a button channel 971 within the housing 930. The button 972 has an outer surface 979 and an inner annular extension 977 having a decreased diameter from that of the outer surface. The annular extension 977 has an annular recess 978 therein. The annular extension 977 also has an annular slit 980 which forms a pair of annular projections, an inner annular projection 981, and an outer annular projection 982. The inner annular projection 981 frictionaly receives a locking sleeve 984. The locking sleeve 984 has an outwardly extending annular lip 986 having a sloped outer surface to matingly slide over a protuberance 988 fixed to the wall of the activation chamber 976. The protuberance 988 has a sloped surface designed to enable the annular lip to slide over it, but also has a flat end surface 989 for mating abuttment with the a flat lower surface 991 of the annular lip 986 during use.

The button 972 has a delivery needle 973 mounted therein. The delivery needle 973 and button 972 are resiliently mounted on the housing 930 by means of an activation spring 974. The needle 973 has an opening 990, shown in FIG. 46B, along its axis. The opening 990 is designed to align with the delivery chamber 951 during use.

Figure 43:
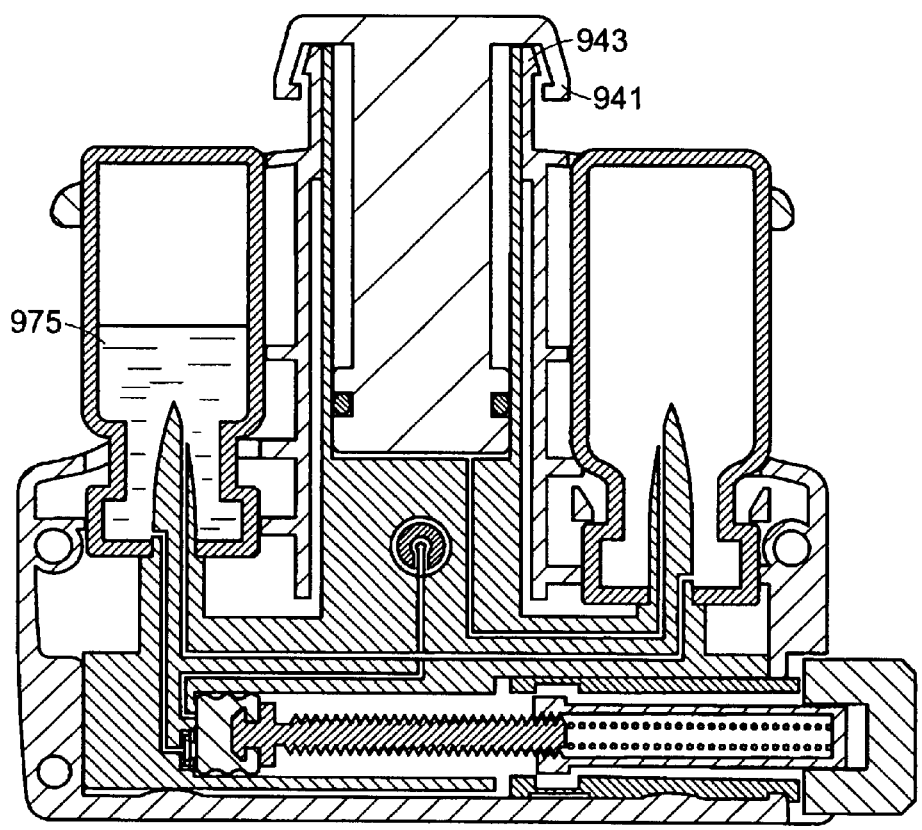
FIG. 43 is a front cross-section view of the preferred embodiment of FIG. 42 wherein the diluent is moved into the drug container to form a drug solution.

To use, the drug container 933 is inserted into the first recess 932 and pressed down until the bottom surface of the drug container is relatively flush with the outer surface of the housing 930 as shown in FIG. 42. When this occurs, the seal of the drug container 933 is broken and the second spike 944 is received into the drug container. The diluent container 935 is inserted into the second recess 934 until the upper lip 937 of the diluent container 935 clears the snap 939. In this position, the first spike 942 is received into the interior of the diluent container 935. The plunger 936 is then fully depressed until the catch 941 is lockingly engaged with the collar 943 on the housing 930. The downward movement of the plunger 936 causes the air within the third recess to move into the diluent container 935 through the first channel 940 as shown in FIG. 42. This causes the diluent within the diluent container 935 to flow into the the drug container 933 through the second channel 946. The introduction of diluent into the drug container creates an administrable drug solution 975 as shown in FIG. 43.

Figure 44:
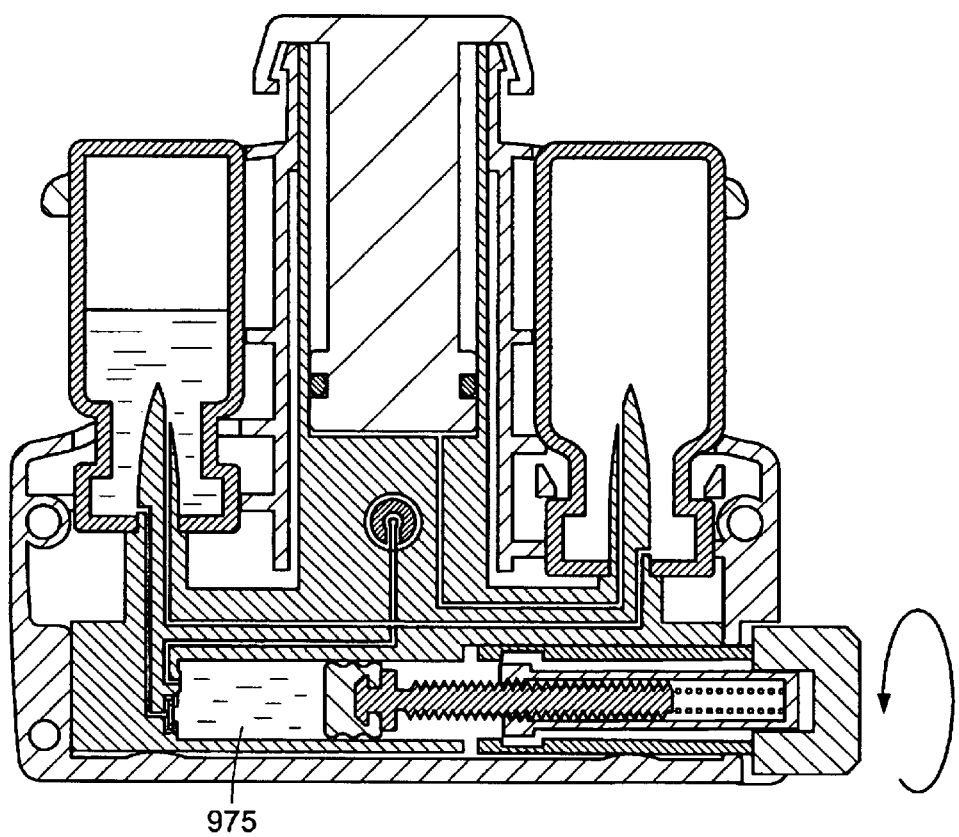
FIG. 44 is a front cross-section view of the preferred embodiment of FIG. 42 wherein the liquid drug is aspirated into the measurement chamber.

In order to measure the appropriate and accurate dose for administration, the user rotates the knob 966 (a shown by the arrow in FIG. 44). As the knob 966 rotates, it causes the jaws 956 to turn which causes the threaded rod 954 and piston 952 to turn and move towards the knob. This causes the drug solution 975 to aspirate into the measurement chamber 950, as shown in FIG. 45. Once the user has rotated the knob 966 to the appropriate position on the housing that indicates the desired dosage, the user pushes the knob into the housing 930. This causes the jaws 956 to move into the radial recess 964 in the sleeve 962 which enables the spring 960 to exert axial force on the threaded rod 954 and piston 952. This results in a flowing of the drug solution 975 from the measurement chamber 950 to the delivery chamber 951, as shown in FIG. 45A.

Figure 45A:
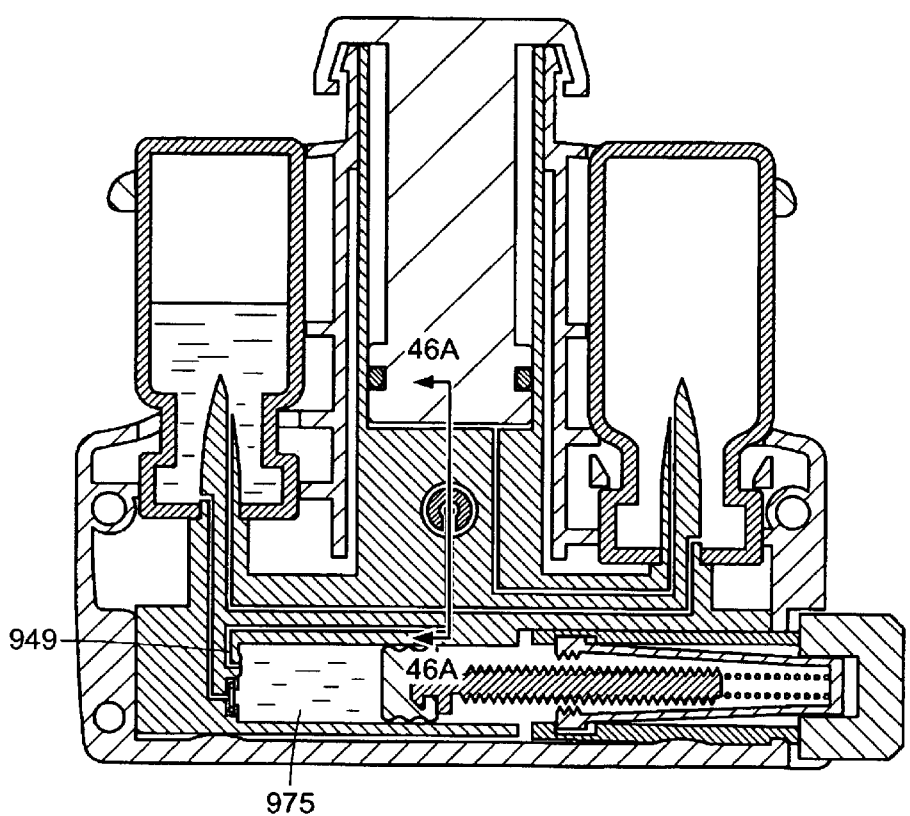
FIG. 45A is a cross-sectional view of the preferred embodiment of FIG. 42 wherein the liquid drug is emptied from the measurement chamber.
Figure 45B:
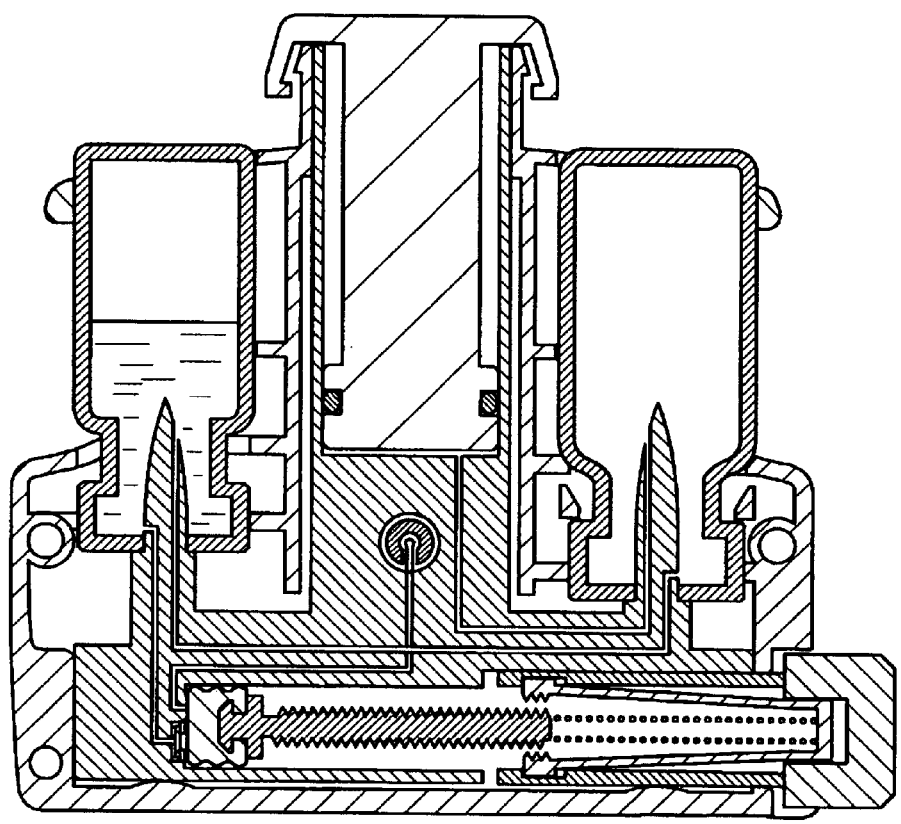
FIG. 45B is a cross-sectional view of the preferred embodiment of FIG. 42 wherein the liquid drug is completely emptied from the measurement chamber.
Figure 46A:
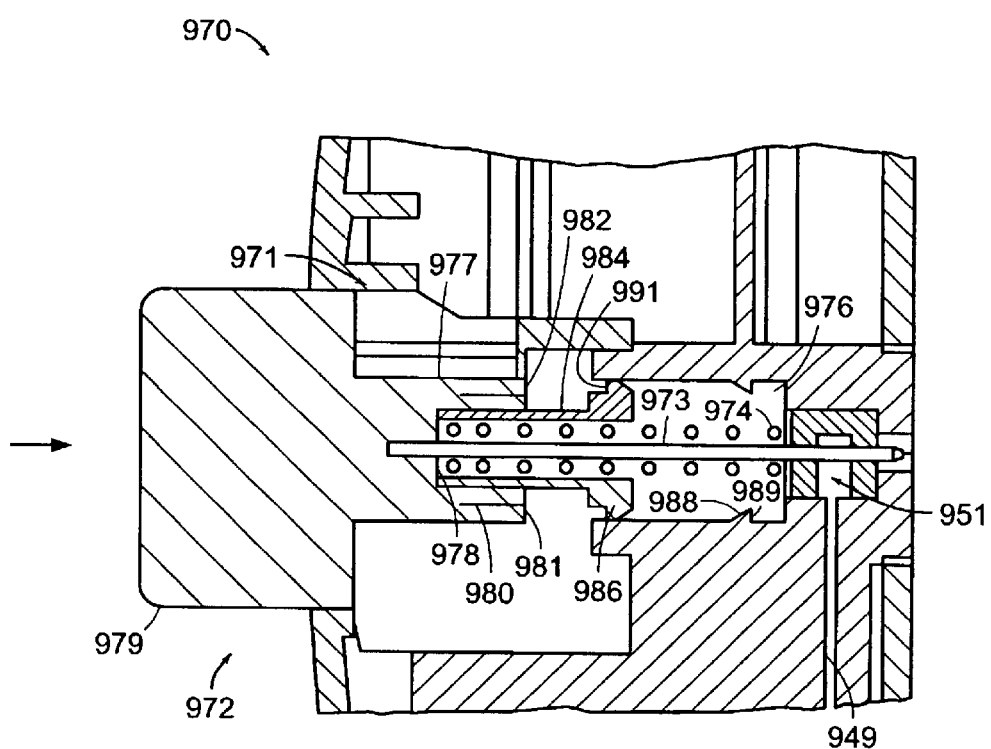
FIG. 46A is a second cross-sectional view of FIG. 45A taken along line 46A—46A showing activation assembly prior to use.
Figure 46B:
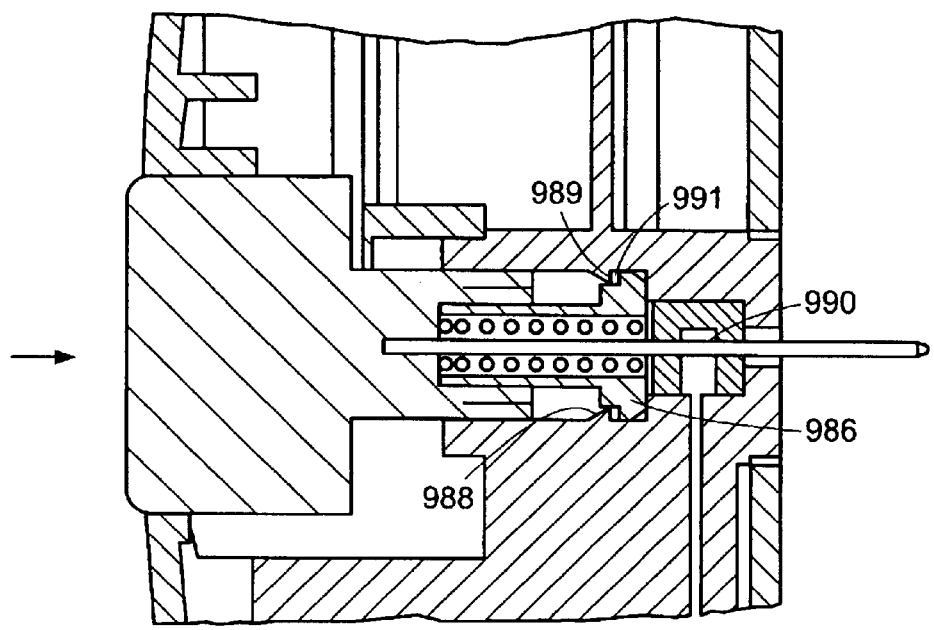
FIG. 46B is a second cross-sectional view of FIG. 45A taken along line 46A—46A showing activation assembly during use.
Figure 46C:
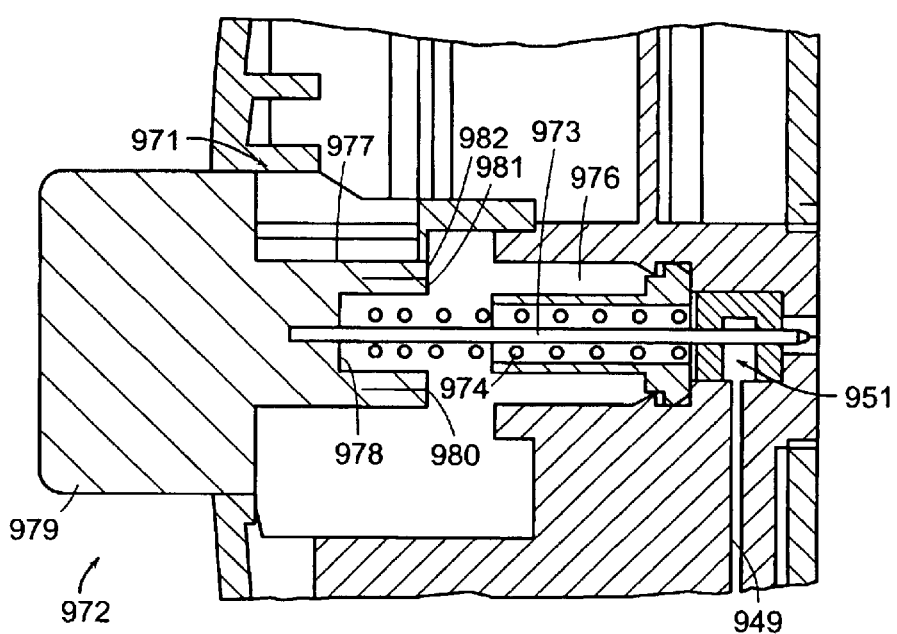
FIG. 46C is a second cross-sectional view of FIG. 45A taken along line 46A—46A showing activation assembly after use.

FIG. 46A is a second cross-sectional view of FIG. 45A taken along line 46A—46A showing activation assembly prior to use;

FIG. 46B is a second cross-sectional view of FIG. 45A taken along line 46A—46A showing activation assembly during use; and FIG. 46C is a second cross-sectional view of FIG. 45A taken along line 46A—46A showing activation assembly after use.

At that time, the user places the side of the housing opposed to the button 972 against the surface of the skin in the desired area. The user is free to compress the button 972 which causes the needle 973 to move through an aperture in the housing 930 and through the skin surface and into the skin. As the needle 973 moves into the appropriate position within or beneath the skin, the needle opening 990 aligns with the delivery chamber 951, as shown in FIG. 46B. This enables the drug solution 975 to flow out of the delivery chamber 951 and into the user via the needle 973. The pressing of the button 972 also causes the annular recess 978 to travel along the locking sleeve 984. As this occurs, the sloped surface of the lip 986 of the locking sleeve 984 passes over the protuberance 988. When the button 972 is fully depressed, the annular recess 978 is fully received into the locking sleeve 984 and the bottom of the annular recess 978 abuts the end of the locking sleeve 984, as shown in FIG. 46B.

Upon completion of delivery of the drug solution 975, the user ceases to depress the button 972 which causes the needle 973 to retract into the housing 930 by means of the spring 974. The spring 974 also forces the button 972 to move away from the housing 930. This also causes the annular recess 978 to move in a similar direction. As the annular recess 978 moves in response to the force exerted by the spring 974, the locking sleeve 984 is held into place by means of the abutting relationship between the lip 986 and the protuberance 988. Once the button 972 has moved back into its original position, the annular recess 978 is no longer in contact with the locking sleeve 984. As a result, the inner projection 981 separates from the outer projection 982 causing the inner projection 981 to move radially inward, as shown in FIG. 46C. Thus, if the user were to compress the button 972 again, the inner projection 981 would abut the bottom of the locking sleeve 984 and thus prevent further travel of the button 972 into the housing 930. Because the delivery needle 973 is mounted on the button 972, any further compression of the button 972 also prevents the delivery needle 973 from moving out of its retracted position within the housing 930. This prevents reuse of the device and protects the user or a care giver against accidental pricking of the needle 973 which prevents contamination of numerous diseases and viruses spread through contact with bodily fluids.

It is further appreciated that the present invention may be used to deliver a number of drugs. The term "drug" used herein includes but is not limited to peptides or proteins (and mimetic thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides, proteins or hormones (or any mimetic or analogues or any thereof) such as insulin, calcitonin, calcitonin gene regulating protein, atrial natriuretic protein, colony stimulating factor, betaseron, erythropoietin (EPO), interferons such as $\alpha$, $\beta$ or $\gamma$ interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues or antagonists thereof, such as IL-1ra; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anticoagulant agents such as heparin, hirudin, and analogues thereof; anti-emetic agents such as scopolamine, ondansetron, domperidone, metoclopramide, and analogues thereof; cardiovacular agents, anti-hypertensive agents and vasodilators such as diltiazem, clonidine, nifedipine, verapamil, isosorbide-5-monotritate, organic nitrates, agents used in treatment of heart disorders, and analogues thereof; sedatives such as benzodiazepines, phenothiazines, and analogues thereof; chelating agents such as defroxanune, and analogues thereof; anti-diuretic agents such as desmopressin, vasopressin, and analogues thereof; antianginal agents such as fluorouracil, bleomycin, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluvoxamine, bisoprolol, tacrolimus, sacrolimus and cyclosporin.

While this invention has been particularly shown and described with references to preferred embodiments thereof, it will be understood by those skilled in the art that various changes in form and details may be made therein without departing from the spirit and scope of the invention as defined by the appended claims. For example, some of the features of the position independence can be used in connection with reconstitution combination systems, transfer systems or injection systems. Likewise interlock features may be used with any of the aforementioned systems.

What is claimed is:

1. A device for measuring and delivering a desired volume of liquid drug, said device comprising:
    a housing including:
        a first chamber containing liquid drug;
        a measurement chamber in liquid communication with the first chamber;
        a measurement assembly for establishing a desired amount of liquid drug, said measurement assembly comprising:
            a piston, slidably received in the measurement chamber;
            a member in radial transmission relation to the piston; and
            a knob in radial transmission relation to the member whereby movement of the knob moves the piston along the measurement chamber which causes aspiration of the liquid drug into the measurement chamber; and
        parenteral delivery means for delivering said desired amount of liquid drug to a living being.

2. The device of claim 1 wherein the piston comprises a piston head and a threaded rod.

3. The device of claim 2 wherein the piston head is made of rubber.

4. The device of claim 1 wherein the member has axial internal threads along a portion of its length.

5. The device of claim 1 wherein the measurement assembly further comprises:
    a sleeve slidably received within the measurement chamber along a portion of the length of the chamber, and for slidably receiving the member, the sleeve having a annular recess;
    and a spring mounted axially within the sleeve.

6. The device of claim 5 wherein the member further comprises an annular extension along a portion of the outer surface of the member to matingly engage the annular recess when said knob is pressed.

7. The device of claim 6 wherein one end of the sleeve abuts the measurement chamber wall and the other end of the sleeve abuts the knob.

8. The device of claim 1 wherein said parenteral delivery means comprises a needle in fluid communication with said measurement chamber, said needle being movable out of said housing defining a first position and into the skin of a living being, defining a second position, for delivering said measured drug volume therein.

9. The device of claim 8 wherein said parenteral delivery means further comprises means for automatically returning said needle to said first position from said second position when drug delivery is completed.

10. The device of claim 9 wherein said parenteral delivery means further comprises means for preventing said needle from being moved to said second position after said needle has been automatically returned to said first position.

11. A device for delivering a measured volume of drug comprising:
a first chamber containing liquid drug;
a measurement chamber in liquid communication with the first chamber;
a measurement assembly comprising a piston being frictionally received into the measurement chamber, a member in radial transmission relation to the piston, the member having an annular extension, and a knob in radial transmission relation to the member and slidably and resiliently mounted to the measurement chamber;
an axial spring providing axial force to the piston and the knob;
a sleeve slidably mounted within a portion of the length of the measurement chamber, the sleeve having a radial recess for mating receipt of the annular extension of the member; and
a needle in liquid communication with the measurement chamber, whereby when the knob is rotated, it causes the member to engage in radial transmission with the piston causing the piston to move axially along the length of measurement chamber thereby causing drug solution to aspirate into the measurement chamber, and then when the knob is depressed inwardly relative to the measurement chamber it causes the annular extension to be received into the radial recess in the sleeve, thereby releasing the radial transmission relation between the member and the piston, causing axial extension of the spring against the piston and flow of liquid drug from the measurement chamber and through the needle.

12. The device of claim 11 wherein the piston comprises a piston head and a threaded rod.

13. The device of claim 12 wherein the piston head is made of rubber.

14. The device of claim 11 where the member has axial internal threads along a portion of its length.

15. The device in claim 11 wherein one end of the sleeve abuts the measurement chamber wall and the other end of the sleeve abuts the knob.

16. A method of measuring a volume of liquid drug comprising the steps of:
providing a first chamber containing liquid drug;
providing a measurement chamber in liquid communication with the first chamber;
providing a measurement assembly comprising a piston, slidably received in the measurement chamber, a member in radial transmission relation to the piston, and a knob in radial transmission relation to the member and slidably mounted axially to the measurement chamber; and
rotating the knob to a desired setting thereby causing liquid drug to aspirate from the first chamber into the measurement chamber to reach a measured volume.

17. A method of delivering a measured volume of liquid drug comprising the steps of:
providing a first chamber containing liquid drug;
providing a measurement chamber in liquid communication with the first chamber;
providing a measurement assembly comprising a piston, slidably received in the measurement chamber, a member in radial transmission relation to the piston and having an annular extension, and a knob in radial transmission relation to the member and slidably mounted axially to the measurement chamber;
mounting an axial spring along the inner length of the member, the spring abutting one end of the piston;
providing a sleeve slidably mounted with a portion of the length of the measurement chamber, the sleeve having a radial recess for mating receipt of the annular extension of the member;
providing a needle in liquid communication with the measurement chamber;
rotating the knob to a desired setting thereby causing liquid drug to aspirate from the first chamber into the measurement chamber to reach a measured volume; and
pushing the knob axially inward relative to the measurement chamber thereby causing the annular extension to be received into the radial recess in the sleeve, thereby causing axial extension of the spring against the piston and flow of liquid drug from the measurement chamber and through the needle.

* * * * *